United States Patent
Masuyama et al.

(10) Patent No.: US 10,725,380 B2
(45) Date of Patent: Jul. 28, 2020

(54) COMPOUND, RESIN, RESIST COMPOSITION AND METHOD FOR PRODUCING RESIST PATTERN

(71) Applicant: SUMITOMO CHEMICAL COMPANY, LIMITED, Tokyo (JP)

(72) Inventors: Tatsuro Masuyama, Osaka (JP); Satoshi Yamamoto, Osaka (JP); Koji Ichikawa, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/835,102

(22) Filed: Aug. 25, 2015

(65) Prior Publication Data

US 2016/0052860 A1    Feb. 25, 2016

(30) Foreign Application Priority Data

Aug. 25, 2014 (JP) .................. 2014-170762
Sep. 18, 2014 (JP) .................. 2014-189934

(51) Int. Cl.
| | |
|---|---|
| *G03F 7/004* | (2006.01) |
| *C08F 214/18* | (2006.01) |
| *G03F 7/38* | (2006.01) |
| *G03F 7/039* | (2006.01) |
| *C08F 122/10* | (2006.01) |
| *G03F 7/32* | (2006.01) |
| *C08F 122/18* | (2006.01) |
| *C07C 69/757* | (2006.01) |
| *C08F 218/00* | (2006.01) |

(52) U.S. Cl.
CPC .......... *G03F 7/0397* (2013.01); *C07C 69/757* (2013.01); *C08F 122/10* (2013.01); *C08F 122/18* (2013.01); *C08F 214/18* (2013.01); *G03F 7/0046* (2013.01); *G03F 7/325* (2013.01); *G03F 7/38* (2013.01); *C07C 2601/08* (2017.05); *C07C 2601/14* (2017.05); *C07C 2603/74* (2017.05); *C08F 218/20* (2020.02)

(58) Field of Classification Search
CPC ........ G03F 7/0397; G03F 7/38; C08F 122/18; C08F 214/18; C08F 2218/20
USPC ...... 430/270.1, 907, 910, 326, 330; 525/282
See application file for complete search history.

(56) References Cited

U.S. PATENT DOCUMENTS

| | | |
|---|---|---|
| 3,779,778 A | 12/1973 | Smith et al. |
| 3,849,137 A | 11/1974 | Barzynski et al. |
| 4,576,902 A | 3/1986 | Saenger et al. |
| 4,822,716 A | 4/1989 | Onishi et al. |
| 4,857,437 A | 8/1989 | Banks et al. |
| 5,017,453 A | 5/1991 | Onishi et al. |
| 5,073,476 A | 12/1991 | Meier et al. |
| 5,198,520 A | 3/1993 | Onishi et al. |
| 5,260,410 A | 11/1993 | Schwalm |
| 5,453,341 A | 9/1995 | Schwalm |
| 8,999,622 B2* | 4/2015 | Iwato ............ G03F 7/0046 430/270.1 |
| 2002/0098441 A1 | 7/2002 | Okino et al. |
| 2003/0149225 A1 | 8/2003 | Okino et al. |
| 2004/0043324 A1 | 3/2004 | Okino et al. |
| 2005/0031990 A1 | 2/2005 | Okino et al. |
| 2005/0031991 A1 | 2/2005 | Okino et al. |
| 2005/0037283 A1 | 2/2005 | Okino et al. |
| 2005/0037284 A1 | 2/2005 | Okino et al. |
| 2005/0048400 A1 | 3/2005 | Okino et al. |
| 2008/0193874 A1 | 8/2008 | Takata et al. |
| 2010/0022730 A1 | 1/2010 | Hatakeyama et al. |
| 2010/0035180 A1 | 2/2010 | Shimada et al. |
| 2010/0151380 A1 | 6/2010 | Ando et al. |
| 2010/0203446 A1 | 8/2010 | Ichikawa et al. |
| 2011/0171576 A1 | 7/2011 | Yamaguchi et al. |

(Continued)

FOREIGN PATENT DOCUMENTS

| | | |
|---|---|---|
| DE | 39 14 407 A1 | 10/1990 |
| EP | 0 126 712 A1 | 11/1984 |

(Continued)

OTHER PUBLICATIONS

Luis et al., "Non Concerted Pathways in the Generation of Dehydroarenes by Thermal Decomposition of Diaryliodonium Carboxylates", Tetrahedron, 1989, vol. 45, No. 19, pp. 6281-6296.

(Continued)

*Primary Examiner* — John S Chu
(74) *Attorney, Agent, or Firm* — Birch, Stewart, Kolasch & Birch, LLP

(57) ABSTRACT

A compound represented by the formula (I).

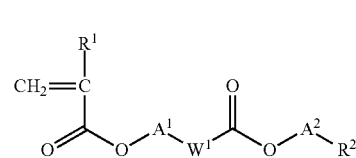

(I)

wherein $R^1$ represents a hydrogen atom, a halogen atom or a $C_1$ to $C_6$ alkyl group that may have a halogen atom; $R^2$ represents a $C_1$ to $C_{12}$ fluorinated saturated hydrocarbon group; $W^1$ represents a $C_5$ to $C_{18}$ divalent alicyclic hydrocarbon group; $A^1$ and $A^2$ independently represents a single bond or *—$A^3$—$X^1$—($A^4$—$X^2$)$_a$—; $A^3$ and $A^4$ independently represents a $C_1$ to $C_6$ alkanediyl group; $X^1$ and $X^2$ independently represents —O—, —CO—O— or —O—CO—; a represents 0 or 1; and * represents a bond to an oxygen atom.

3 Claims, No Drawings

(56) References Cited

U.S. PATENT DOCUMENTS

| | | |
|---|---|---|
| 2011/0177455 A1 | 7/2011 | Harada et al. |
| 2011/0200935 A1 | 8/2011 | Masuyama et al. |
| 2011/0201823 A1 | 8/2011 | Yoshida et al. |
| 2012/0034563 A1 | 2/2012 | Ichikawa et al. |
| 2012/0100483 A1 | 4/2012 | Masuyama et al. |
| 2012/0328986 A1 | 12/2012 | Anryu et al. |
| 2013/0022912 A1* | 1/2013 | Sato .................. C08F 220/28 430/270.1 |
| 2013/0084523 A1* | 4/2013 | Nakamura ............. G03F 7/004 430/270.1 |
| 2013/0115556 A1* | 5/2013 | Iwato ................. G03F 7/0046 430/285.1 |
| 2013/0143157 A1 | 6/2013 | Tanaka et al. |

FOREIGN PATENT DOCUMENTS

| | | | |
|---|---|---|---|
| JP | 55-164824 A | 12/1980 | |
| JP | 62-69263 A | 3/1987 | |
| JP | 62-153853 A | 7/1987 | |
| JP | 63-26653 A | 2/1988 | |
| JP | 63-146029 A | 6/1988 | |
| JP | 63-146038 A | 6/1988 | |
| JP | 63-163452 A | 7/1988 | |
| JP | 2000-122294 A | 4/2000 | |
| JP | 2008-209917 A | 9/2008 | |
| JP | 2010-61117 A | 3/2010 | |
| JP | 2010-152341 A | 7/2010 | |
| JP | 2010-204634 A | 9/2010 | |
| JP | 2010-204646 A | 9/2010 | |
| JP | 2011-39502 A | 2/2011 | |
| JP | 2011-162768 A | 8/2011 | |
| JP | 2011-191745 A | 9/2011 | |
| JP | 2012-6908 A | 1/2012 | |
| JP | 2012-41274 A | 3/2012 | |
| JP | 2012-53460 A | 3/2012 | |
| JP | 2012053460 A | * 3/2012 | |
| JP | 2012-72109 A | 4/2012 | |
| JP | 2012-229206 A | 11/2012 | |
| JP | 2013-41233 A | 2/2013 | |
| JP | 2013-68821 A | 4/2013 | |
| JP | 2013-166919 A | 8/2013 | |
| WO | 2008/015876 A1 | 2/2008 | |

OTHER PUBLICATIONS

Japanese Office Action issued in the corresponding Japanese Patent Application No. 2015-164502 dated Oct. 9, 2018.

\* cited by examiner

COMPOUND, RESIN, RESIST COMPOSITION AND METHOD FOR PRODUCING RESIST PATTERN

CROSS-REFERENCE TO RELATED APPLICATIONS

This application claims priority to Japanese Applications Nos. 2014-170762 and 2014-189934 filed on Aug. 25, 2014 and Sep. 18, 2014 respectively. The entire disclosures of Japanese Applications Nos. 2014-170762 and 2014-189934 is incorporated hereinto by reference.

BACKGROUND OF THE INVENTION

1. Field of the Invention

The present invention relates to a compound, a resin, a composition, a resist composition and a method for producing the resist pattern.

2. Related Art

A resist composition which contains a resin having the following structural unit is described in Patent document of JP2012-53460A.

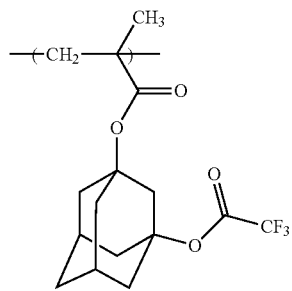

SUMMARY OF THE INVENTION

The present invention provides following inventions of <1> to <10>.

<1> A compound represented by formula (I)

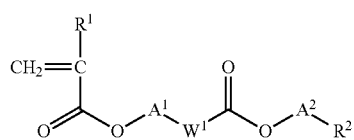

wherein $R^1$ represents a hydrogen atom, a halogen atom or a $C_1$ to $C_6$ alkyl group that may have a halogen atom;
$R^2$ represents a $C_1$ to $C_{12}$ fluorinated saturated hydrocarbon group;
$W^1$ represents a $C_5$ to $C_{18}$ divalent alicyclic hydrocarbon group;
$A^1$ and $A^2$ each independently represent a single bond or *—$A^3$—$X^1$—$(A^4$—$X^2)_a$—;
$A^3$ and $A^4$ each independently represent a $C_1$ to $C_6$ alkanediyl group;
$X^1$ and $X^2$ each independently represents —O—, —CO—O— or —O—CO—;
a represents 0 or 1; and
* represents a binding site to an oxygen atom.
<2> The compound according to <1>, wherein $W^1$ is an adamantanediyl group or a cyclohexanediyl group.
<3> The compound according to <2>, wherein the adamantanediyl group is any one of the groups represented by formulae (Ad-1) to (Ad-3);

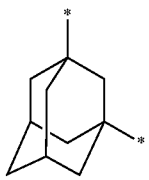

(Ad-1)

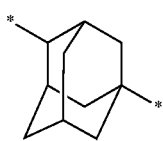

(Ad-2)

(Ad-3)

wherein one of * is a binding site to $A^1$ and another * is a binding site to a carbonyl group.
<4> The compound according to any one of <1> to <3>, wherein $A^1$ is a single bond.
<5> The compound according to any one of <1> to <4>, wherein $R^2$ is a $C_{12}$ to $C_{12}$ fluorinated alkyl group.
<6> The compound according to any one of <1> to <5>, wherein
$R^2$ is —$(CH_2)_n$—$R^f$,
where n represents an integer of 1 to 6, and
$R^f$ represents a $C_1$ to $C_6$ perfuloroalkyl group.
<7> The compound according to any one of <1> to <5>, wherein
$R^2$ is —$CH(R^{fa})(R^{fb})$;
where $R^{fa}$ and $R^{fb}$ each independently represent a $C_1$ to $C_6$ perfuloroalkyl group, provided that $R^{fa}$ and $R^{fb}$ have 11 or less of carbon atoms in total.
<8> A resin including a structural unit derived from the compound according to any one of <1> to <7>.
<9> A resist composition including the resin according to <8>, a resin having an acid-labile group, and an acid generator.
<10> A method for producing a resist pattern including steps (1) to (5);
(1) applying the resist composition according to <9> onto a substrate;
(2) drying the applied composition to form a composition layer;
(3) exposing the composition layer;
(4) heating the exposed composition layer, and
(5) developing the heated composition layer.

DETAILED DESCRIPTION OF THE PREFERRED EMBODIMENTS

"(Meth)acrylic monomer" means a monomer having a structure of "$CH_2$=CH—CO—" or "$CH_2$=$C(CH_3)$—

CO—", as well as "(meth)acrylate" and "(meth)acrylic acid" mean "an acrylate or methacrylate" and "an acrylic acid or methacrylic acid," respectively. Herein, chain structure groups include those having a linear structure and those having a branched structure. The indefinite articles "a" and "an" are taken as the same meaning as "one or more".

In the specification, the term "solid components" means components other than solvents in a resist composition.

<Compound (I)>

The compound of the present invention (which is sometimes referred to as "compound (I)") is a compound represented by the formula (I);

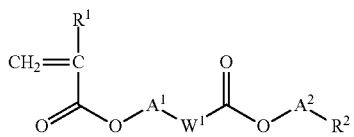

wherein $R^1$ represents a hydrogen atom, a halogen atom or a $C_1$ to $C_6$ alkyl group that may have a halogen atom;

$R^2$ represents a $C_1$ to $C_{12}$ fluorinated saturated hydrocarbon group;

$W^1$ represents a $C_5$ to $C_{18}$ divalent alicyclic hydrocarbon group;

$A^1$ and $A^2$ each independently represent a single bond or *—$A^3$—$X^1$—$(A^4$—$X^2)_a$—;

$A^3$ and $A^4$ each independently represent a $C_1$ to $C_6$ alkanediyl group;

$X^1$ and $X^2$ each independently represents —O—, —CO—O— or —O—CO—;

a represents 0 or 1; and

* represents a binding site to an oxygen atom.

Examples of the alkyl group of $R^1$ include methyl, ethyl, n-propyl, isopropyl, n-butyl, sec-butyl, tert-butyl, n-pentyl and n-hexyl groups, preferably include a $C_1$ to $C_4$ alkyl group, more preferably a methyl or ethyl group.

Examples of the halogen atom for $R^1$ include fluorine, chlorine, bromine or iodine atom.

Examples of the alkyl group having the halogen atom for $R^1$ include trifluoromethyl, perfluoroethyl, perfluoropropyl, perfluoro-isopropyl, perfluorobutyl, perfluoro-sec-butyl, perfluoro-tert-butyl, perfluoropentyl, perfluorohexyl, perchloromethyl, perbromomethyl and periodomethyl groups.

$R^1$ is preferably a hydrogen atom or a methyl group.

Examples of $C_1$ to $C_{12}$ fluorinated saturated hydrocarbon group of $R^2$ include difluoromethyl, trifluoromethyl, 1,1-difluoroethyl, 2,2-difluoroethyl, 2,2,2-trifluoroethyl, perfluoroethyl, 1,1,2,2-tetrafluoropropyl, 1,1,2,2,3,3-hexafluoropropyl, perfluoroethyl methyl, 1-(trifluoromethyl)-2,2,2-trifluoroethyl, 1-(trifluoromethyl)-2,2,3,3,3-pentafluoropropyl, 1-(perfluoroethyl)-2,2,3,3,3-pentafluoropropyl, 1-(trifluoromethyl) -1,2,2,2-tetrafluoroethyl, perfluoropropyl, 1,1,2,2-tetrafluorobutyl, 1,1,2,2,3,3-hexafluorobutyl 1,1,2, 2,3,3,4,4-octafluorobutyl, perfluorobutyl, 1,1-bis(trifluoromethyl)methyl-2,2,2-trifluoroethyl, 2-(perfluoropropyl)ethyl, 1,1,2,2,3,3,4,4-octafluoropentyl s, perfluoropentyl, 1,1,2,2,3,3,4,4,5,5-decafluoropentyl, 1,1-bis(trifluoromethyl) 2,2,3,3,3-pentafluoropropyl, perfluoropentyl, 2-(perfluorobutyl)ethyl, 1,1,2,2,3,3,4,4,5,5-decafluorohexyl, 1,1,2,2,3,3,4,4,5,5,6,6-dodecafluorohexyl, perfluoropentylmethyl, perfluorohexyl, perfluorocyclohexyl and perfluoroadamantyl groups.

$R^2$ is preferably a $C_1$ to $C_{12}$ fluorinated alkyl group, and more preferably $(CH_2)_n$—$R^f$ or —$CH(R^{fa})(R^{fb})$.

n represents an integer of 1 to 6, preferably 1 to 4, more preferably 1 to 3, and still more preferably 1 or 2, further more preferably 2.

$R^f$ represents a $C_1$ to $C_6$ perfuloroalkyl group, preferably a $C_2$ to $C_4$ perfuloroalkyl group, and more preferably $C_3$ to $C_4$ perfuloroalkyl group.

$R^{fa}$ and $R^{fb}$ each independently represent a $C_1$ to $C_6$ perfuloroalkyl group, preferably a $C_1$ to $C_4$ perfuloroalkyl group, more preferably $C_1$ to $C_3$ perfuloroalkyl group, and still more preferably a $C_1$ to $C_2$ perfuloroalkyl group.

Examples of the $C_5$ to $C_{18}$ divalent alicyclic hydrocarbon group for $W^1$ include cyclopentanediyl, cyclohexanediyl, adamantanediyl and norbornanedily group. Among these, cyclohexanediyl and adamantanediyl groups are preferred, and an adamantanediyl group is more preferred.

The adamantanediyl group is preferably a group represented by any one of the formulae (Ad-1) to (Ad-3), more preferably a group represented by one of the formulae (Ad-1) to (Ad-2), and still more preferably a group represented by the formula (Ad-1). In the formulaes (Ad-1) to (Ad-3), one of * is a bond to $A^1$ and another * is a bond to a carbonyl group.

Examples of the $C_1$ to $C_6$ alkanediyl group for $A^3$ and $A^4$ include a chain alkanediyl group such as methylene, ethylene, propane-1,3-diyl, butane-1,4-diyl, pentane-1,5-diyl and hexane-1,6-diyl groups; and a branched alkanediyl groupsuch as ethane-1,1-diyl, propane-1,2-diyl, butane-1,3-diyl, 2-methylpropane-1,3-diyl, 2-methylpropane-1,2-diyl, pentane-1,4-diyl and 2-methylbutane-1,4-diyl groups.

$A^3$ and $A^4$ are preferably a $C_1$ to $C_3$ divalent alkanediyl group, and more preferably a methylene group or an ethylene group.

Examples of *—$A^3$—$X^1$—$(A^4$—$X^2)_a$—include *—$A^3$—O—, *—$A^3$—O—CO—, *—$A^3$—O—CO—, *—$A^3$—CO—O—$A^4$—CO—O—, *—$A^3$—O—CO—$A^4$—O—, *—$A^3$—O—$A^4$—CO—O—, *—$A^3$—O—O—$A^4$—O—CO— and *—$A^3$—O—CO—$A^4$—O—CO—. Among these, *—$A^3$—O—, *—$A^3$—CO—O—, *—$A^3$—CO—O—$A^4$—CO—O—, and *—$A^3$—O—$A^4$—CO—O— are preferred as *—$A^3$—$X^1$—$(A^4$—$X^2)_a$—.

Each of $A^1$ and $A^2$ is preferably a single bond or *—$A^3$—CO—O—, more preferably a single bond, —$CH_2$—CO—O— or —$C_2H_4$—CO—O—, and still more preferably a single bond or $CH_2$—CO—O—. Specifically, $A^1$ is preferably a single bond. $A^2$ is preferably *—$A^3$—CO—O—.
Examples of the compound (I) include the compounds represented by the following ones.
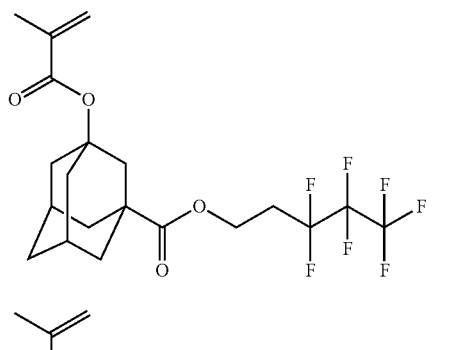
(I-1)
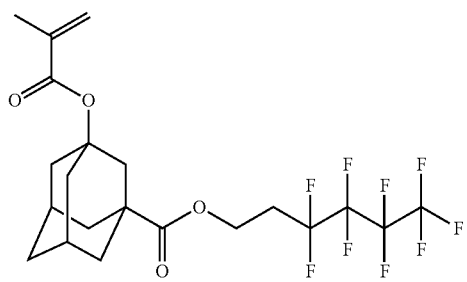
(I-2)
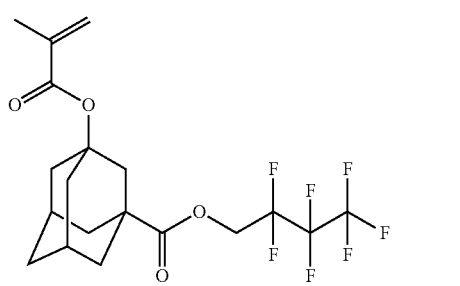
(I-3)
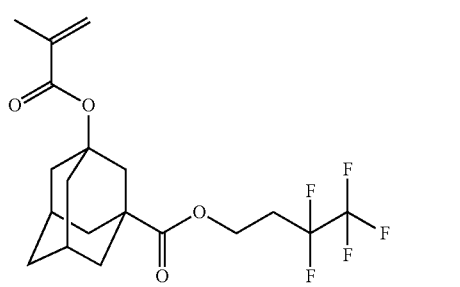
(I-4)
(I-5)
-continued
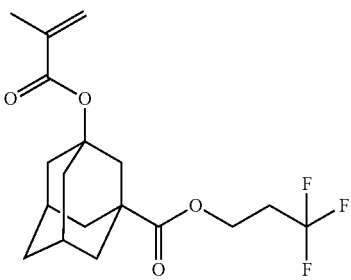
(I-6)
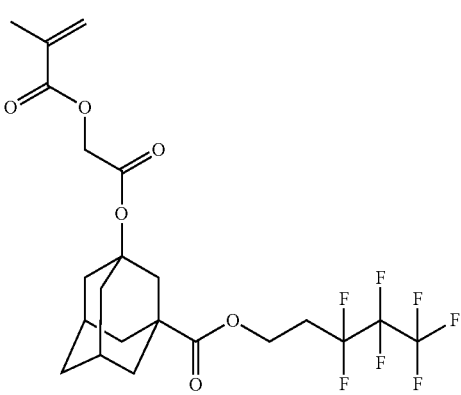
(I-7)
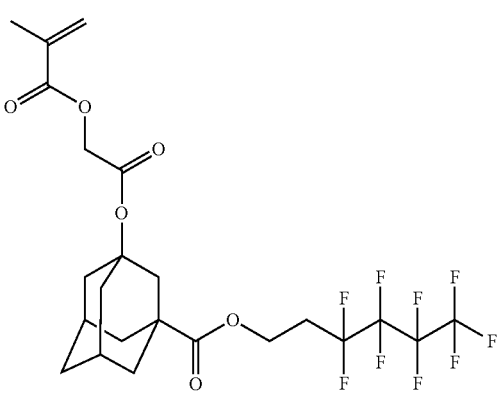
(I-8)
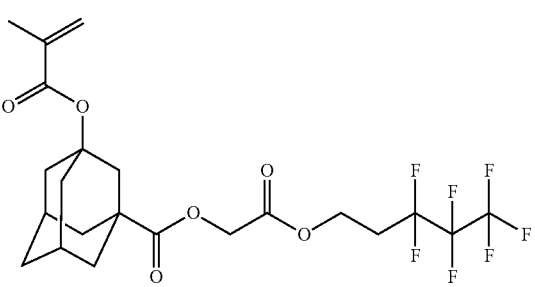
(I-9)

-continued
(I-10)
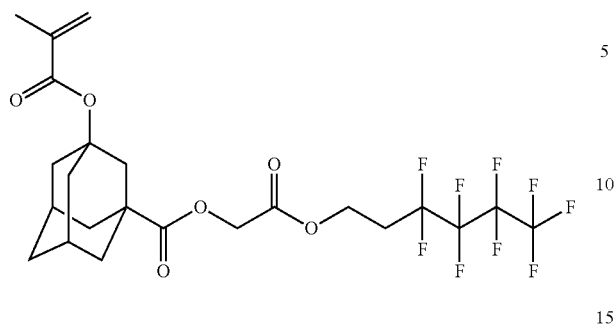
(I-11)
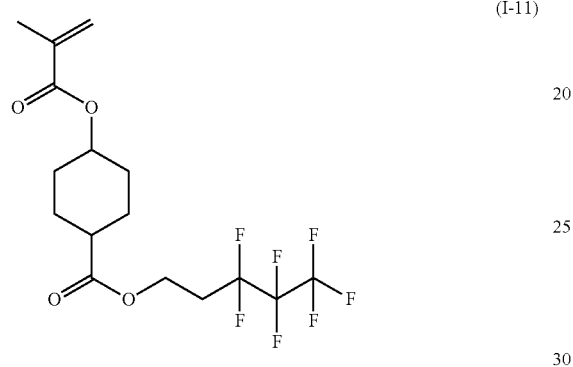
(I-12)
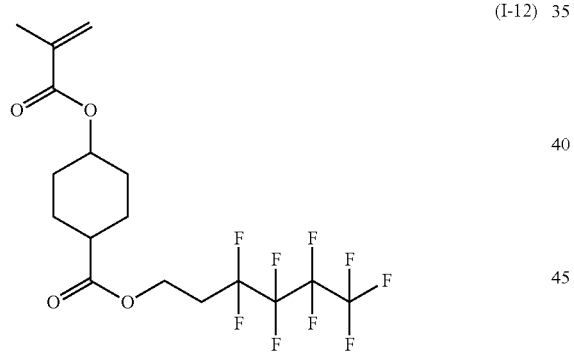
(I-13)
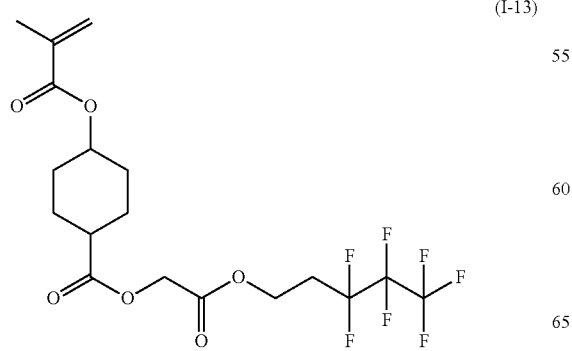
-continued
(I-14)
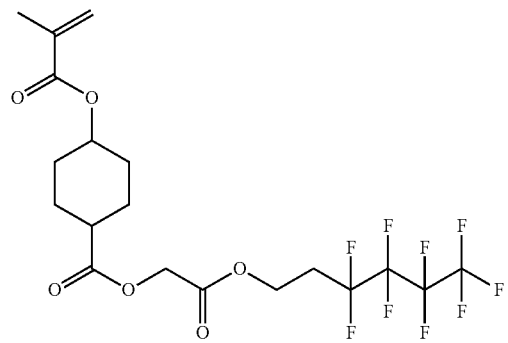
(I-15)
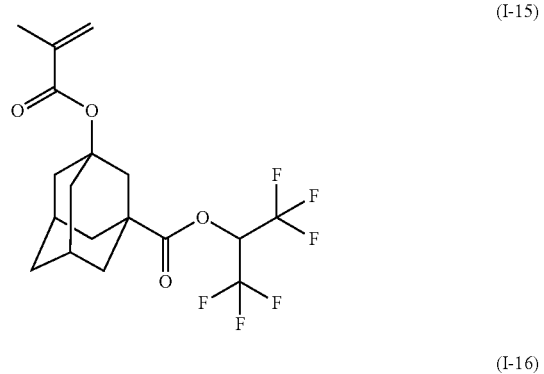
(I-16)
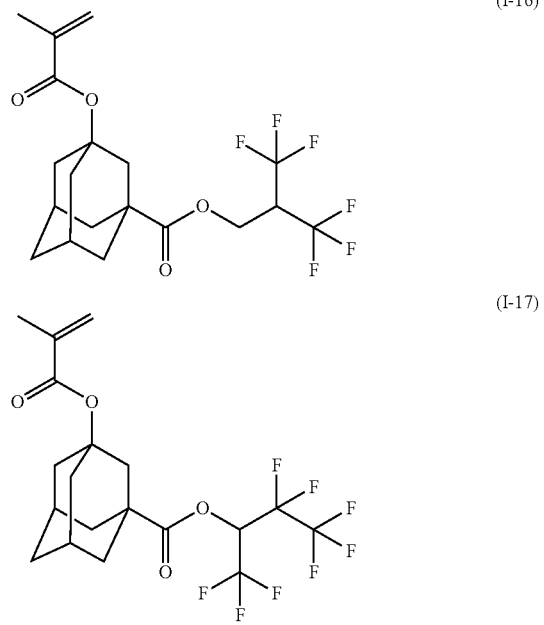
(I-17)
(I-18)
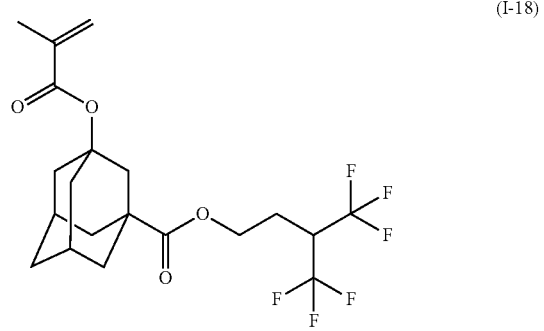

(I-19)
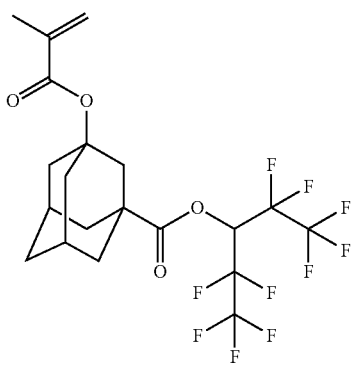

(I-20)
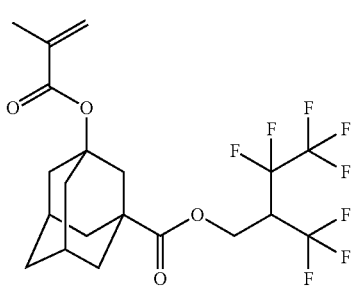

(I-21)
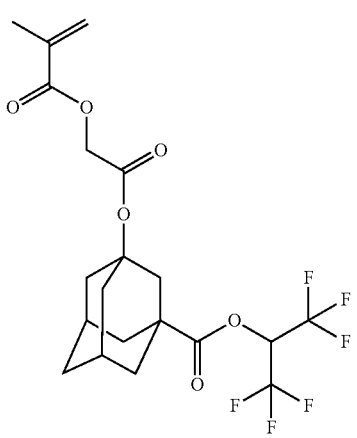

(I-22)
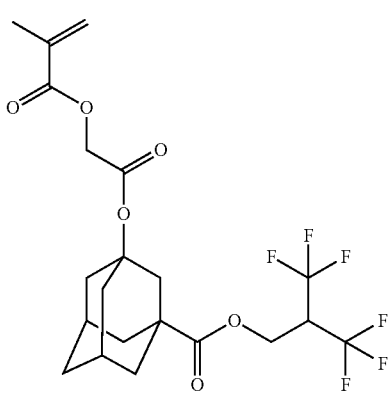

(I-23)
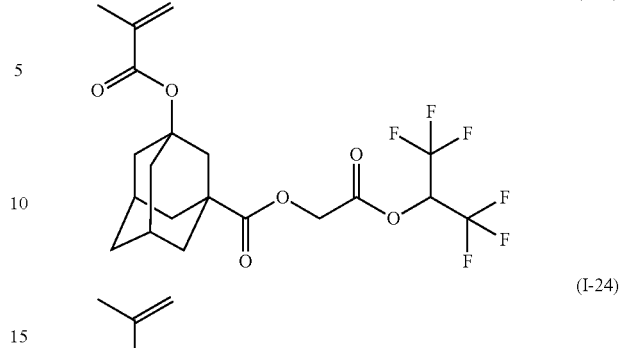

(I-24)
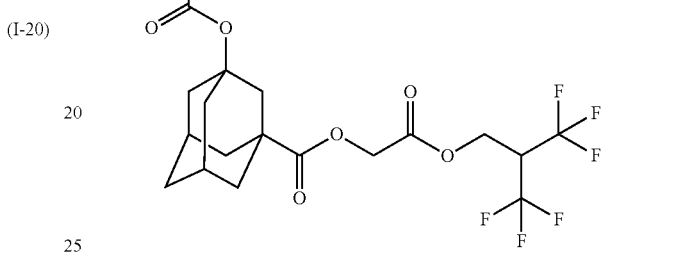

Examples of the compound (I) also include the compounds of the formulae (I-1) to (I-24) in which a methyl group corresponding to $R^1$ has been replaced by a hydrogen atom.

<Method for Producing the Compound (I)>

A method for producing the compound (I) is described below.

The compound (I) can be obtained by reacting a compound represented by the formula (I-a) with a compound represented by the formula (I-b) in presence of a catalyst in a solvent.

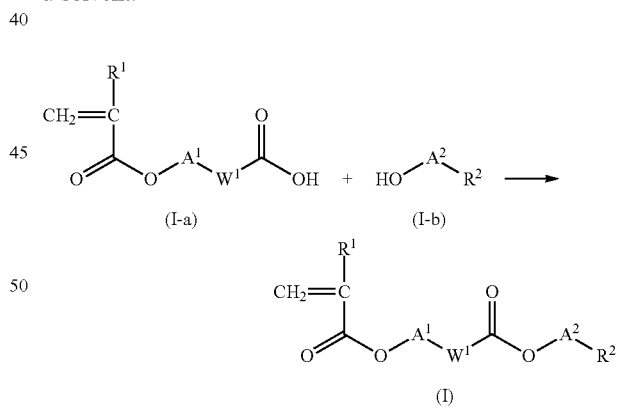

Preferred examples of the solvent include chloroform, tetrahydrofuran and toluene.

Preferred examples of the catalyst include the basic catalyst such as pyridine and dimethylaminopyridine, and a known esterified catalyst such as an acid catalyst and carbodiimide catalyst. The basic catalyst and the known esterified catalyst can be used as a catalyst for the reaction.

Examples of the compound represented by the formula (I-a) include the salt represented by the formula below which is available on the market.

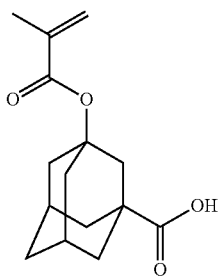 [SMILES: C=C(C)C(=O)OC12CC3CC(C1)CC(C(=O)O)(C3)C2]

Examples of the compound represented by the formula (I-b) include the salts represented by the formulae below which are available on the market.

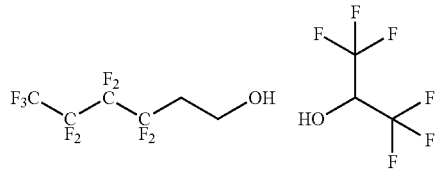 [SMILES: OCCC(F)(F)C(F)(F)C(F)(F)C(F)(F)F ; OC(C(F)(F)F)C(F)(F)F]

Examples of the carbodiimide catalyst include the salt represented by the formula below which is available on the market.

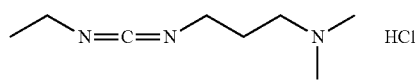

<Resin Containing a Structural Unit Derived from the Compound (I)>

The resin of the present invention is a resin having a structural unit derived from the compound (I) which structural unit is sometimes referred to as "structural unit (I)". The resin is sometimes referred to as "resin (X)".

In the resin (X), the proportion of structural unit (I) is generally 10 to 70% by mole, preferably 20 to 60% by mole, more preferably 30 to 50% by mole, with respect to the total structural units (100% by mole) of the resin (X).

In addition to the structural unit (I), the resin (X) may further includes a structural unit having a fluorine atom (which structural unit is sometimes referred to as "structural unit (a4)"), a structural unit having a non-leaving hydrocarbon group (which structural unit is sometimes referred to as "structural unit (a5)") , a structural unit having an acid-labile group (which structural unit is sometimes referred to as "structural unit (a1)"), a structural unit having no acid-labile group (which structural unit is sometimes referred to as "structural unit (s)") and a structural unit derived from another known monomer. Among these, the resin (X) preferably further includes the structural unit (a4) and/or the structural unit (a5).

<Structural Unit (a4)>

The structural unit having a halogen atom preferably has a fluorine atom.

Examples of the structural unit (a4) include the structural units represented by the formula (a4-0).

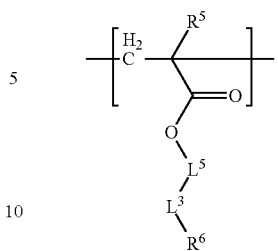

wherein $R^5$ represents a hydrogen atom or a methyl group,
$L^5$ represent a single bond or a $C_1$ to $C_4$ saturated aliphatic hydrocarbon group,
$L^3$ represents a $C_1$ to $C_8$ perfluoroalkanediyl group or a $C_5$ to $C_{12}$ perfluorocycloalkanediyl group, and
$R^6$ represents a hydrogen atom or a fluorine atom.

Examples of the saturated aliphatic hydrocarbon group of $L^5$ include a liner alkanediyl group such as methylene, ethylene, propane-1,3-diyl, butane-1,4-diyl; and a branched alkanediyl group such as a group in which a liner alkanediyl group has a side chain of an alkyl group (e.g., methyl and ethyl groups), for example, ethane-1,1-diyl, propane-1,2-diyl, butane-1,3-diyl, 2-methylpropane-1,3-diyl and 2-methylpropane-1,2-diyl groups.

Examples of the perfluoroalkanediyl group of $L^3$ include difluorolethylene, perfluoroethylene, perfluoroethyl fluoromethylene, perfluoropropane-1,3-diyl, a perfluoropropane 1,2-diyl, perfluoroproparte-2,2-diyl, perfluorobutane-1,4-diyl, perfluorobutane-2,2-diyl, perfluorobutane-1,2-diyl, perfluoropentane-1,5-diyl, perfluoropentane-2,2-diyl, perfluoropentane-3,3-diyl, perfluorohexane-1,6-diyl, perfluorohexane-2,2-diyl, perfluorohexane-3,3-diyl, perfluoroheptane-1,7-diyl, perfluoroheptane-2,2-diyl, perfluoroheptane-3,4-diyl, perfluoroheptane-4,4-diyl, perfluorooctan-1,8-diyl, perfluorooctan-2,2-diyl, perfluorooctan-3,3-diyl and perfluorooctan-4,4-diyl groups.

Examples of the perfluoro cycloalkanediyl group of $L^3$ include perfluorocyclohexanediyl, perfluorocyclopentanediyl, perfluorocycloheptanediyl and perfluoroadamantanediyl groups.

$L^5$ is preferably a single bond, methylene or ethylene group, and more preferably a single bond or methylene group.

$L^3$ is preferably a $C_1$ to $C_6$ perfluoroalkanediyl group, more preferably a $C_1$ to $C_3$ perfluoroalkanediyl group.

Examples of the structural unit (a4-0) include structural units represented by the formula (a4-0-1) to the formula (a4-0-32).

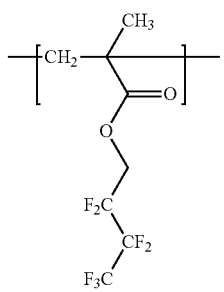

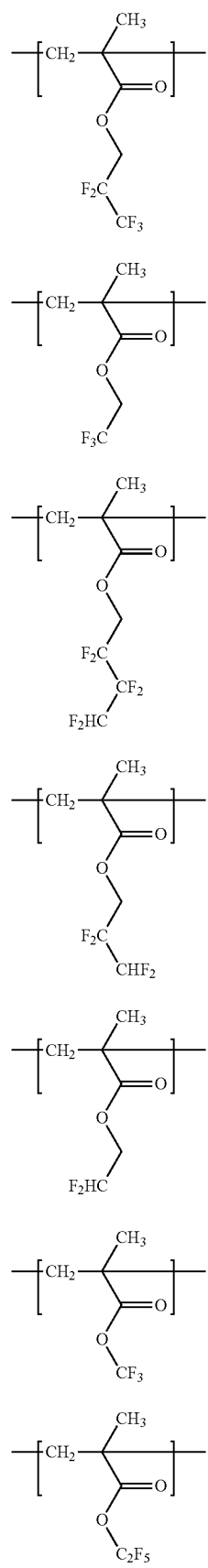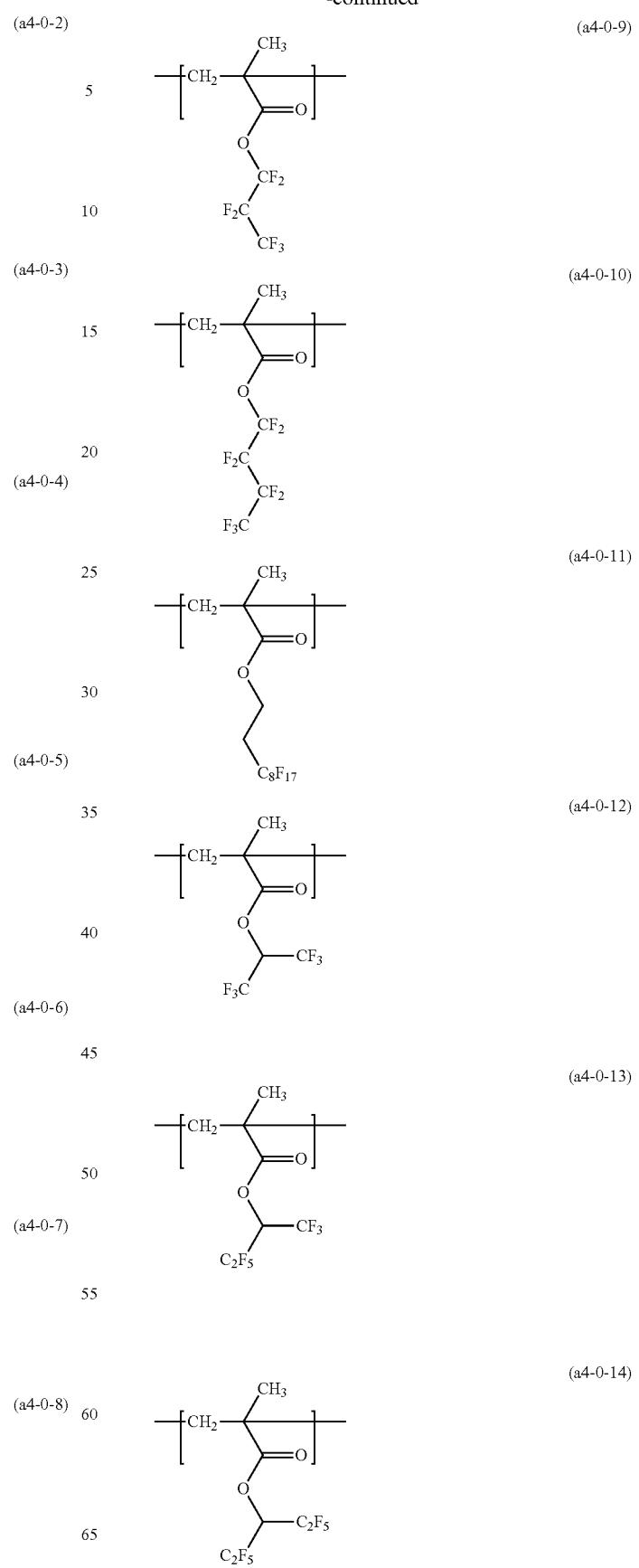

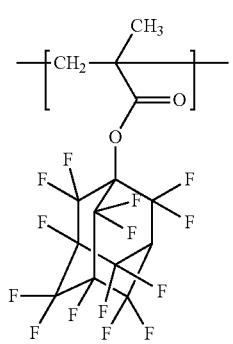 (a4-0-15)
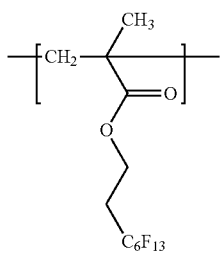 (a4-0-16)
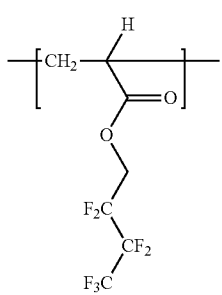 (a4-0-17)
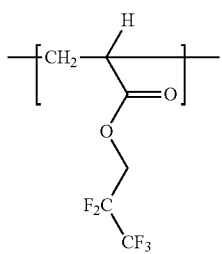 (a4-0-18)
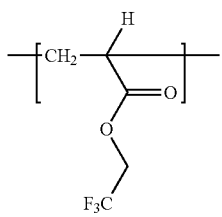 (a4-0-19)
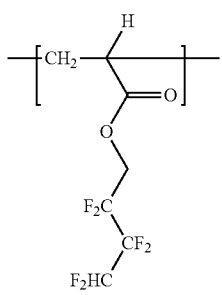 (a4-0-20)
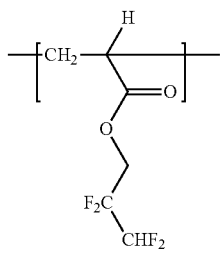 (a4-0-21)
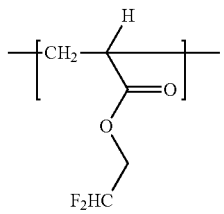 (a4-0-22)
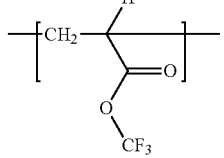 (a4-0-23)
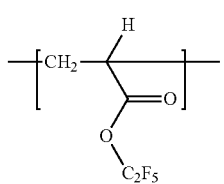 (a4-0-24)
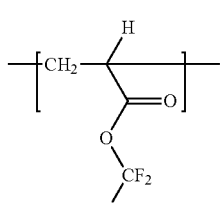 (a4-0-25)
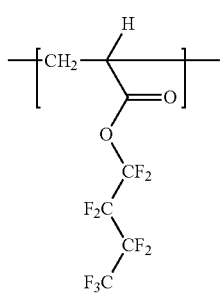 (a4-0-26)

-continued (a4-0-27)
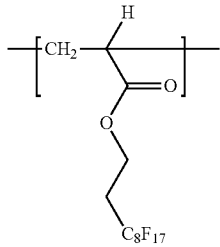

(a4-0-28)
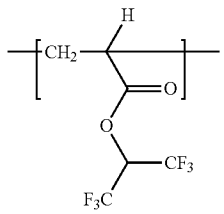

(a4-0-29)
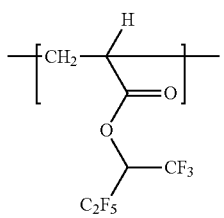

(a4-0-30)
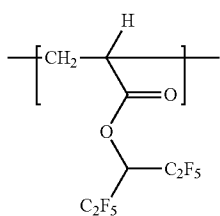

(a4-0-31)
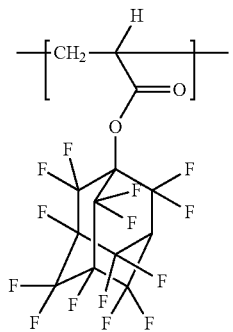

(a4-0-32)
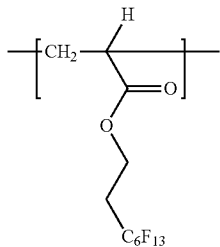

Examples of the structural unit (a4) include the structural units represented by the formula (a4-1):

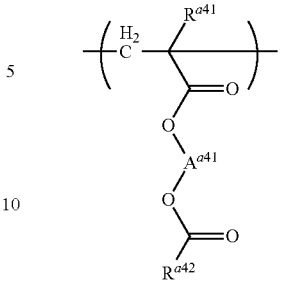
(a4-1)

wherein $R^{a41}$ represents a hydrogen atom or a methyl group,
$R^{a42}$ represents an optionally substituted $C_1$ to $C_{20}$ hydrocarbon group where a methylene group may be replaced by an oxygen atom or a carbonyl group, and
$A^{a41}$ represents an optionally substituted $C_1$ to $C_6$ alkanediyl group or a group represented by the formula (a-g1), $$—A^{a42}-(X^{a41}-A^{a43})_{\overline{s}}-X^{a42}-A^{a44}—$$ (a-g1)

wherein s represents 0 or 1,
$A^{a42}$ and $A^{a44}$ independently represent an optionally substituted $C_1$ to $C_5$ aliphatic hydrocarbon group,
$A^{a43}$ represents a single bond or an optionally substituted $C_1$ to $C_5$ aliphatic hydrocarbon group, and
$X^{a41}$ and $X^{a42}$ independently represent —O—, —CO—, —CO—O— or —O—CO—,
provided that the total carbon number contained in the group of $A^{a42}$, $A^{a43}$, $A^{a44}$, $X^{a41}$ and $X^{a42}$ is 6 or less, and
at least one of $A^{a41}$ and $R^{a42}$ has a halogen atom as a substituent, and
* and ** represent a binding site, and * represents a binding site to —O—CO—$R^{a42}$.

The hydrocarbon group of $R^{a42}$ includes a chain and a cyclic aliphatic hydrocarbon groups, an aromatic hydrocarbon group and a combination thereof.

Examples of the chain aliphatic hydrocarbon group include an alkyl group such as methyl, ethyl, n-propyl, n-butyl, n-pentyl, n-hexyl, n-heptyl, n-octyl, n-decyl, n-dodecyl, n-pentadecyl, n-hexadecyl, n-heptadecyl and n-octadecyl groups. Examples of the cyclic aliphatic hydrocarbon group include a monocyclic hydrocarbon group, i.e., cycloalkyl group such as cyclopentyl, cyclohexyl, cycloheptyl, cyclooctyl groups; and polycyclic hydrocarbon groups such as decahydronaphtyl, adamantyl and norbornyl groups as well as groups below. * represents a binding site.

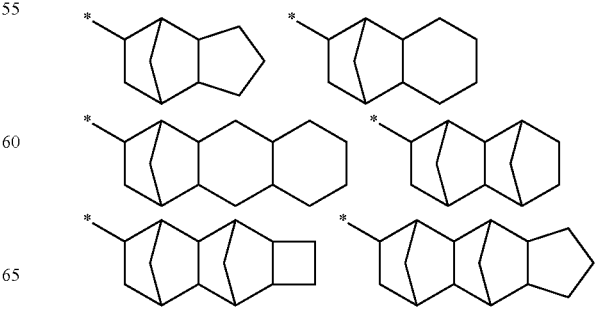

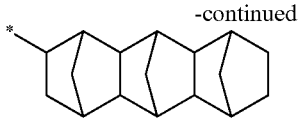

Examples of the aromatic hydrocarbon group include an aryl group such as phenyl, naphthyl, anthryl, biphenyl, phenanthryl and fluorenyl groups.

The hydrocarbon group of $R^{a42}$ is preferably a chain and a cyclic aliphatic hydrocarbon groups, and a combination thereof. The hydrocarbon group may have a carbon-carbon unsaturated bond, is preferably a chain and a cyclic saturated aliphatic hydrocarbon groups, and a combination thereof.

Examples of the substituent of $R^{a42}$ include a fluorine atom or a group represented by the formula (a-g3).

Examples of the halogen atom include fluorine, chlorine, bromine or iodine atom, and preferably a fluorine atom.

$$*-X^{a43}-A^{a45} \quad \text{(a-g3)}$$

wherein $X^{a43}$ represent an oxygen atom, a carbonyl group, a carbonyloxy group or an oxycarbonyl group.

$A^{a45}$ represents a $C_1$ to $C_{17}$ aliphatic hydrocarbon group that has a halogen atom, and

* represents a binding site to carbonyl group.

Examples of the aliphatic hydrocarbon group of $A^{a45}$ are the same examples as the group of $R^{a42}$.

$R^{a42}$ is preferably an aliphatic hydrocarbon group that may have a halogen atom, and more preferably an alkyl group having a halogen atom and/or an aliphatic hydrocarbon group having the group represented by the formula (a-g3).

When $R^{a42}$ is an aliphatic hydrocarbon group having a halogen atom, an aliphatic hydrocarbon group having a fluorine atom is preferred, a perfluoroalkyl group or a perfulorocycloalkyl group are more preferred, a $C_1$ to $C_6$ perfluoroalkyl group is still more preferred, a $C_1$ to $C_3$ perfluoroalkyl group is particularly preferred.

Examples of the perfluoroalkyl group include perfluoromethyl, perfluoroethyl, perfluoropropyl, perfluorobutyl, perfluoropentyl, perfluorohexyl, perfluoroheptyl and perfluorooctyl groups. Examples of the perfluorocycloalkyl group include perfluorocyclohexyl group.

When $R^{a42}$ is an aliphatic hydrocarbon group having the group represented by the formula (a-g3), the total carbon number contained in the aliphatic hydrocarbon group including the group represented by the formula (a-g3) is preferably 15 or less, more preferably 12 or less. The number of the group represented by the formula (a-g3) is preferably one when the group represented by the formula (a-g3) is the substituent.

The aliphatic hydrocarbon having the group represented by the formula (a-g3) is more preferably a group represented by the formula (a-g2);

$$*-A^{a46}-X^{a44}-A^{a47} \quad \text{(a-g2)}$$

wherein $A^{a46}$ represents a $C_1$ to $C_{17}$ aliphatic hydrocarbon group that may have a halogen atom, $X^{a44}$ represent a carbonyloxy group or an oxycarbonyl group, $A^{a47}$ represents a $C_1$ to $C_{17}$ aliphatic hydrocarbon group that may have a halogen atom, provided that the total carbon number contained in the group of $A^{a46}$, $X^{a44}$ and $A^{a47}$ is 18 or less, at least one of $A^{a46}$ and $A^{a47}$ has a halogen atom, and

* represents a binding site to carbonyl group.

The carbon number of the aliphatic hydrocarbon group of $A^{a46}$ is preferably 1 to 6, and more preferably 1 to 3.

The carbon number of the aliphatic hydrocarbon group of $A^{a47}$ is preferably 4 to 15, and more preferably 5 to 12, and cyclohexyl and adamantyl groups are still more preferred as the aliphatic hydrocarbon group.

Preferred structure represented by the formula (a-g2), $*-A^{a46}-X^{a44}-A^{a47}$, include the following ones.

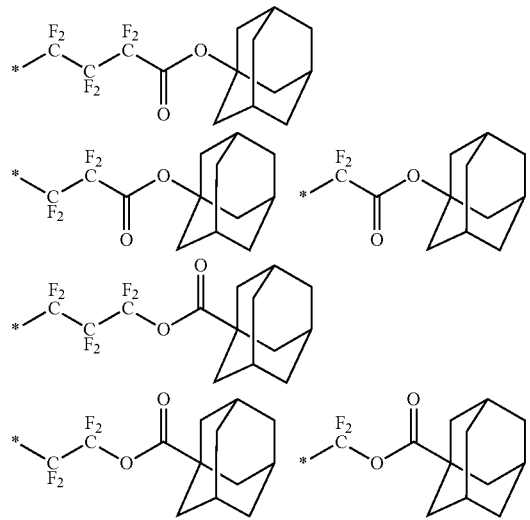

[0038]

Examples of the alkanediyl group of $A^{a41}$ include a liner alkanediyl group such as methylene, ethylene, propane-1,3-diyl, butane-1,4-diyl, pentane-1,5-diyl and hexane-1,6-diyl groups;

a branched alkanediyl group such as propane-1,2-diyl, butan-1,3-diyl, 2-methylpropane-1,2-diyl, 1-methylpropane-1,4-diyl, 2-methylbutane-1,4-diyl groups.

Examples of the substituent of the alkanediyl group of $A^{a41}$ include a hydroxy group and a $C_1$ to $C_6$ alkoxy group.

$A^{a41}$ is preferably a $C_1$ to $C_4$ alkanediyl group, more preferably a $C_2$ to $C_4$ alkanediyl group, and still more preferably ethylene group.

In the group represented by the formula (a-g1) (which is sometimes referred to as "group (a-g1)"), examples of the aliphatic hydrocarbon group of $A^{a42}$, $A^{a43}$ and $A^{a44}$ include methylene, ethylene, propane-1,3-diyl, propane-1,2-diyl, butane-1,4-diyl, 1-methylpropane-1,3-diyl, 2-methylpropane-1,3-diyl and 2-methylpropane-1,2-diyl groups.

Examples of the substituent of the aliphatic hydrocarbon group of $A^{a42}$, $A^{a43}$ and $A^{a44}$ include a hydroxy group and a $C_1$ to $C_6$ alkoxy group.

s is preferably 0.

Examples of the group (a-g1) in which $X^{a42}$ represents an oxygen atom include the following ones. In the formula, * and  each represent a binding site, and  represents a binding site to $-O-CO-R^{a42}$.

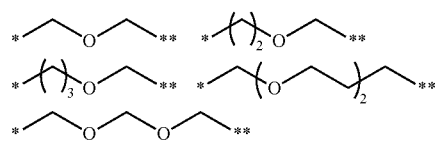

Examples of the group (a-g1) in which $X^{a42}$ represents a carbonyl group include the following ones.

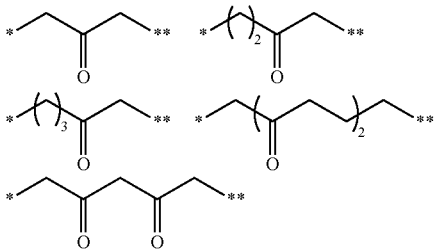

Examples of the group (a-g1) in which $X^{a42}$ represents a carbonyloxy group include the following ones.

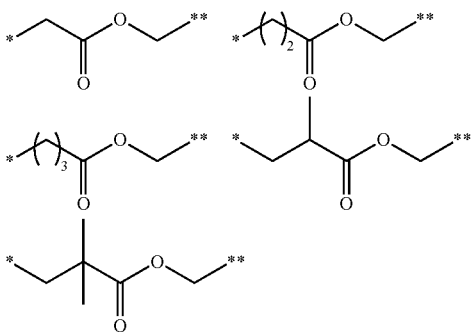

Examples of the group (a-g1) in which $X^{a42}$ represents an oxycarbonyl group include the following ones.

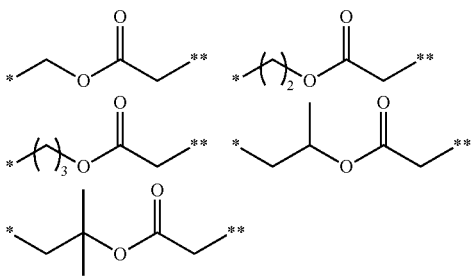

The structural unit represented by the formula (a4-1) is preferably structural units represented by the formula (a4-2) and the formula (a4-3):

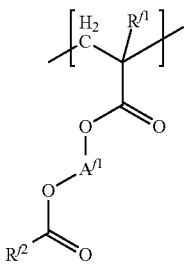
(a4-2)

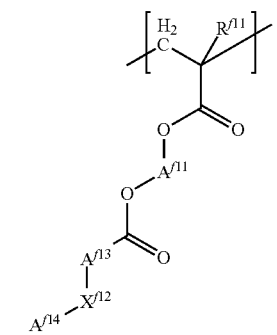
(a4-3)

wherein $R^{f1}$ represents a hydrogen atom or a methyl group, $A^{f1}$ represent a $C_1$ to $C_6$ alkanediyl group, and $Rf^2$ represents a $C_1$ to $C_{10}$ hydrocarbon group that has a fluorine atom.

Examples of the alkanediyl group of $A^{f1}$ include a chain alkanediyl group such as methylene, ethylene, propane-1,3-diyl, butane-1,4-diyl, pentane-1,5-diyl and hexane-1,6-diyl groups;

a branched alkanediyl group such as 1-methylpropane-1,3-diyl, 2-methylpropane-1,3-diyl, 2-methylpropane-1,2-diyl, 1-methylbutanel, 1,4-diyl and 2-methylbutane-1,4-diyl groups.

The hydrocarbon group of $R^{f2}$ includes an aliphatic hydrocarbon group and an aromatic hydrocarbon group. The aliphatic hydrocarbon group includes a chain and a cyclic groups, and a combination thereof. The aliphatic hydrocarbon group is preferably an alkyl group and an alicyclic hydrocarbon group.

Examples of the alkyl group include methyl, ethyl, n-propyl, isopropyl, n-butyl, sec-butyl, tert-butyl, n-pentyl, n-hexyl, n-heptyl, n-octyl and 2-ethylhexyl groups.

Examples of the alicyclic hydrocarbon group include any of a monocyclic group and a polycyclic group. Examples of the monocyclic alicyclic hydrocarbon group include a cycloalkyl group such as cyclopropyl, cyclobutyl, cyclopentyl, cyclohexyl, cycloheptyl, cyclooctyl, and cyclodecyl groups. Examples of the polycyclic hydrocarbon groups includes decahydronaphthyl, adamantyl, 2-alkyladamantane-2-yl, 1-(adamantane-1-yl) alkane-1-yl, norbornyl, methylnorbornyl and isobornyl groups.

Examples of the hydrocarbon group having a fluorine atom of $R^{f2}$ include an alkyl group having a fluorine atom and an alicyclic hydrocarbon group having a fluorine atom.

Specific examples of an alkyl group having a fluorine atom include a fluorinated alkyl group such as difluoromethyl, trifluoromethyl, 1,1-difluoroethyl, 2,2-difluoroethyl, 2,2,2-trifluoroethyl, perfluoroethyl, 1,1,2,2-tetrafluoropropyl, 1,1,2,2,3,3-hexafluoropropyl, perfluoroethylmethyl, 1-(trifluoromethyl)-1,2,2,2-tetrafluoroethyl, perfluoropropyl, 1,1,2,2-tetrafluorobutyl, 1,1,2,2,3,3-hexafluorobutyl, 1,1,2,2,3,3,4,4-octafluorobutyl, perfluorobutyl, 1,1-bis(trifluoromethyl)methyl-2,2,2-trifluoroethyl, 2-(perfluoropropyl)ethyl, 1,1,2,2,3,3,4,4-octafluoropentyl, perfluoropentyl, 1,1,2,2,3,3,4,4,5,5-decafluoro pentyl, 1,1-bis(trifluoromethyl)2,2,3,3,3-pentafluoropropyl, perfluoropentyl, 2-(perfluorobutyl)ethyl, 1,1,2,2,3,3,4,4,5,5-decafluorohexyl, 1,1,2,2,3,3,4,4,5,5,6,6-dodeca fluorohexyl, perfluoropentylmethyl and perfluorohexyl groups.

Examples of the alicyclic hydrocarbon group having a fluorine atom include a fluorinated cycloalkyl group such as perfluorocyclohexyl and perfluoroadamantyl groups.

In the formula (a4-2), $A^{f1}$ is preferably a $C_2$ to $C_4$ alkanediyl group, and more preferably ethylene group.

$R^{f2}$ is preferably a $C_1$ to $C_6$ fluorinated alkyl group:

wherein $R^{f11}$ represents a hydrogen atom or a methyl group, $A^{f11}$ represent a $C_1$ to $C_6$ alkanediyl group, $A^{f13}$ represents a $C_1$ to $C_{18}$ aliphatic hydrocarbon group that may has a fluorine atom, $A^{f12}$ represents an oxycarbonyl group or a carbonyloxy group, $A^{f14}$ represents a $C_1$ to $C_{17}$ aliphatic hydrocarbon group that may has a fluorine atom, and provided that at least one of $A^{f13}$ and $A^{f14}$ represents an aliphatic hydrocarbon group having a fluorine atom.

Examples of the alkanediyl group of $A^{f11}$ are the same examples as the alkanediyl group of $A^{f1}$.

Examples of the aliphatic hydrocarbon group of $A^{f13}$ include any of a divalent chain or cyclic hydrocarbon group, or a combination thereof. The aliphatic hydrocarbon group may have a carbon-carbon unsaturated bond, and is preferably a saturated aliphatic hydrocarbon group.

The aliphatic hydrocarbon group that may has a fluorine atom of $A^{f13}$ is the saturated aliphatic hydrocarbon group that may has a fluorine atom, and preferably a perfuloroalkandiyl group.

Examples of the divalent chain aliphatic hydrocarbon that may have a fluorine atom include an alkanediyl group such as methylene, ethylene, propanediyl, butanediyl and pentanediyl groups; a perfluoroalkanediyl group such as difluoromethylene, perfluoroethylene, perfluoropropanediyl, perfluorobutanediyl and perfluoropentanediyl groups.

The divalent cyclic aliphatic hydrocarbon group that may have a fluorine atom is any of monocyclic or polycyclic group.

Examples monocyclic aliphatic hydrocarbon group include cyclohexanediyl and perfluorocyclohexanediyl groups.

Examples polycyclic aliphatic hydrocarbon group include adamantanediyl, norbornanediyl, and perfluoroadamantanediyl groups.

Examples of the aliphatic hydrocarbon group of $A^{f14}$ include any of a chain or a cyclic hydrocarbon group, or a combination thereof. The aliphatic hydrocarbon group may have a carbon-carbon unsaturated bond, and is preferably a saturated aliphatic hydrocarbon group.

The aliphatic hydrocarbon group that may has a fluorine atom of $A^{f14}$ is preferably the saturated aliphatic hydrocarbon group that may have a fluorine atom.

Examples of the chain aliphatic hydrocarbon group that may have a halogen atom include trifluoromethyl, difluoromethyl, methyl, perfluoromethyl, 1,1,1-trifluoroethyl, 1,1,2,2-tetrafluoroethyl, ethyl, perfluoropropyl, 1,1,1,2,2-pentafluoropropyl, propyl, perfluorobutyl, 1,1,2,2,3,3,4,4-octafluorobutyl, butyl, perfluoropentyl, 1,1,1,2,2,3,3,4,4-nonafluoropentyl, pentyl, hexyl, perfluorohexyl, hepthyl, perfluoroheptyl, octyl and perfluorooctyl groups.

The cyclic aliphatic hydrocarbon group that may have a halogen atom is any of monocyclic or polycyclic group. Examples of the group containing the monocyclic aliphatic hydrocarbon group includes cyclopropylmethyl, cyclopropyl, cyclobutylmethyl, cyclopentyl, cyclohexyl and perfluorocyclohexyl groups. Examples of the group containing the polycyclic aliphatic hydrocarbon group includes adamantyl, adamantylmethyl, norbornyl, norbornylmethyl, pertfluoroadamantyl and perfluoroadamantylmethyl groups In the formula (a4-3), $A^{f11}$ is preferably ethylene group.

The aliphatic hydrocarbon group of $A^{f13}$ is preferably a $C_1$ to $C_6$ aliphatic hydrocarbon group, more preferably a $C_2$ to $C_3$ aliphatic hydrocarbon group.

The aliphatic hydrocarbon group of $A^{f14}$ is preferably a $C_3$ to $C_{12}$ aliphatic hydrocarbon group, more preferably a $C_3$ to $C_{10}$ aliphatic hydrocarbon group. Among these, $A^{f14}$ is preferably a group containing a $C_3$ to $C_{12}$ alicyclic hydrocarbon group, more preferably cyclopropylmethyl, cyclopentyl, cyclohexyl, norbornyl and adamantyl group.

Examples of the structural unit (a4-2) include structural units represented by the formula (a4-1-1) to the formula (a4-1-22).

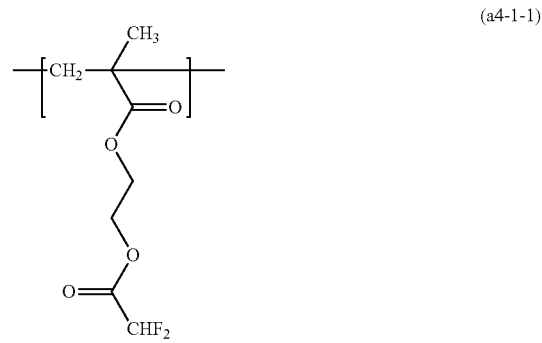

(a4-1-1)

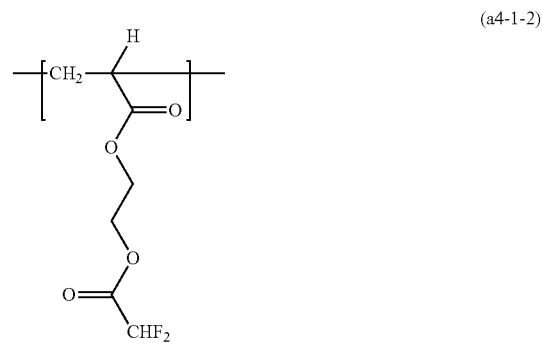

(a4-1-2)

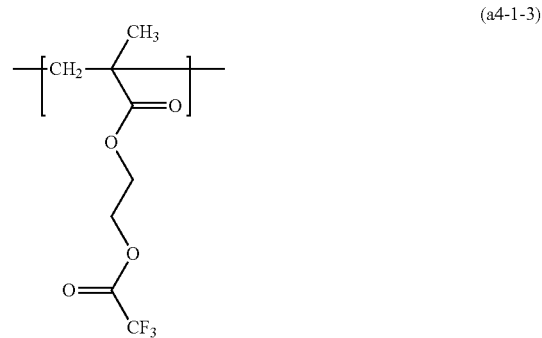

(a4-1-3)

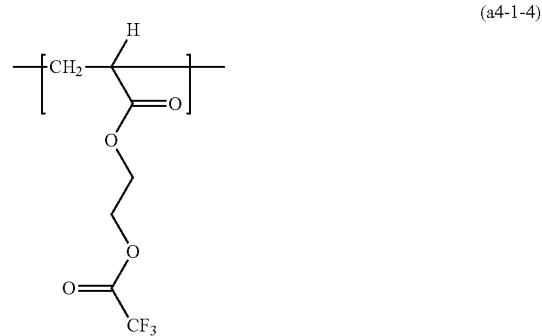

(a4-1-4)

(a4-1-5)
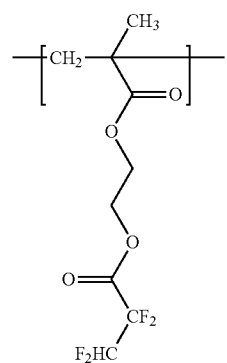
(a4-1-6)
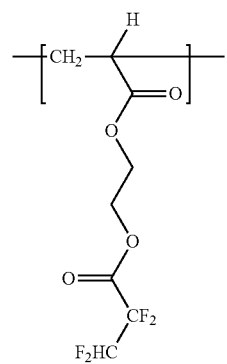
(a4-1-7)
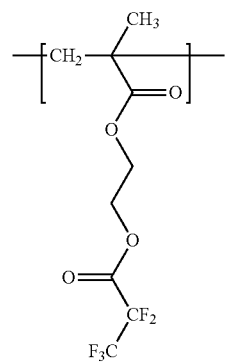
(a4-1-8)
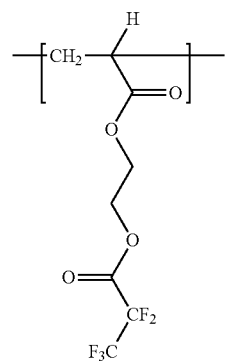
(a4-1-9)
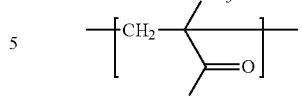
(a4-1-10)
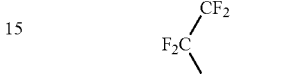
(a4-1-11)
(a4-1-12)

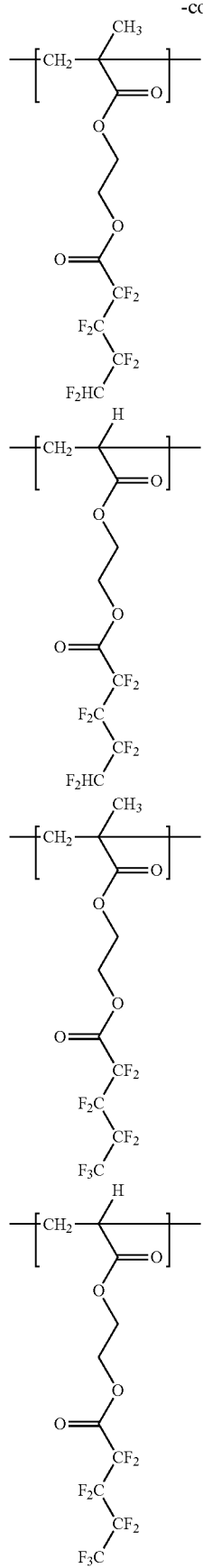
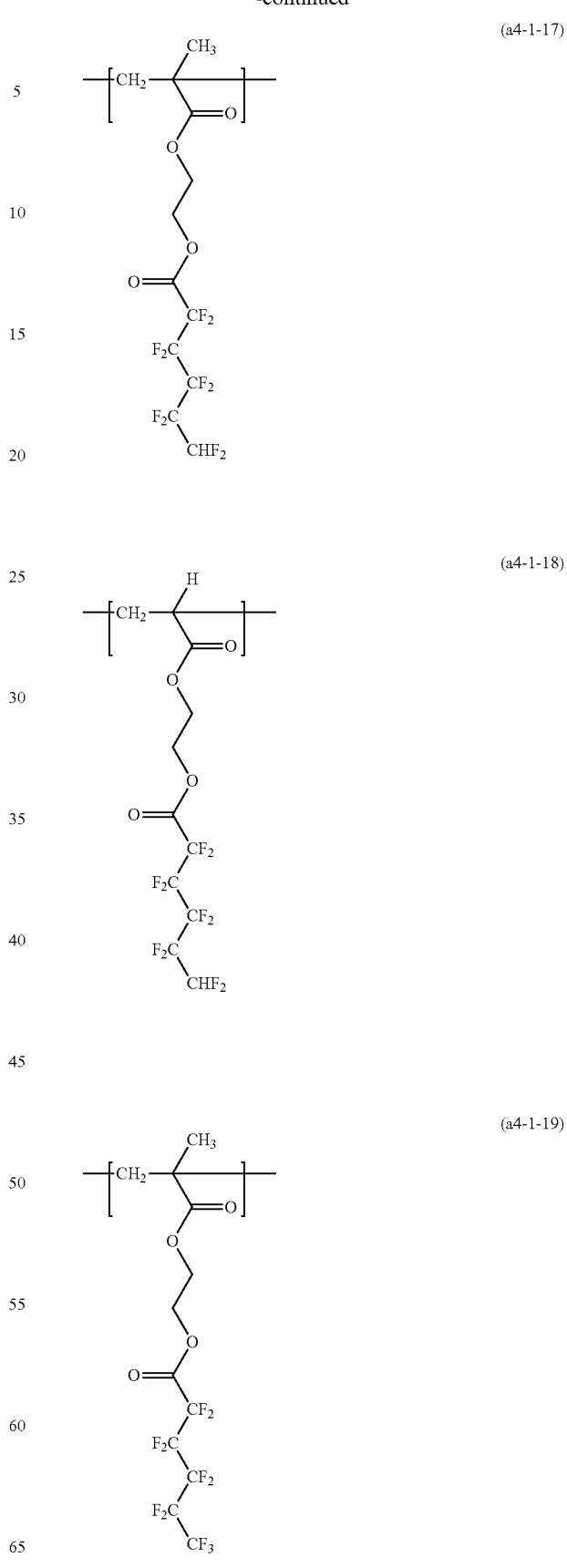

(a4-1-20)
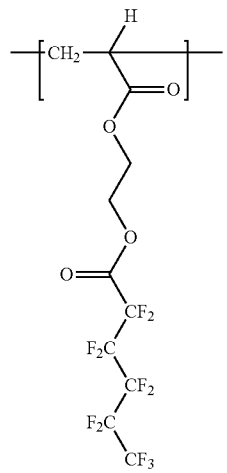
(a4-1'-1)
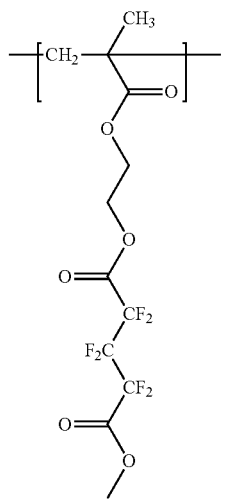
(a4-1-21)
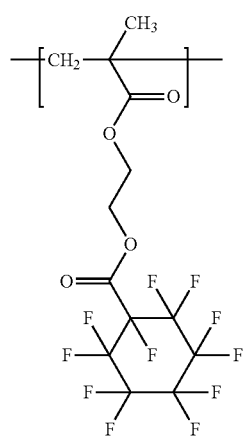
(a4-1'-2)
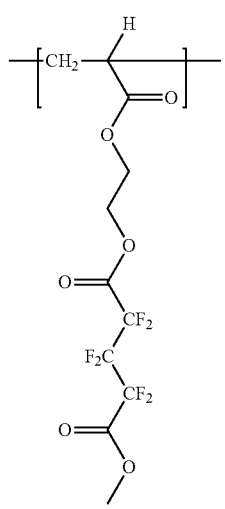
(a4-1-22)
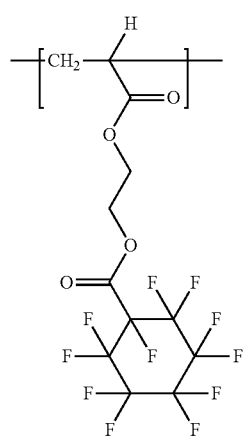
(a4-1'-3)
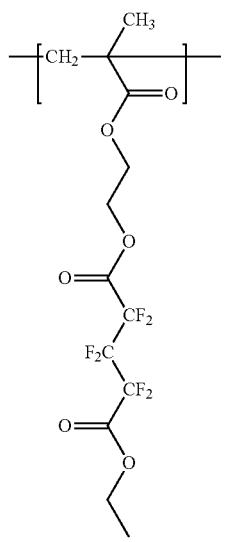
Examples of the structural unit (a4-3) include structural units presented by the formula (a4-1'-1) to the formula (A4-1'-22).

(a4-1'-4)
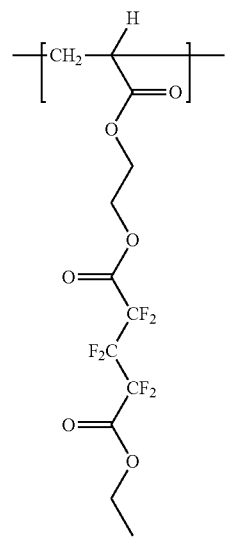
(a4-1'-5)
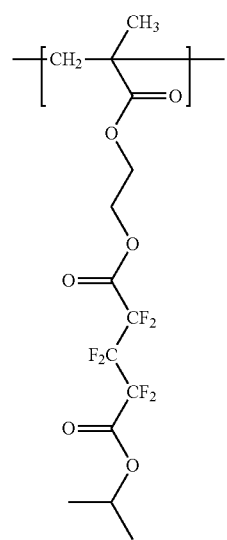
(a4-1'-6)
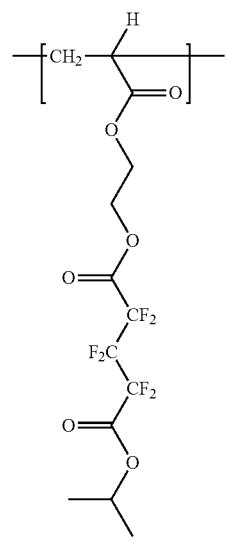
(a4-1'-7)
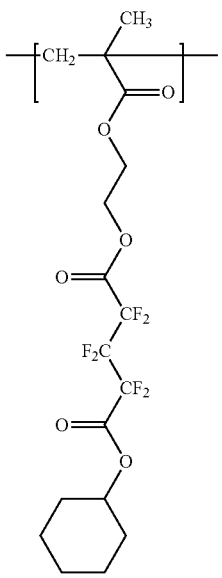
(a4-1'-8)
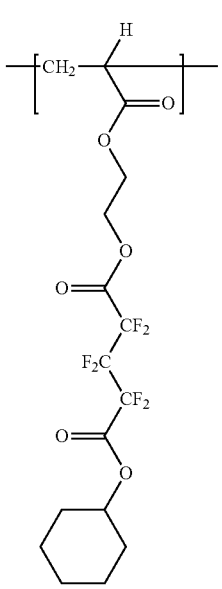

(a4-1'-9)
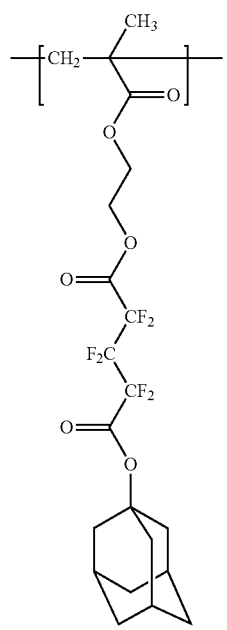
(a4-1'-10)
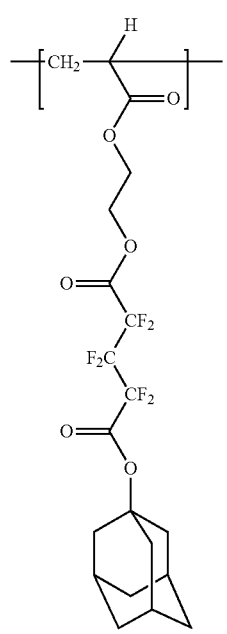
(a4-1'-11)
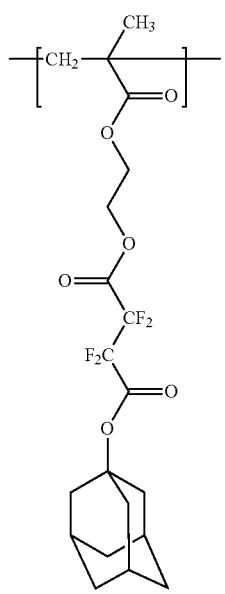
(a4-1'-12)
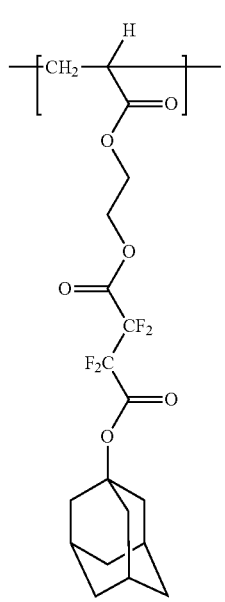

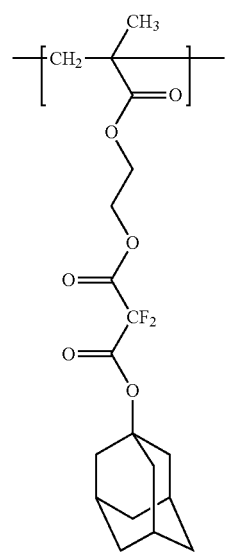
(a4-1'-13)
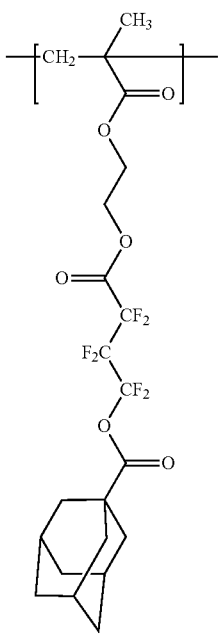
(a4-1'-15)
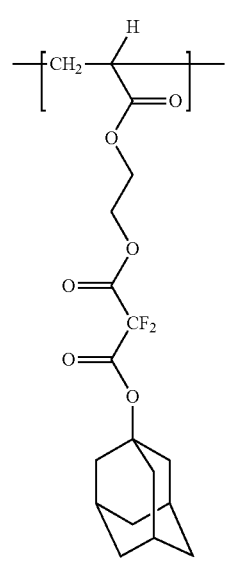
(a4-1'-14)
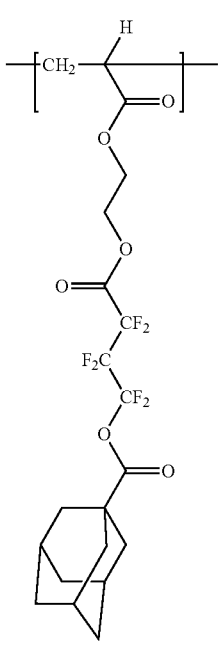
(a4-1'-16)

(a4-1'-17)
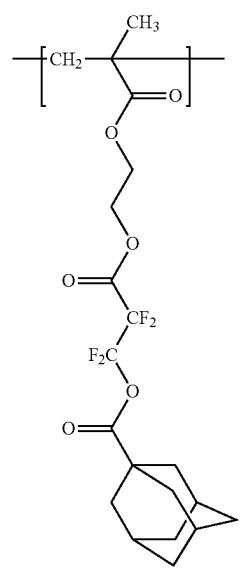
(a4-1'-18)
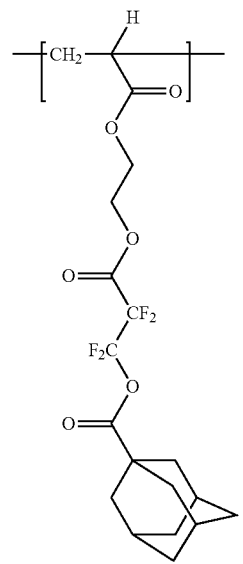
(a4-1'-19)
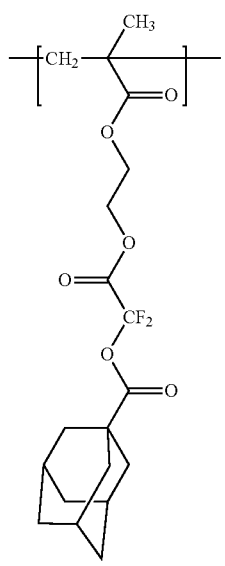
(a4-1'-20)
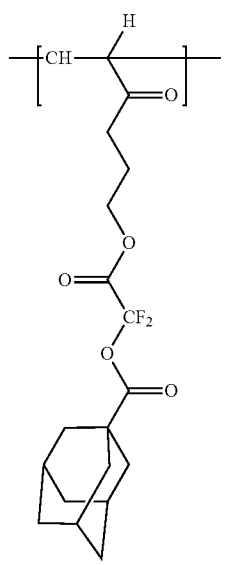
(a4-1'-21)
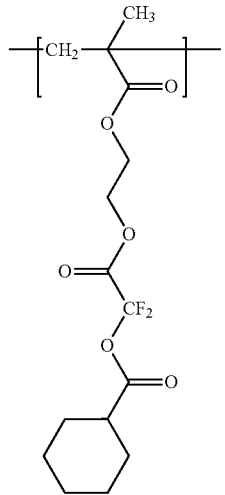

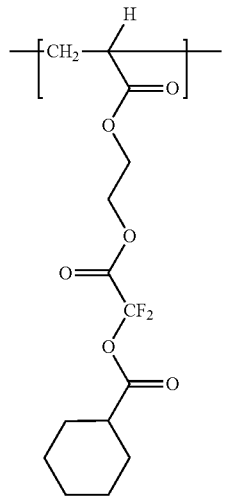

(a4-1′-22)

Examples of the structural unit (a4) include a structural unit presented by the formula (a4-4):

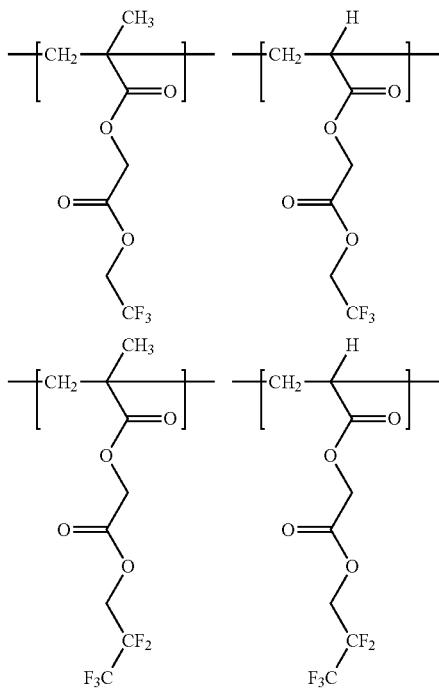

(a4-4)

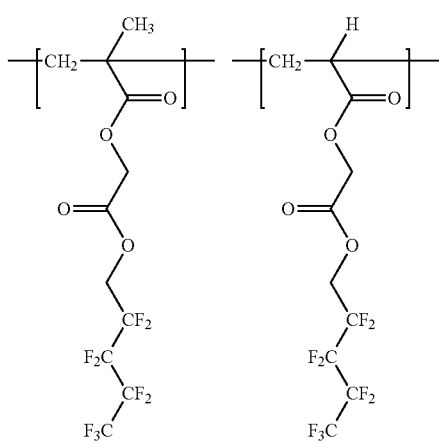

wherein $R^{f21}$ represents a hydrogen atom or a methyl group, $A^{f21}$ represents —$(CH_2)_{j1}$—, —$(CH_2)_{j2}$—O—$(CH_2)_{j3}$— or —$(CH_2)_{j4}$—CO—CO—O—$(CH_2)_{j5}$—, j1 to j5 independently represents an integer of 1 to 6, and $R^{f22}$ represents a $C_1$ to $C_{10}$ hydrocarbon group having a fluorine atom.

Examples of the hydrocarbon group having a fluorine atom of $R^{f22}$ are the same examples as the hydrocarbon group described in $R^{f2}$ in the formula (a4-2). $R^{f22}$ is preferably a $C_1$ to $C_{10}$ alkyl having a fluorine atom or a $C_3$ to $C_{10}$ alicyclic hydrocarbon group having a fluorine atom, more preferably a $C_1$ to $C_{10}$ alkyl having a fluorine atom, and still more preferably a $C_1$ to $C_6$ alkyl having a fluorine atom.

In the formula (a4-4), $A^{f21}$ is preferably —$(CH_2)_{j1}$—, more preferably methylene or ethylene group, and still more preferably methylene group.

Examples of the structural unit represented by the formula (a4-4) include the following ones.

-continued
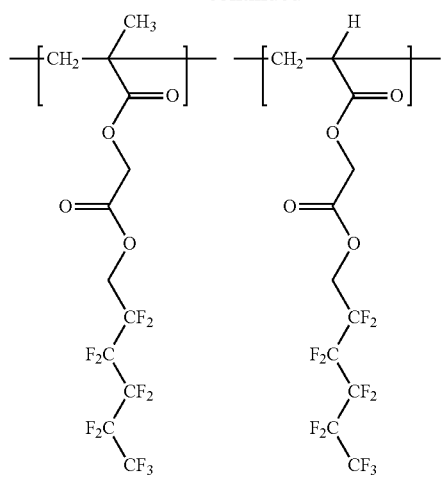
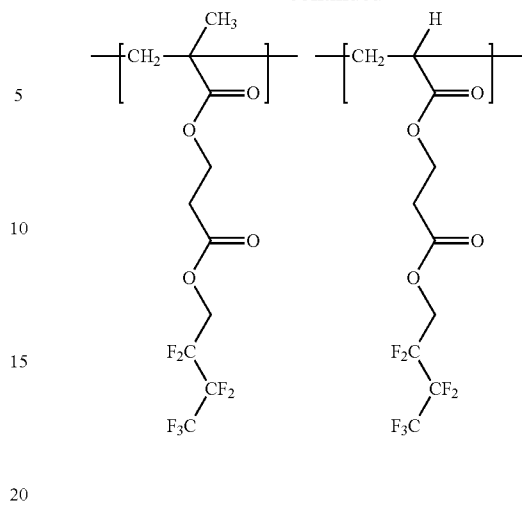
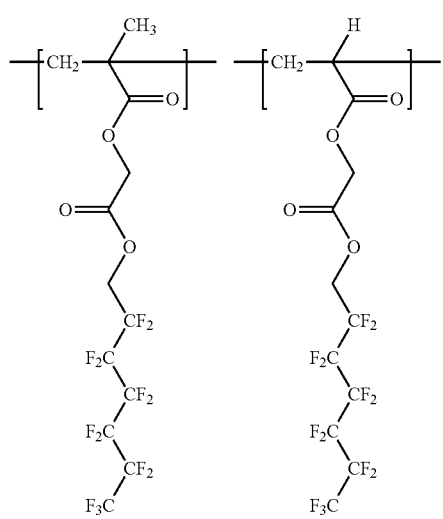
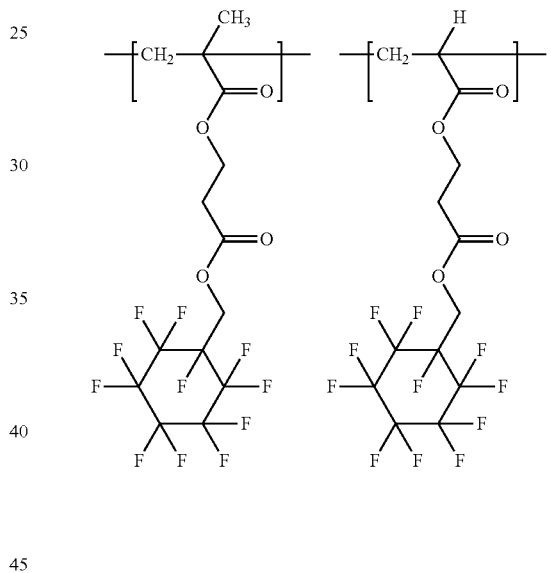
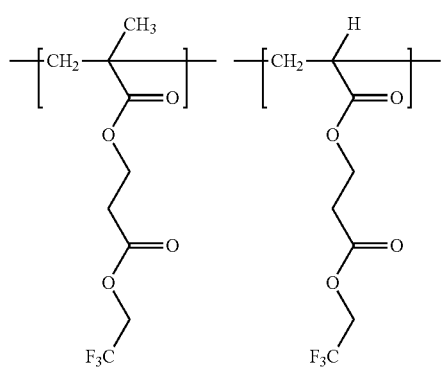
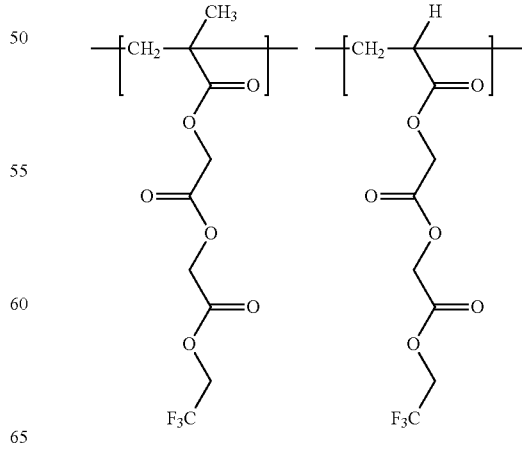

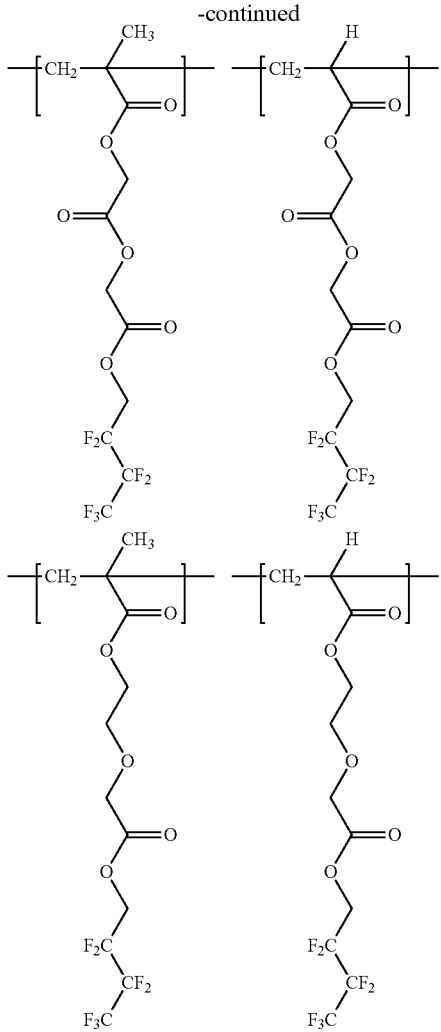

When the resin (X) contains the structural unit (a4), the proportion thereof is generally 1 to 20% by mole, preferably 2 to 15% by mole, more preferably 3 to 10% by mole, with respect to the total structural units (100% by mole) of the resin (X).

<Structural Unit (a5)>

Examples of the non-leaving hydrocarbon group in the structural unit (a5) include a chain, a branched or a cyclic hydrocarbon group. Among these, the structural unit (a5) is preferably a structural unit containing an alicyclic hydrocarbon group.

The structural unit (a5) is, for example, a structural unit represented by the formula (a5-1):

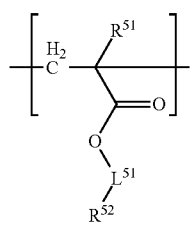
(a5-1)

wherein $R^{51}$ represents a hydrogen atom or a methyl group, $R^{52}$ represents a $C_3$ to $C_{18}$ alicyclic hydrocarbon group where a hydrogen atom may be replaced by a $C_1$ to $C_8$ aliphatic hydrocarbon group or a hydroxy group, provided that a hydrogen atom contained in the carbon atom bonded to $L^{51}$ is not replaced by the $C_1$ to $C_8$ aliphatic hydrocarbon group, and $L^{51}$ represents a single bond or a $C_1$ to $C_{18}$ divalent saturated hydrocarbon group where a methylene group may be replaced by an oxygen atom or a carbonyl group.

Examples of the alicyclic hydrocarbon group of $R^{52}$ include any one of a monocyclic group or a polycyclic group. Examples of the monocyclic alicyclic hydrocarbon group include cyclopropyl, cyclobutyl, cyclopentyl and cyclohexyl groups. Examples of the polycyclic hydrocarbon group include adamantyl and norbornyl groups.

Examples of the $C_1$ to $C_8$ aliphatic hydrocarbon group include an alkyl group such as methyl, ethyl, n-propyl, isopropyl, n-butyl, sec-butyl, tert-butyl, n-pentyl, n-hexyl, n-heptyl, 2-ethylhexyl and n-octyl groups.

Examples of the alicyclic hydrocarbon group having a substituent include 3-hydroxyadamantyl and 3-methyladamantyl.

$R^{52}$ is preferably an unsubstituted $C_3$ to $C_{18}$ alicyclic hydrocarbon group, and more preferably adamantyl, norbornyl and cyclohexyl groups.

Examples of the divalent saturated hydrocarbon group of $L^{51}$ include a divalent aliphatic saturated hydrocarbon group and a divalent alicyclic saturated hydrocarbon group, and a divalent aliphatic saturated hydrocarbon group is preferred.

Examples of the divalent aliphatic saturated hydrocarbon group include an alkanediyl such as methylene, ethylene, propanediyl, butanediyl and pentanediyl.

Examples of the divalent alicyclic saturated hydrocarbon group include any of a monocyclic group and a polycyclic group. Examples of the monocyclic alicyclic saturated hydrocarbon groups include cycloalkanediyl such as cyclopentanediyl and cyclohexanediyl groups. Examples of the polycyclic saturated hydrocarbon groups include adamantanediyl and norbornanediyl groups.

Examples of the group in which a methylene group contained in the saturated hydrocarbon group is replaced by an oxygen atom or a carbonyl group include groups represented by the formula (L1-1) to the formula (L1-4). In the formula (L1-1) to the formula (L1-4), * represents a binding site to an oxygen atom.

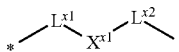
(L1-1)

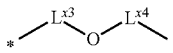
(L1-2)

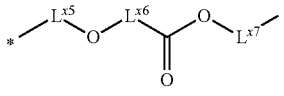
(L1-3)

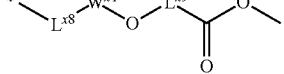
(L1-4)

wherein $X^{X1}$ represents an oxycarbonyl group or a carbonyloxy group, $L^{X1}$ represents a $C_1$ to $C_{16}$ divalent saturated aliphatic hydrocarbon group, $L^{X2}$ represents a single bond or a $C_1$ to $C_{15}$ divalent saturated hydrocarbon group, provided that the total carbon number contained in the group of $L^{X1}$ and $L^{X2}$ is 16 or less;

$L^{X3}$ represents a single bond or a $C_1$ to $C_{17}$ divalent saturated aliphatic hydrocarbon group, $L^{X4}$ represents a single bond or a $C_1$ to $C_{16}$ divalent saturated hydrocarbon group, provided that the total carbon number contained in the group of $L^{X3}$ and $L^{X4}$ is 17 or less;

$L^{X5}$ represents a $C_1$ to $C_{15}$ divalent saturated aliphatic hydrocarbon group, $L^{X6}$ and $L^{X7}$ independently represents a single bond or a $C_1$ to $C_{14}$ divalent saturated hydrocarbon group, provided that the total carbon number contained in the group of $L^{X5}$, $L^{X6}$ and $L^{X7}$ is 15 or less;

$L^{X8}$ and $L^{X9}$ independently represents a single bond or a $C_1$ to $C_{12}$ divalent saturated hydrocarbon group, $W^{X1}$ represents a $C_3$ to $C_{15}$ divalent saturated alicyclic hydrocarbon group, provided that the total carbon number contained in the group of $L^{X8}$, $L^{X9}$ and $W^{X1}$ is 15 or less.

$L^{X1}$ is preferably a $C_1$ to $C_8$ divalent saturated aliphatic hydrocarbon group, and more preferably methylene or ethylene group.

$L^{X2}$ is preferably a single bond or a $C_1$ to $C_8$ divalent saturated aliphatic hydrocarbon group, and more preferably a single bond.

$L^{X3}$ is preferably a $C_1$ to $C_8$ divalent saturated aliphatic hydrocarbon group.

$L^{X4}$ is preferably a single bond or a $C_1$ to $C_8$ divalent saturated aliphatic hydrocarbon group.

$L^{X5}$ is preferably a $C_1$ to $C_8$ divalent saturated aliphatic hydrocarbon group, and more preferably methylene or ethylene group.

$L^{X6}$ is preferably a single bond or a $C_1$ to $C_8$ divalent saturated aliphatic hydrocarbon group, and more preferably methylene or ethylene group.

$L^{X7}$ is preferably a single bond or a $C_1$ to $C_8$ divalent saturated aliphatic hydrocarbon group.

$L^{X8}$ is preferably a single bond or a $C_1$ to $C_8$ divalent saturated aliphatic hydrocarbon group, and more preferably a single bond or methylene group.

$L^{X9}$ is preferably a single bond or a $C_1$ to $C_8$ divalent saturated aliphatic hydrocarbon group, and more preferably a single bond or methylene group.

$W^{X1}$ is preferably a $C_3$ to $C_{10}$ divalent saturated alicyclic hydrocarbon group, and more preferably cyclohexanediyl or adamantanediyl group.

Examples of the group represented by the formula (L1-1) include the following ones.

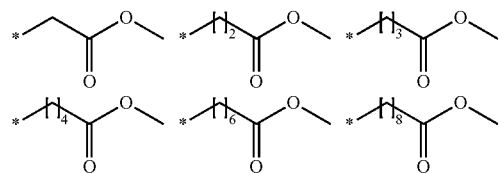

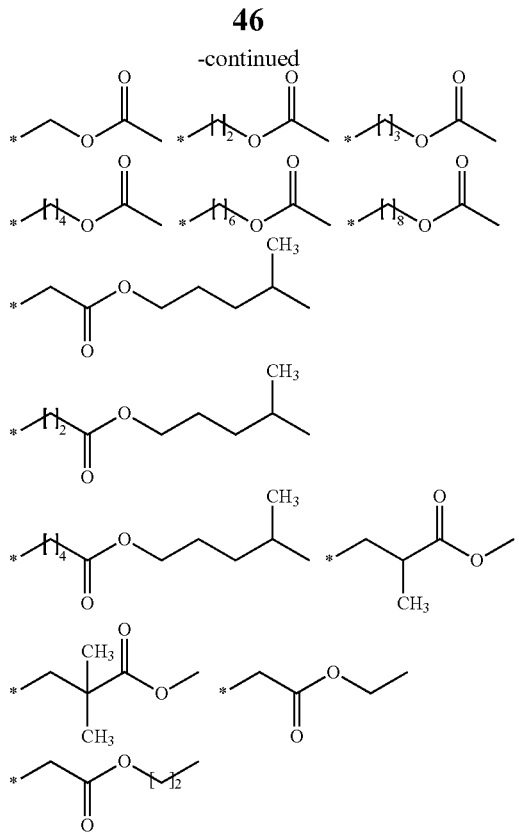

Examples of the group represented by the formula (L1-2) include the following ones.

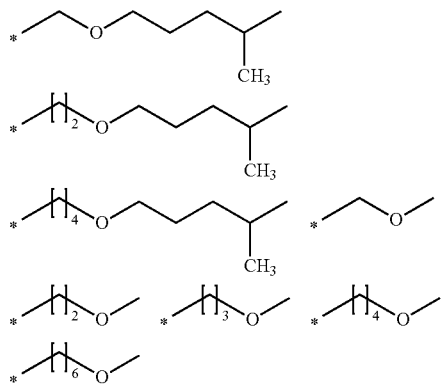

Examples of the group represented by the formula (L1-3) include the following ones.

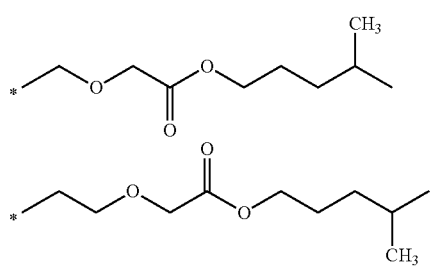

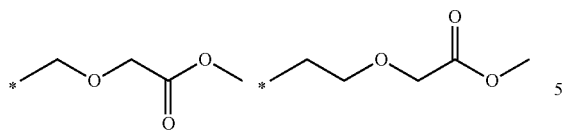
Examples of the group represented by the formula (L1-4) include the following ones.
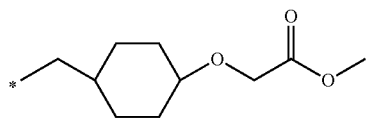
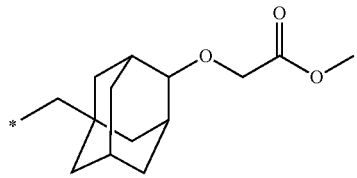
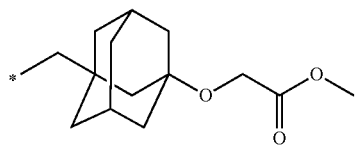
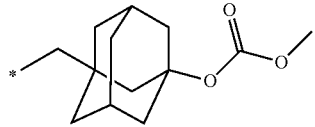
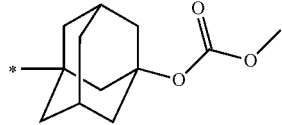
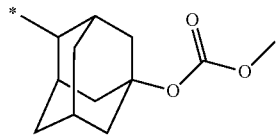
$L^{51}$ is preferably a single bond, methylene group, ethylene group or the groups represented by the formula (L1-1), and more preferably a single bond or the groups represented by the formula (L1-1).
Examples of the structural unit (a5-1) include the following ones.
(a5-1-1)
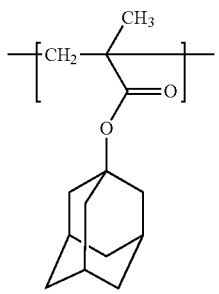
(a5-1-2)
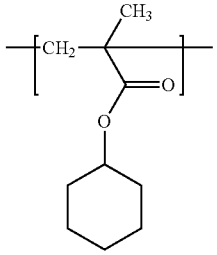
(a5-1-3)
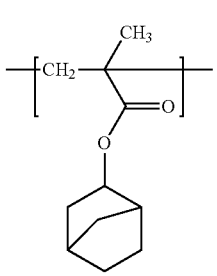
(a5-1-4)
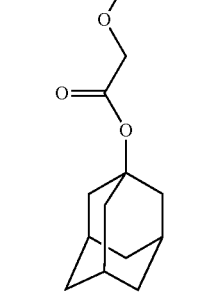
(a5-1-5)
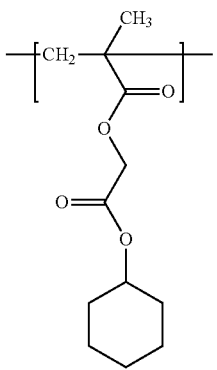

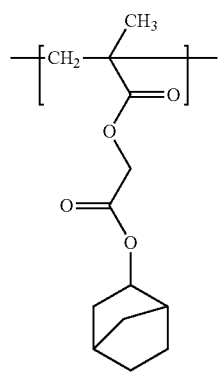
(a5-1-6)
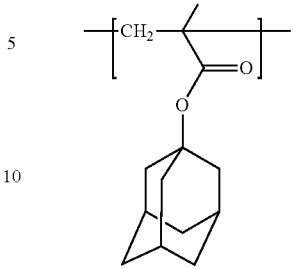
(a5-1-10)
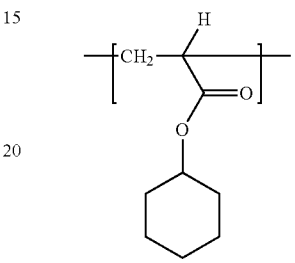
(a5-1-11)
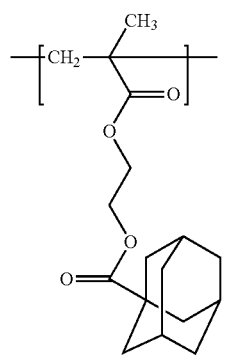
(a5-1-7)
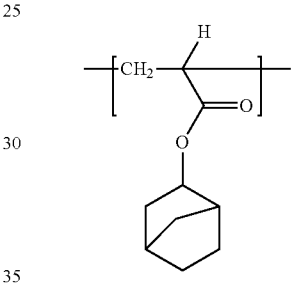
(a5-1-12)
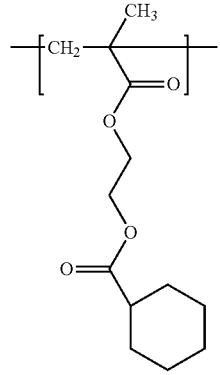
(a5-1-8)
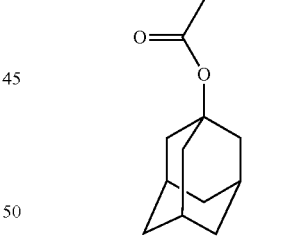
(a5-1-13)
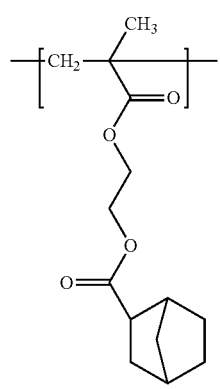
(a5-1-9)
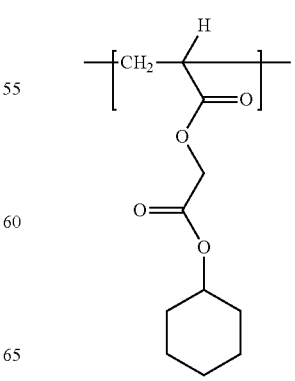
(a5-1-14)

(a5-1-15)
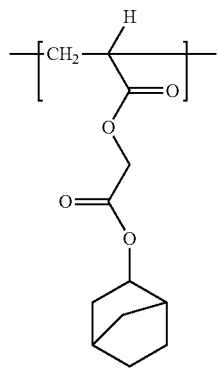
(a5-1-16)
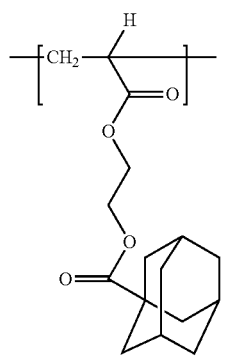
(a5-1-17)
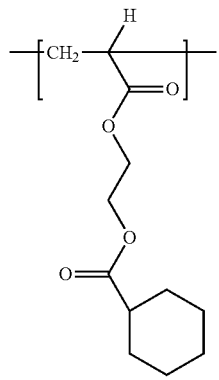
(a5-1-18)
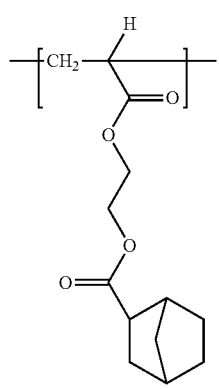
(a5-1-19)
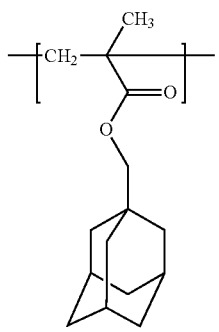
(a5-1-20)
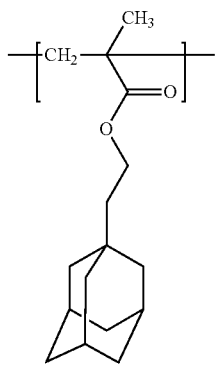
(a5-1-21)
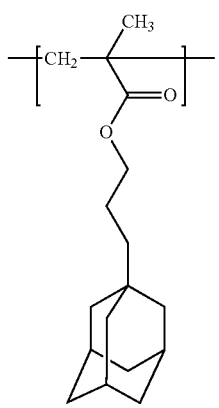
(a5-1-22)
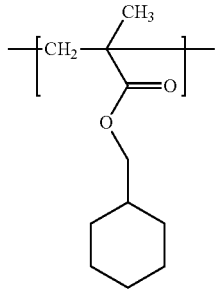

(a5-1-23) 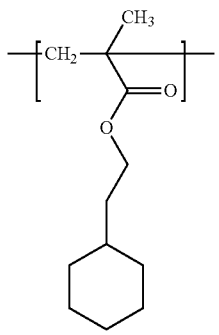

(a5-1-24) 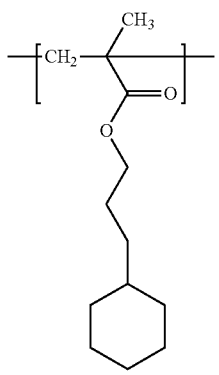

(a5-1-25) 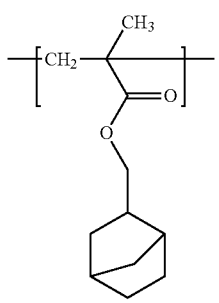

(a5-1-26) 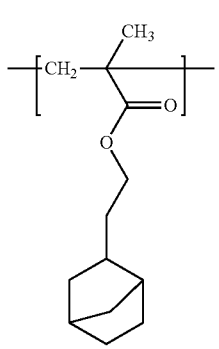

(a5-1-27) 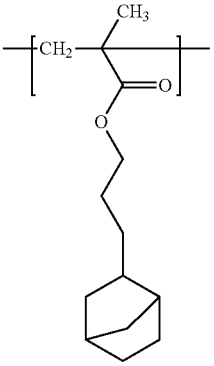

When the resin (X) contains the structural unit (a5), the proportion thereof is generally 1 to 70% by mole, preferably 2 to 60% by mole, more preferably 3 to 50% by mole, with respect to the total structural units (100% by mole) of the resin (X).

The resin (X) may further includes a structural unit other than structural units described above. Examples of the structural unit include a known structural unit.

The weight average molecular weight of the resin (X) is preferably 6,000 or more (more preferably 7,000 or more), and 80,000 or less (more preferably 60,000 or less). In this specification, the weight average molecular weight is a value determined by gel permeation chromatography.

<Resist Composition>

The resist composition of the present invention contains the resin (X), a resin having an acid-labile group and an acid generator (which is sometimes referred to as "acid generator (B)"). Here the "acid-labile group" means a group having a leaving group which is detached by contacting with an acid resulting in forming a hydrophilic group such as a hydroxy or carboxy group.

The resist composition preferably contains a quencher (which is sometimes referred to as "quencher (C)") or a solvent (which is sometimes referred to as "solvent (E)"), more preferably contain the quencher (C) and the solvent (E). The resist composition of the present invention preferably contains a salt weaker in acidity such as a weak acid inner salt (which is sometimes referred to as "weak acid inner salt (D)") as the quencher (C).

<Resin (A)>

The resin includes a structural unit having an acid-labile group (which is sometimes referred to as "structural unit (a1)"). The resin is sometimes referred to as "resin (A)".

The resin (A) may preferably include a structural unit other than the structural unit (a1). Examples of the structural unit other than the structural unit (a1) include a structural unit not having an acid-labile group (which is sometimes referred to as "structural unit (s1)"), and a known structural unit.

<Structural Unit (a1)>

The structural units (a1) is derived from a monomer (which is sometimes referred to as "monomer (a1)") having an acid-labile group.

In the resin (A), the acid-labile group contained in the structural unit (a1) is preferably the following group (1) and/or the group (2):

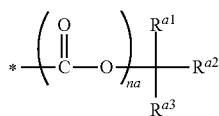
(1)

wherein $R^{a1}$ to $R^{a3}$ independently represent a $C_1$ to $C_8$ alkyl group, a $C_3$ to $C_{20}$ alicyclic hydrocarbon group or combination thereof, or $R^{a1}$ and $R^{a2}$ may be bonded together with a carbon atom bonded thereto to form a $C_3$ to $C_{20}$ divalent alicyclic hydrocarbon group;
na represents an integer of 0 or 1;
* represents a binding site

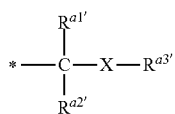
(2)

wherein $R^{a1'}$ and $R^{a2'}$ independently represent a hydrogen atom or a $C_1$ to $C_{12}$ hydrocarbon group, $R^{a3'}$ represents a $C_1$ to $C_{20}$ hydrocarbon group, or $R^{a2'}$ and $R^{a3'}$ may be bonded together with a carbon atom and X bonded thereto to form a divalent $C_3$ to $C_{20}$ heterocyclic group, and a methylene group contained in the hydrocarbon group or the divalent heterocyclic group may be replaced by an oxygen atom or sulfur atom;
X represents —O— or —S—;
* represents a binding site.

Examples of the alkyl group of $R^{a1}$ to $R^{a3}$ include methyl, ethyl, propyl, n-butyl, n-pentyl, n-hexyl, n-heptyl and n-octyl groups.

Examples of the alicyclic hydrocarbon group of $R^{a1}$ to $R^{a3}$ include monocyclic groups such as a cycloalkyl group, i.e., cyclopentyl, cyclohexyl, cycloheptyl, cyclooctyl groups; and polycyclic hydrocarbon groups such as decahydronaphtyl, adamantyl and norbornyl groups as well as groups below. * represents a binding site.

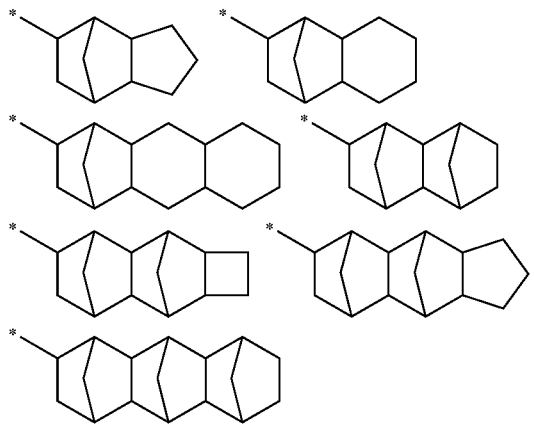

The alicyclic hydrocarbon group of $R^{a1}$ to $R^{a3}$ preferably has 3 to 16 carbon atoms.

Examples of groups combining the alkyl group and the alicyclic hydrocarbon group include methyl cyclohexyl, dimethyl cyclohexyl, methyl norbornyl and cyclohexylmethyl, adamantylmethyl and norbornyletyl groups.

na is preferably an integer of 0.

When $R^{a1}$ and $R^{a2}$ is bonded together to form a divalent alicyclic hydrocarbon group, examples of the group —C($R^{a1}$)($R^{a2}$)($R^{a3}$) include groups below. The divalent alicyclic hydrocarbon group preferably has 3 to 12 carbon atoms. * represent a binding site to —O—.

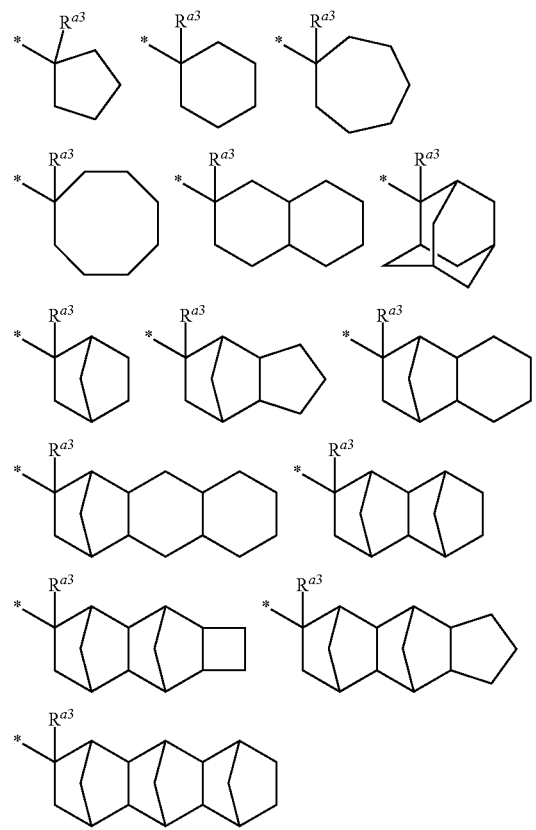

Specific examples of the group represented by the formula (1) include, for example, 1,1-dialkylalkoxycarbonyl group (a group in which $R^{a1}$ to $R^{a3}$ are alkyl groups, preferably tert-butoxycarbonyl group, in the formula (1)), 2-alkyladamantane-2-yloxycarbonyl group (a group in which $R^{a1}$ to $R^{a2}$ and a carbon atom form adamantyl group, and $R^{a3}$ is alkyl group, in the formula (1)), and 1-(adamantane-1-yl)-1-alkylalkoxycarbonyl group (a group in which $R^{a1}$ and $R^{a2}$ are alkyl group, and $R^{a3}$ is adamantyl group, in the formula (1)).

The hydrocarbon group of $R^{a1'}$ to $Ra^{a3'}$ includes any of an alkyl group, an alicyclic hydrocarbon group, an aromatic hydrocarbon group and a group formed by combining them.

Examples of the alkyl group and the alicyclic hydrocarbon group are the same examples as described above.

Examples of the aromatic hydrocarbon group include an aryl group such as phenyl, naphthyl, anthryl, p-methylphenyl, p-tert-butylphenyl, p-adamantylphenyl, tolyl, xylyl, cumenyl, mesityl, biphenyl, phenanthryl, 2,6-diethylphenyl and 2-methyl-6-ethylphenyl groups.

Examples of the divalent heterocyclic group formed by bonding with $R^{a2'}$ and $R^{a3'}$ include groups below.

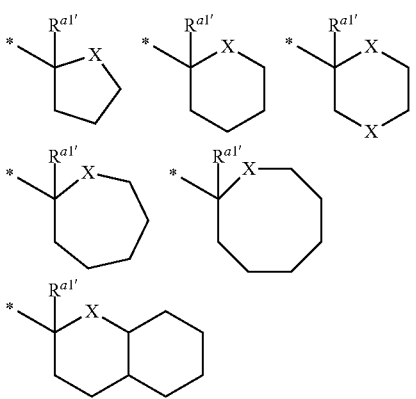

At least one of $R^{a1'}$ and $R^{a2'}$ is preferably a hydrogen atom.

Specific examples of the group represented by the formula (2) include a group below. * represents a binding site.

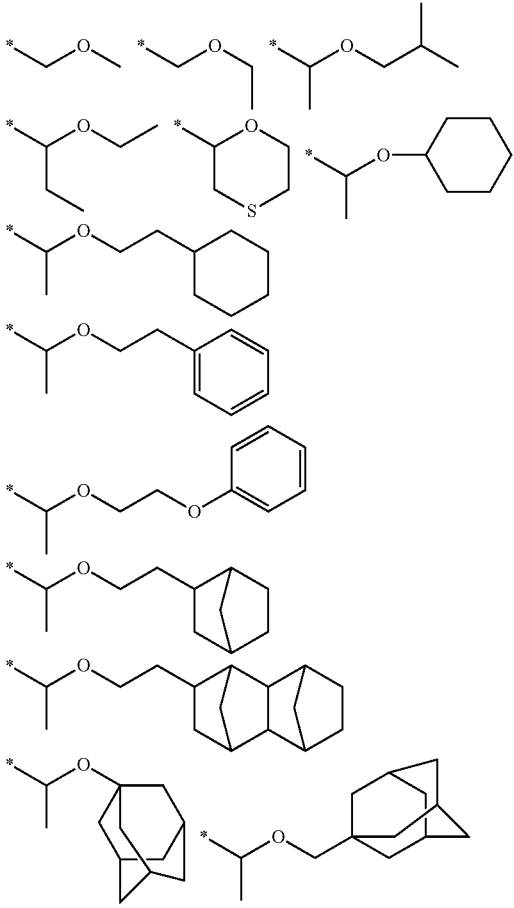

The monomer (a1) is preferably a monomer having an acid-labile group and an ethylene unsaturated bond, and more preferably a (meth)acrylic monomer having the acid-labile group.

Among the (meth)acrylic monomer having an acid-labile group, a monomer having a $C_5$ to $C_{20}$ alicyclic hydrocarbon group is preferred. When a resin (A) having a structural unit derived from a monomer (a1) having a bulky structure such as the alicyclic hydrocarbon group is used for a resist composition, the resist composition having excellent resolution tends to be obtained.

Examples of a structural unit derived from the (meth)acrylic monomer having the group represented by the formula (1) preferably include structural units represented by the formula (a1-0), the formula (a1-1) and the formula (a1-2) below. These may be used as a single structural unit or as a combination of two or more structural units. The structural unit represented by the formula (a1-0), the structural unit represented by the formula (a1-1) and a structural unit represented by the formula (a1-2) are sometimes referred to as "structural unit (a1-0)", "structural unit (a1-1)" and "structural unit (a1-2)"), respectively, and monomers deriving the structural unit (a1-0), the structural unit (a1-1) and the structural unit (a1-2) are sometimes referred to as "monomer (a1-0)", "monomer (a1-1)" and "monomer (a1-2)"), respectively:

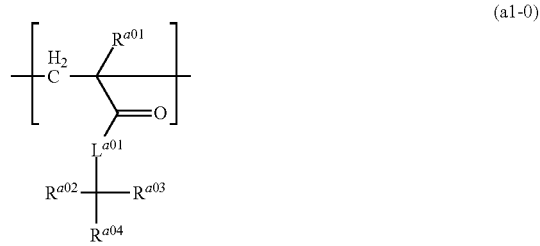

(a1-0)

wherein $L^{a01}$ represents —O— or *—O—$(CH_2)_{k01}$—CO—O—, k01 represents an integer of 1 to 7,

* represents a binding site to —CO—, $R^{a01}$ represents a hydrogen atom or a methyl group, and $R^{a02}$, $R^{a03}$ and $R^{a04}$ independantly represent a $C_1$ to $C_8$ alkyl group, a $C_3$ to $C_{18}$ alicyclic hydrocarbon group or combination thereof.

$L^{a01}$ is preferably an —O— or *—O—$(CH_2)_{k01}$—CO—O— in which k01 is preferably an integer of 1 to 4, more preferably an integer of 1, more preferably an —O—.

Examples of the alkyl group and an alicyclic hydrocarbon group of $R^{a02}$, $R^{a03}$ and $R^{a04}$ and combination thereof are the same examples as the group described in $R^{a1}$ to $R^{a3}$ in the formula (1).

The alkyl group of $R^{a02}$, $R^{a03}$ and $R^{a04}$ is preferably a $C_1$ to $C_6$ alkyl group.

The alicyclic hydrocarbon group of $R^{a02}$, $R^{a03}$ and $R^{a04}$ is preferably a $C_3$ to $C_8$ alicyclic hydrocarbon group, more preferably a $C_3$ to $C_6$ alicyclic hydrocarbon group.

The group formed by combining the alkyl group and the alicyclic hydrocarbon group has preferably 18 or less of carbon atom. Examples of those groups include methyl cyclohexyl, dimethyl cyclohexyl and methyl norbornyl groups.

$R^{a02}$ and $R^{a03}$ is preferably a $C_1$ to $C_6$ alkyl group, more preferably a methyl or ethyl group.

$R^{a04}$ is preferably a $C_1$ to $C_6$ alkyl group or $C_5$ to $C_{12}$ alicyclic hydrocarbon group, more preferably a methyl, ethyl, cyclohexyl or adamantyl group.

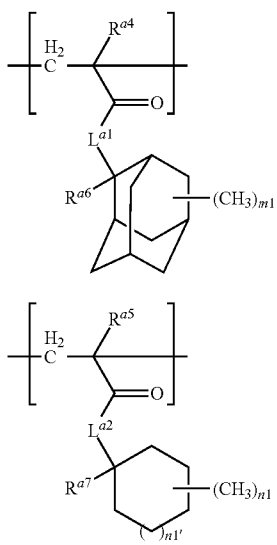

(a1-1)

(a1-2)

wherein $L^{a1}$ and $L^{a2}$ independently represent —O— or *—O—$(CH_2)_{k1}$-CO—O—, k1 represents an integer of 1 to 7,

* represents a binding site to —CO—, $R^{a4}$ and $R^{a5}$ independently represent a hydrogen atom or a methyl group, $R^{a6}$ and $R^{a7}$ independently represent a $C_1$ to $C_8$ alkyl group, a $C_3$ to $C_{18}$ alicyclic hydrocarbon group or a combination thereof, m1 represents an integer of 0 to 14, n1 represents an integer of 0 to 10, and n1' represents an integer of 0 to 3.

$L^{a1}$ and $L^{a2}$ are preferably —O— or *—O—$(CH_2)_{k1'}$—CO—O— in which k1' represents an integer of 1 to 4 and more preferably 1, still more preferably —O—.

$R^{a4}$ and $R^{a5}$ are preferably a methyl group.

Examples of the alkyl group of $R^{a6}$ and $R^{a7}$ include methyl, ethyl, n-propyl, isopropyl, n-butyl, sec-butyl, tert-butyl, n-pentyl, n-hexyl, n-heptyl, 2-ethylhexyl and n-octyl groups.

Examples of the alicyclic hydrocarbon group of $R^{a6}$ and $R^{a7}$ include monocyclic hydrocarbon groups such as a cycloalkyl group, i.e., cyclopropyl, cyclobutyl, cyclopentyl, cyclohexyl, methylcyclohexyl, dimethylcyclohexyl, cycloheptyl and cyclooctyl groups; and polycyclic hydrocarbon groups such as decahydronaphtyl, adamantyl, 2-alkyadamantane-2-yl, 1-(adamantane-1-yl) alkane-1-yl, norbornyl, methyl norbornyl and isobornyl groups.

Examples of group formed by combining the alkyl group and the alicyclic hydrocarbon group of $R^{a6}$ and $R^{a7}$ include an aralkyl group such as benzyl and phenethyl groups.

The alkyl group of $R^{a6}$ and $R^{a7}$ is preferably a $C_1$ to $C_6$ alkyl group.

The alicyclic hydrocarbon group of $R^{a6}$ and $R^{a7}$ is preferably a $C_3$ to $C_8$ alicyclic hydrocarbon group, more preferably a $C_3$ to $C_6$ alicyclic hydrocarbon group.

m1 is preferably an integer of 0 to 3, and more preferably 0 or 1.

n1 is preferably an integer of 0 to 3, and more preferably 0 or 1.

n1' is preferably 0 or 1, and more preferably 1.

Examples of the monomer (a1-0) preferably include monomers represented by the formula (a1-0-1) to the formula (a1-0-12), and more preferably monomers represented by the formula (a1-0-1) to the formula (a1-0-10) below.

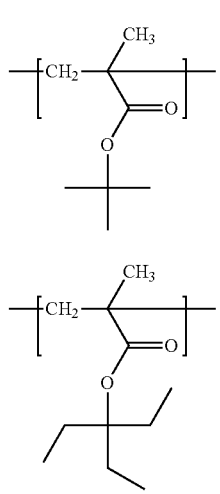

(a1-0-1)

(a1-0-2)

(a1-0-3)

(a1-0-4)

(a1-0-5)

(a1-0-6) 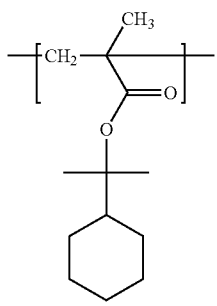

(a1-0-7) 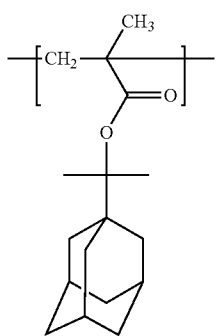

(a1-0-8) 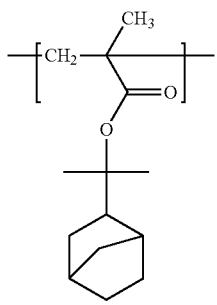

(a1-0-9) 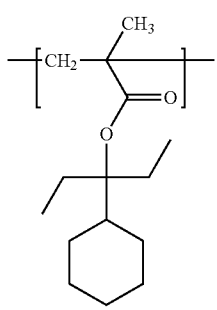

(a1-0-10) 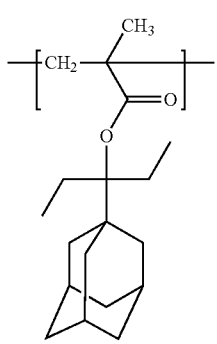

(a1-0-11) 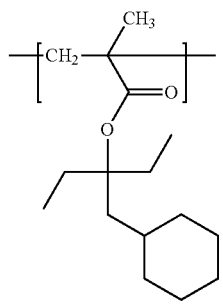

(a1-0-12) 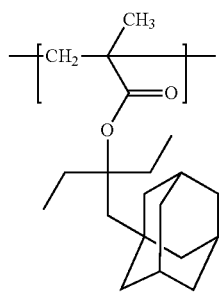

Examples of the structural units (a1-0) include structural units in which a methyl group corresponding to $R^{a01}$ in the structural units represented as above has been replaced by a hydrogen atom.

Examples of the monomer (a1-1) include monomers described in JP 2010-204646A. Among these, the monomers are preferably monomers represented by the formula (a1-1-1) to the formula (a1-1-8), and more preferably monomers represented by the formula (a1-1-1) to the formula (a1-1-4) below.

(a1-1-1) 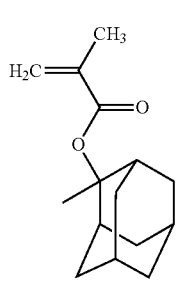

(a1-1-2) 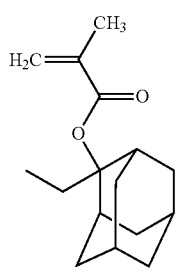

(a1-1-3)
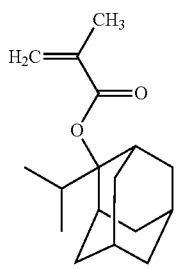

(a1-1-4)
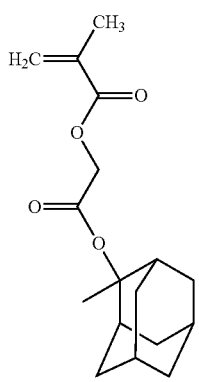

(a1-1-5)
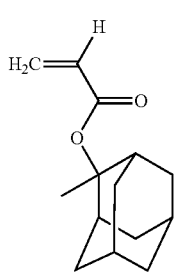

(a1-1-6)
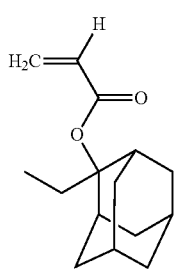

(a1-1-7)
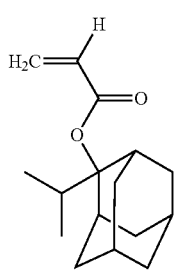

(a1-1-8)
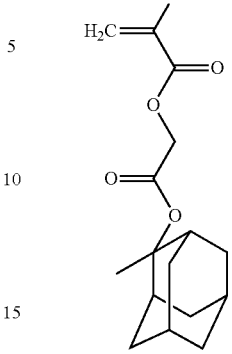

Examples of the monomer (a1-2) include 1-methylcyclopentane-1-yl (meth)acrylate, 1-ethylcyclopentane-1-yl (meth)acrylate, 1-methylcyclohexane-1-yl(meth)acrylate, 1-ethylcyclohexane-1-yl (meth)acrylate, 1-ethylcycloheptane-1-yl (meth)acrylate, 1-ethylcyclooctane-1-yl (meth)acrylate, 1-isopropylcyclopentane-1-yl (meth)acrylate and 1-isopropylcyclohexane-1-yl (meth)acrylate. Among these, the monomers are preferably monomers represented by the formula (a1-2-1) to the formula (a1-2-12), and more preferably monomers represented by the formula (a1-2-3), the formula (a1-2-4), the formula (a1-2-9) and the formula (a1-2-10), and still more preferably monomer represented by the formula (a1-2-3) and the formula (a1-2-9) below.

(a1-2-1)
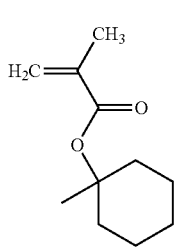

(a1-2-2)
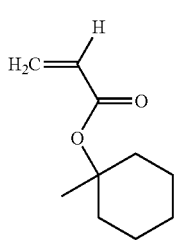

(a1-2-3)
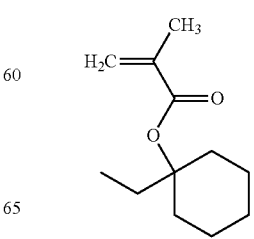

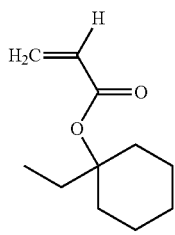 (a1-2-4)

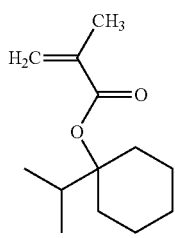 (a1-2-5)

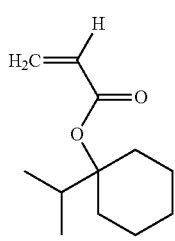 (a1-2-6)

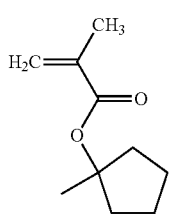 (a1-2-7)

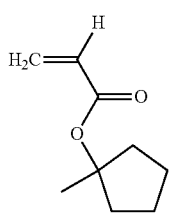 (a1-2-8)

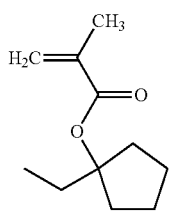 (a1-2-9)

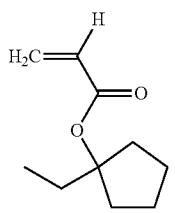 (a1-2-10)

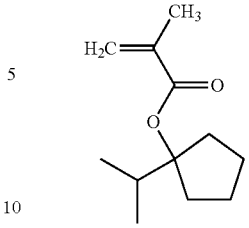 (a1-2-11)

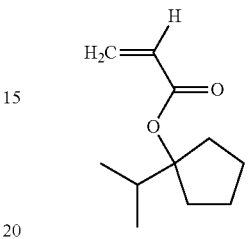 (a1-2-12)

When the resin (A) contains the structural unit (a1-0) and/or the structural unit (a1-1) and/or the structural unit (a1-2), the total proportion thereof is generally 10 to 95% by mole, preferably 15 to 90% by mole, more preferably 20 to 85% by mole, with respect to the total structural units (100% by mole) of the resin (A).

Further, examples of the structural unit (a1) having a group (1) include a structural unit presented by the formula (a1-3). The structural unit represented by the formula (a1-3) is sometimes referred to as "structural unit (a1-3)". The monomer from which the structural unit (a1-3) is derived is sometimes referred to as "monomer (a1-3)".

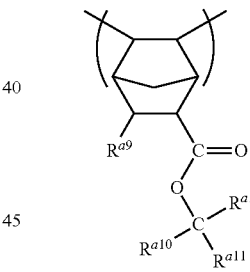 (a1-3)

wherein $R^{a9}$ represents a carboxy group, a cyano group, a —COOR$^{a13}$, a hydrogen atom or a $C_1$ to $C_3$ aliphatic hydrocarbon group that may have a hydroxy group, $R^{a13}$ represents a $C_1$ to $C_8$ aliphatic hydrocarbon group, a $C_3$ to $C_{20}$ alicyclic hydrocarbon group or a group formed by combining thereof, a hydrogen atom contained in the aliphatic hydrocarbon group and the alicyclic hydrocarbon group may be replaced by a hydroxy group, a methylene group contained in the aliphatic hydrocarbon group and the alicyclic hydrocarbon group may be replaced by an oxygen atom or a carbonyl group, and $R^{a10}$, $R^{a11}$ and $R^{a12}$ independently represent a $C_1$ to $C_8$ alkyl hydrocarbon group, a $C_3$ to $C_{20}$ alicyclic hydrocarbon group or a group formed by combining them, or $R^{a10}$ and $R^{a11}$ may be bonded together with a carbon atom bonded thereto to form a $C_1$ to $C_{20}$ divalent hydrocarbon group.

Here, examples of —COOR$^{a13}$ group include a group in which a carbonyl group is bonds to the alkoxy group, such as methoxycarbonyl and ethoxycarbonyl groups.

Examples of the aliphatic hydrocarbon group that may have a hydroxy group of $R^{a9}$ include methyl, ethyl, propyl, hydroxymethy and 2-hydroxyethyl groups.

Examples of the $C_1$ to $C_8$ aliphatic hydrocarbon group of $R^{a13}$ include methyl, ethyl, propyl, isopropyl, n-butyl, sec-butyl, tert-butyl, n-pentyl, n-hexyl, n-heptyl, 2-ethylhexyl and n-octyl groups.

Examples of the $C_3$ to $C_{20}$ alicyclic hydrocarbon group of $R^{a13}$ include cyclopentyl, cyclopropyl, adamantyl, adamantylmetyl, 1-(adamantyl-1-yl)-methylethyl, 2-oxo-oxolane-3-yl, 2-oxo-oxolane-4-yl groups.

Examples of the alkyl group of $R^{a10}$ to $R^{a12}$ include methyl, ethyl, n-propyl, isopropyl, n-butyl, sec-butyl, tert-butyl, n-pentyl, n-hexyl, n-heptyl, 2-ethylhexyl and n-octyl groups.

Examples of the alicyclic hydrocarbon group of $R^{a10}$ to $R^{a12}$ include monocyclic hydrocarbon groups such as a cycloalkyl group, i.e., cyclopropyl, cyclobutyl, cyclopentyl, cyclohexyl, methylcyclohexyl, dimethylcyclohexyl, cycloheptyl, cyclooctyl, and cyclodecyl groups; and polycyclic hydrocarbon groups such as decahydronaphtyl, adamantyl, 2-alkyl-2-adamantyl, 1-(adamantane-1-yl) alkane-1-yl, norbornyl, methyl norbornyl and isobornyl groups.

When $R^{a10}$ and $R^{a11}$ is bonded together with a carbon atom bonded thereto to form a divalent hydrocarbon group, examples of the group—$C(R^{a10})(R^{a11})(R^{a12})$include groups below.

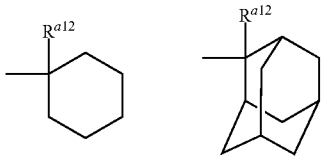

Examples of the monomer (a1-3) include tert-butyl 5-norbornene-2-carboxylate, 1-cyclohexyl-1-methylethyl 5-norbornene-2-carboxylate, 1-methylcyclohexyl 5-norbornene-2-carboxylate, 2-methy-2-adamantane-2-yl 5-norbornene-2-carboxylate, 2-ethyl-2-adamantane-2-yl 5-norbornene-2-carboxylate, 1-(4-methycyclohexyl)-1-methylethyl 5-norbornene-2-carboxylate, 1-(4-hydroxycyclohexyl)-1-methylethyl 5-norbornene-2-carboxylate, 1-methyl-(4-oxo-cyclohexyl)-1-ethyl 5-norbornene-2-carboxylate, and 1-(1-adamantane-1-yl)-1-methylethyl 5-norbornene-2-carboxylate.

The resin (A) having a structural unit (a1-3) can improve the resolution of the obtained resist composition because it has a bulky structure, and also can improve a dry-etching tolerance of the obtained resist composition because of incorporated a rigid norbornene ring into a main chain of the resin (A).

When the resin (A) contains the structural unit (a1-3), the proportion thereof is generally 10% by mole to 95% by mole, preferably 15% by mole to 90% by mole, and more preferably 20% by mole to 85% by mole, with respect to the total structural units constituting the resin (A) (100% by mole).

Examples of a structural unit (a1) having a group (2) include a structural unit represented by the formula (a1-4). The structural unit is sometimes referred to as "structural unit (a1-4)".

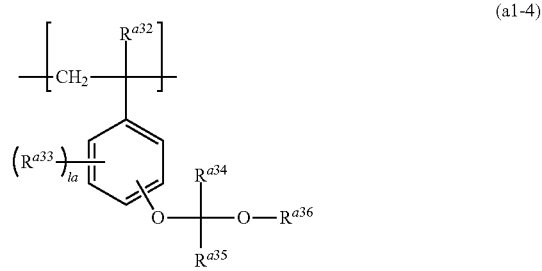

wherein $R^{a32}$ represents a hydrogen atom, a halogen atom or a $C_1$ to $C_6$ alkyl group that may have a halogen atom, $R^{a33}$ in each occurrence independently represent a halogen atom, a hydroxy group, a $C_1$ to $C_6$ alkyl group, a $C_1$ to $C_6$ alkoxy group, a $C_2$ to $C_4$ acyl group, a $C_2$ to $C_4$ acyloxy group, an acryloyloxy group or methacryloyloxy group, 1a represents an integer 0 to 4, $R^{a34}$ and $R^{a35}$ independently represent a hydrogen atom or a $C_1$ to $C_{12}$ hydrocarbon group; and $R^{a36}$ represents a $C_1$ to $C_{20}$ hydrocarbon group, or $R^{a35}$ and $R^{a36}$ may be bonded together with a C—O bonded thereto to form a divalent $C_2$ to $C_{20}$ hydrocarbon group, and a methylene group contained in the hydrocarbon group or the divalent hydrocarbon group may be replaced by an oxygen atom or sulfur atom.

Examples of the alkyl group of $R^{a32}$ and $R^{a33}$ include methyl, ethyl, propyl, isopropyl, butyl, pentyl and hexyl groups. The alkyl group is preferably a $C_1$ to $C_4$ alkyl group, and more preferably a methyl or ethyl group, and still more preferably a methyl group.

Examples of the halogen atom of $R^{a32}$ and $R^{a33}$ include fluorine, chlorine, bromine or iodine atom.

Examples of the alkyl group that may have a halogen atom include trifluoromethyl, difluoromethyl, methyl, perfluoromethyl, 1,1,1-trifluoroethyl, 1,1,2,2-tetrafluoroethyl, ethyl, perfluoropropyl, 1,1,1,2,2-pentafluoropropyl, propyl, perfluorobutyl, 1,1,2,2,3,3,4,4-octafluorobutyl, butyl, perfluoropentyl, 1,1,1,2,2,3,3,4,4-nonafluoropentyl, n-pentyl, n-hexyl and n-perfluorohexyl groups.

Examples of an alkoxy group include methoxy, ethoxy, propoxy, butoxy, pentyloxy, and hexyloxy groups. The alkoxy group is preferably a $C_1$ to $C_4$ alkoxy group, more preferably a methoxy and ethoxy group, and still more preferably methoxy group.

Examples of the acyl group include acetyl, propanonyl and butylyl groups.

Examples of the acyloxy group include acetyloxy, propanonyloxy and butylyloxy groups.

Examples of the hydrocarbon group of $R^{a34}$ and $R^{a35}$ are the same examples as described in $R^{a1'}$ to $R^{a2'}$ in the formula (2).

Examples of hydrocarbon group of $R^{a36}$ include a $C_1$ to $C_{18}$ alkyl group, a $C_3$ to $C_{18}$ alicyclic hydrocarbon group, a $C_6$ to $C_{18}$ aromatic hydrocarbon group or a group formed by combining them.

In the formula (a1-4), $R^{a32}$ is preferably a hydrogen atom.

$R^{a33}$ is preferably a $C_1$ to $C_4$ alkoxy group, more preferably a methoxy and ethoxy groups, and still more preferably methoxy group.

1a is preferably 0 or 1, and more preferably 0.

$R^{a34}$ is preferably a hydrogen atom.

$R^{a35}$ is preferably a $C_1$ to $C_{12}$ hydrocarbon group, and more preferably a methyl or ethyl group.

The hydrocarbon group of $R^{a36}$ is preferably a $C_1$ to $C_{18}$ alkyl group, a $C_3$ to $C_{18}$ alicyclic hydrocarbon group, a $C_6$ to $C_{18}$ aromatic hydrocarbon group or a combination thereof, and more preferably a $C_1$ to $C_{18}$ alkyl group, a $C_3$ to $C_{18}$ alicyclic hydrocarbon group or a $C_7$ to $C_{18}$ aralkyl group. The alkyl group and the alicyclic hydrocarbon group of $R^{a36}$ is preferably not substituted. When the aromatic hydrocarbon group of $R^{a36}$ has a substituent, the substituent is preferably a $C_6$ to $C_{10}$ aryloxy group.

Examples of the monomer from which a structural unit (a1-4) is derived include monomers described in JP 2010-204646A. Among these, the monomers are preferably monomers represented by the formula (a1-4-1) to the formula (a1-4-7), and more preferably monomers represented by the formula (a1-4-1) to the formula (a1-4-5) below.

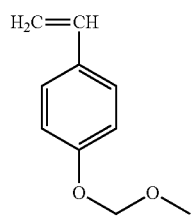

(a1-4-1)

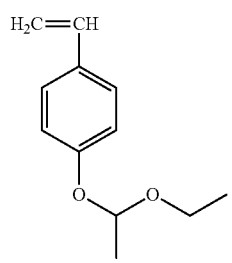

(a1-4-2)

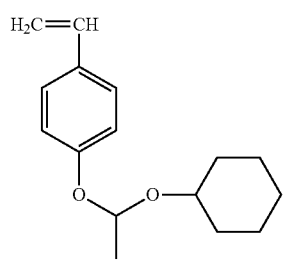

(a1-4-3)

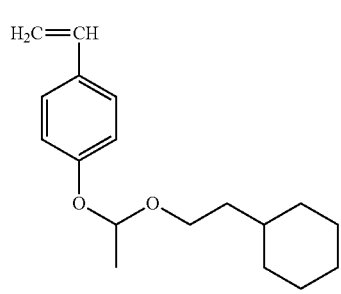

(a1-4-4)

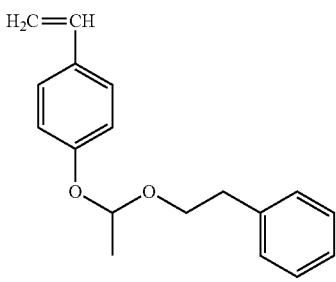

(a1-4-5)

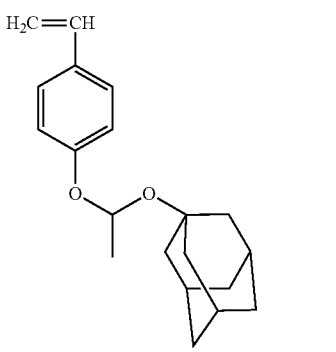

(a1-4-6)

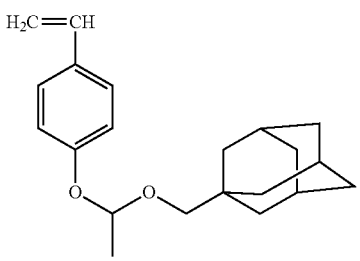

(a1-4-7)

When the resin (A) contains the structural unit (a1-4), the proportion thereof is generally 10% by mole to 95% by mole, preferably 15% by mole to 90% by mole, more preferably 20% by mole to 85% by mole, with respect to the total structural units constituting the resin (A) (100% by mole).

Examples of a structural unit having an acid-labile group include a structural unit represented by the formula (a1-5). Such structural unit is sometimes referred to as "structural unit (a1-5)".

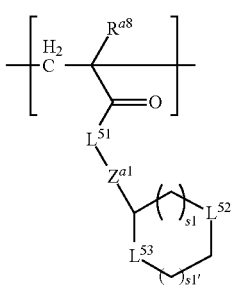

(a1-5)

wherein $R^{a8}$ represents a hydrogen atom, a halogen atom or a $C_1$ to $C_6$ alkyl group that may have a halogen atom, $Z^{a1}$ represent a single bond or *—$(CH_2)_{h3}$—CO—$L^{54}$—, h3 represents an integer of 1 to 4,

* represents a binding site to $L^{51}$, $L^{51}$, $L^{52}$ and $L^{53}$ independently represent —O— or —S—, s1 represents an integer of 1 to 3, and s1' represents an integer of 0 to 3.

In the formula (a1-5), $R^{a8}$ is preferably a hydrogen atom, a methyl group or trifluoromethyl group;

$L^{51}$ is preferably —O—;

$L^{52}$ and $L^{53}$ are independently preferably —O— or —S—, and more preferably one is —O— and another is —S—.

s1 is preferably 1;

s1' is preferably an integer of 0 to 2;

$Z^{a1}$ is preferably a single bond or *—CH$_2$—CO—O—.

Examples of a monomer from which a structural unit (a1-5) is derived include a monomer described in JP2010-61117A. Among these, the monomers are preferably monomers represented by the formula (a1-5-1) to the formula (a1-5-4), and more preferably monomers represented by the formula (a1-5-1) to the formula (a1-5-2) below.

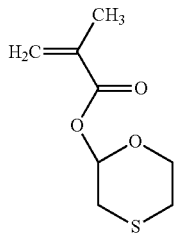
(a1-5-1)

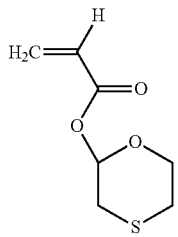
(a1-5-2)

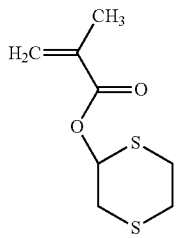
(a1-5-3)

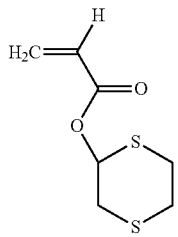
(a1-5-4)

When the resin (A) contains the structural unit (a1-5), the proportion thereof is generally 1% by mole to 50% by mole, preferably 3% by mole to 45% by mole, and more preferably 5% by mole to 40% by mole, with respect to the total structural units (100% by mole) constituting the resin (A).

Examples of a structural unit (a1) having an acid-labile group in a resin (A) is preferably at least one, more prefer-ably two or more structural units selected from the structural unit (a1-0), the structural unit (a1-1), the structural unit (a1-2), the structural unit (a1-5), still more preferably a combination of the structural unit (a1-1) and the structural unit (a1-2), a combination of the structural unit (a1-1) and the structural unit (a1-5), a combination of the structural unit (a1-1) and the structural unit (a1-0), a combination of the structural unit (a1-2) and the structural unit (a1-0), a combination of the structural unit (a1-5) and the structural unit (a1-0), a combination of the structural unit (a1-0), the structural unit (a1-1) and the structural unit (a1-2), a combination of the structural unit (a1-0), the structural unit (a1-1) and the structural unit (a1-5), in particular preferably a combination of the structural unit (a1-1) and the structural unit (a1-2), and a combination of the structural unit (a1-1) and the structural unit (a1-5).

<Structural Unit Having No Acid-Labile Group (s)>

The structural units (s) is derived from a monomer (which is sometimes referred to as "monomer(s)") having no acid-labile group.

For the monomer (s) from which a structural unit (s) is derived, a known monomer having no acid-labile group can be used.

As the structural unit (s), a structural unit having a hydroxy group or a lactone ring but having no acid-labile group is preferred. When a resin containing the structural unit derived from a structural unit having hydroxy group but having no acid-labile group (such structural unit is sometimes referred to as "structural unit (a2)") and/or a structural unit having a lactone ring but having no acid-labile group (such structural unit is sometimes referred to as "structural unit (a3)") is used, the adhesiveness of resist to a substrate and resolution of resist pattern tend to be improved.

<Structural Unit (a2)>

The structural unit (a2) having a hydroxy group may be an alcoholic hydroxy group or a phenolic hydroxy group.

When KrF excimer laser lithography (248 nm), or high-energy irradiation such as electron beam or EUV (extreme ultraviolet) is used for the resist composition, using the structural unit having a phenolic hydroxy group as structural unit (a2) is preferred.

When ArF excimer laser lithography (193 nm) is used, using the structural unit having an alcoholic hydroxy group as the structural unit (a2) is preferred, using the structural represented by the formula (a2-1) is more preferred.

The structural unit (a2) may be used as a single structural unit or as a combination of two or more structural units.

Examples of the structural unit (a2) having a phenolic hydroxy group include a structural unit (which is sometimes referred to as "structural unit (a2-0)") represented by the formula (a2-0).

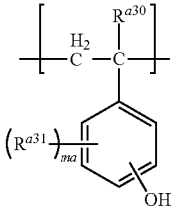
(a2-0)

wherein $R^{a30}$ represents a hydrogen atom, a halogen atom or a $C_1$ to $C_6$ alkyl group that may have a halogen atom, $R^{a31}$ in each occurance independently represents a halogen atom, hydroxy group, a $C_1$ to $C_6$ alkyl group, a $C_1$ to $C_6$ alkoxy group, a $C_2$ to $C_4$ acyl group, a $C_2$ to $C_4$ acyloxy group, an acryloyloxy group or methacryloyloxy group, and ma represents an integer 0 to 4.

Examples of the alkyl group include methyl, ethyl, propyl, isopropyl, butyl, n-pentyl and n-hexyl groups.

Example of the halogen atom is a chlorine atom, a fluorine atom and bromine atom.

Examples of a $C_1$ to $C_6$ alkyl group that may have a halogen atom of $R^{a30}$ include trifluoromethyl, difluoromethyl, methyl, perfluoromethyl, 1,1,1-trifluoroethyl, 1,1,2,2-tetrafluoroethyl, ethyl, perfluoropropyl, 1,1,1,2,2-pentafluoropropyl, propyl, perfluorobutyl, 1,1,2,2,3,3,4,4-octafluorobutyl, butyl, perfluoropentyl, 1,1,1,2,2,3,3,4,4-nonafluoropentyl, n-pentyl, n-hexyl and n-perfluorohexyl groups.

$R^{a30}$ is preferably a hydrogen atom or a $C_1$ to $C_4$ alkyl group, and more preferably a hydrogen atom, methyl or ethyl group, and still more preferably a hydrogen atom or methyl group.

Examples of a $C_1$ to $C_6$ alkoxy group of $R^{a31}$ include methoxy, ethoxy, propoxy, butoxy, pentyloxy, and hexyloxy groups. $R^{a31}$ is preferably a $C_1$ to $C_4$ alkoxy group, more preferably a methoxy and ethoxy group, and still more preferably methoxy group.

Examples of the acyl group include acetyl, propanonyl and butylyl groups.

Examples of the acyloxy group include acetyloxy, propanonyloxy and butylyloxy groups.

ma is preferably 0, 1 or 2, more preferably 0 or 1, still more preferably 0.

The structural unit (a2-0) having a phenolic hydroxy group is preferably a structural unit represented below.

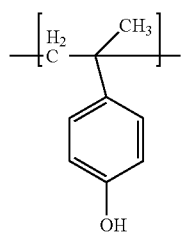
(a2-0-1)

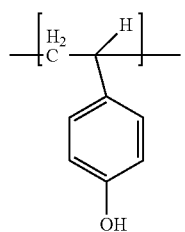
(a2-0-2)

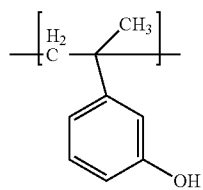
(a2-0-3)

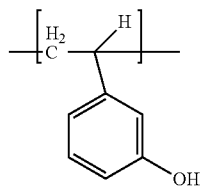
(a2-0-4)

Among these, a structural unit represented by the formula (a2-0-1) or the formula (a2-0-2) is preferred.

Examples of a monomer from which the structural unit (a2-0) is derived include monomers described in JP2010-204634A.

The resin (A) which contains the structural units (a2) having a phenolic hydroxy group can be produced, for example, by polymerizing a monomer where its phenolic hydroxy group has been protected with a suitable protecting group, followed by deprotection. The deprotection is carried in such a manner that an acid-labile group in the structural unit (a1) is significantly impairred. Examples of the protecting group for a phenolic hydroxy group include an acetyl group.

When the resin (A) contains the structural unit (a2-0) having the phenolic hydroxy group, the proportion thereof is generally 5% by mole to 95% by mole, preferably 10% by mole to 80% by mole, more preferably 15% by mole to 80% by mole, with respect to the total structural units (100% by mole) constituting the resin (A).

Examples of the structural unit (a2) having alcoholic hydroxy group include the structural unit (which is sometimes referred to as "structural unit (a2-1)") represented by the formula (a2-1).

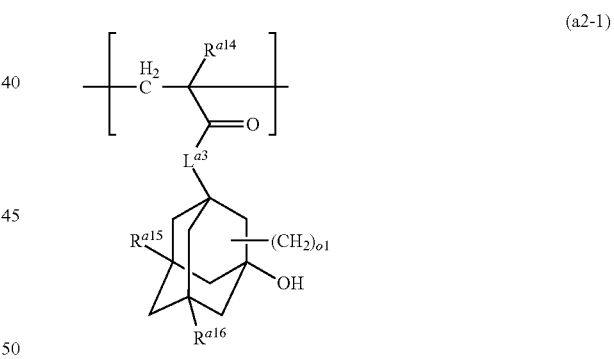
(a2-1)

wherein $L^{a3}$ represents —O— or *—O—$(CH_2)_{k2}$—CO—O—, k2 represents an integer of 1 to 7,

* represents a binding site to —CO—, $R^{a14}$ represents a hydrogen atom or a methyl group, $R^{a15}$ and $R^{a16}$ each independently represent a hydrogen atom, a methyl group or a hydroxy group, and o1 represents an integer of 0 to 10.

In the formula (a2-1), $L^{a3}$ is preferably —O—, —O—$(CH_2)_{f1}$—CO—O—, here f1 represents an integer of 1 to 4, and more preferably —O—.

$R^{a14}$ is preferably a methyl group.

$R^{a15}$ is preferably a hydrogen atom.

$Ra^{a16}$ is preferably a hydrogen atom or a hydroxy group.

o1 is preferably an integer of 0 to 3, and more preferably an integer of 0 or 1.

Examples of the monomer from which the structural unit (a2-1) is derived include monomers described in JP2010-204646A. Among these, the monomers are preferably monomers represented by the formula (a2-1-1) to the formula (a2-1-6), more preferably structural units represented by the formula (a2-1-1) to the formula (a2-1-4), and still more preferably structural units represented by the formula (a2-1-1) and the formula (a2-1-3) below.

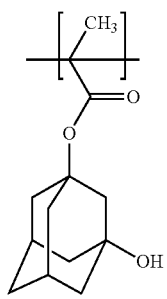

(a2-1-1)

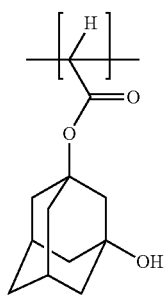

(a2-1-2)

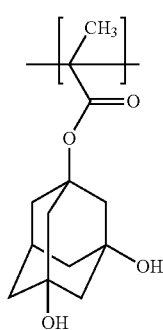

(a2-1-3)

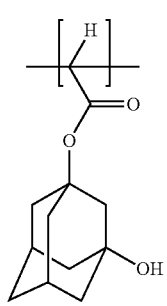

(a2-1-4)

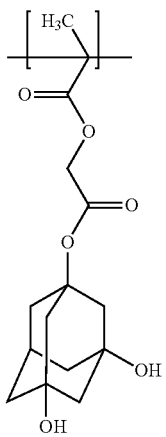

(a2-1-5)

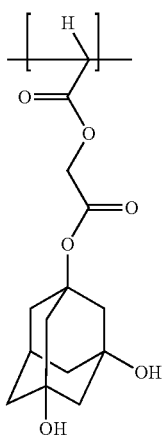

(a2-1-6)

Examples of monomers introducing the structural unit (a2) having the alcoholic hydroxy group include monomers described in JP2010-204646A.

When the resin (A) contains the structural unit (a2) having the alcoholic hydroxy group, the proportion thereof is generally 1% by mole to 45% by mole, preferably 1% by mole to 40% by mole, more preferably 1% by mole to 35% by mole, and still more preferably 2% by mole to 20% by mole, with respect to the total structural units (100% by mole) constituting the resin (A).

Structural Unit (a3)

The lactone ring included in the structural unit (a3) may be a monocyclic compound such as β-propiolactone, γ-butyrolactone, δ-valerolactone, or a condensed ring of monocyclic lactone ring with another ring. Examples of the lactone ring preferably include γ-butyrolactone, amadantane lactone, or bridged ring with γ-butyrolactone.

Examples of the structural unit (a3) include structural units represented by any of the formula (a3-1), the formula (a3-2), the formula (a3-3) and the formula (a3-4). These structural units may be used as a single unit or as a combination of two or more units.

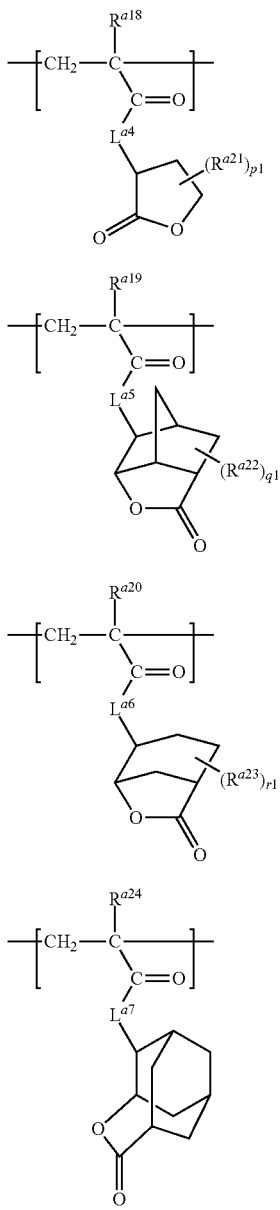

(a3-1)

(a3-2)

(a3-3)

(a3-4)

wherein $L^{a4}$ represents *—O— or *—O—$(CH_2)_{k3}$—CO—O—, k3 represents an integer of 1 to 7, * represents a binding site to a carbonyl group, $R^{a18}$ represents a hydrogen atom or a methyl group, $R^{a21}$ in each occurrence represents a $C_1$ to $C_4$ aliphatic hydrocarbon group, and p1 represents an integer of 0 to 5, $L^{a5}$ represents *—O— or *—O—$(CH_2)_{k3}$—CO—O—, k3 represents an integer of 1 to 7, * represents a binding site to a carbonyl group, $R^{a19}$ represents a hydrogen atom or a methyl group, $R^{a22}$ in each occurrence represents a carboxy group, a cyano group or a $C_1$ to $C_4$ aliphatic hydrocarbon group, q1 represents an integer of 0 to 3, $L^{a6}$ represents *—O— or *—O—$(CH_2)_{k3}$—CO—O—, k3 represents an integer of 1 to 7, * represents a binding site to a carbonyl group, $R^{a20}$ represents a hydrogen atom or a methyl group, $R^{a23}$ in each occurrence represents a carboxy group, a cyano group or a $C_1$ to $C_4$ aliphatic hydrocarbon group, and r1 represents an integer of 0 to 3, $R^{a24}$ represents a hydrogen atom, a halogen atom or a $C_1$ to $C_6$ alkyl group that may have a halogen atom, $L^{a7}$ represents a single bond, -O-, *-O-$L^{a8}$-O-, *-O-$L^{a8}$-CO-O-, *-O-$L^{a8}$-CO-O-$L^{a9}$-CO-O-, or *-O-$L^{a8}$-O-CO-$L^{a9}$-O-; * represents a binding site to a carbonyl group, and $L^{a8}$ and $L^{a9}$ independently represents a $C_1$ to $C_6$ alkanediyl group.

Examples of the aliphatic hydrocarbon group $R^{a21}$, $R^{a22}$ and $R^{a23}$ include an alkyl group such as methyl, ethyl, n-propyl, isopropyl, n-butyl, sec-butyl and tert-butyl groups.

Examples of the halogen atom of $R^{a24}$ include fluorine, chlorine, bromine or iodine atom; Examples of the alkyl group of $R^{a24}$ include methyl, ethyl, n-propyl, isopropyl, n-butyl, sec-butyl, tert-butyl, n-pentyl and n-hexyl groups, preferably a $C_1$ to $C_4$ alkyl group, more preferably a methyl or ethyl group.

Examples of the alkyl group having a halogen atom of $R^{a24}$ include trifluoromethyl, perfluoroethyl, perfluoropropyl, perfluoro-isopropyl, perfluorobutyl, perfluoro-sec-butyl, perfluoro-tert-butyl, perfluoropentyl, perfluorohexyl, trichloromethyl, tribromomethyl and triiodomethyl groups.

Examples of the alkanediyl group of $L^{a8}$ and $L^{a9}$ include methylene, ethylene, propane-1,3-diyl, propane-1,2-diyl, butane-1,4-diyl, pentane-1,5-diyl, hexane-1,6-diyl, butane-1,3-diyl, 2-methylpropane-1,3-diyl, 2-methylpropane-1,2-diyl, pentane-1,4-diyl and 2-methylbutane-1,4-diyl groups.

In the formulae (a3-1) to (a3-3), $L^{a4}$ to $L^{a6}$ is independently preferably —O—, *—O—$(CH_2)_{k3}$—O—O—, here k3' represents an integer of 1 to 4, more preferably —O— or *—O—$CH_2$—CO—O—, and still more preferably *—O—.

$R^{a18}$ to $R^{a21}$ is preferably a methyl group.

$R^{a22}$ and $R^{a23}$ are independently preferably a carboxy group, a cyano group or a methyl group.

p1, q1 and r1 are independently preferably an integer of 0 to 2, and more preferably 0 or 1.

In the formula (a3-4), $R^{a24}$ is preferably a hydrogen atom or a $C_1$ to $C_4$ alkyl group, more preferably a hydrogen atom, a methyl group or an ethyl group, and still more preferably a hydrogen atom or a methyl group.

$L^{a7}$ is preferably a single bond or *-O-$L^{a8}$-CO-O-, and more preferably a single bond, -O-$CH_2$-CO-O- or -O-$C_2H_4$-CO-O-.

Examples of the monomer from which the structural unit (a3) is derived include monomers described in JP2010-204646A, monomers described in JP2000-122294A and monomers described in JP2012-41274A. Among these, the structural units are preferably structural units represented by the formula (a3-1-1) to the formula (a3-1-4), the formula (a3-2-1) to the formula (a3-2-4), the formula (a3-3-1) to the formula (a3-3-4), the formula (a3-4-1) to the formula (a3-4-12), more preferably monomers represented by the formula (a3-1-1) to the formula (a3-1-2), the formula (a3-2-3), the formula (a3-2-4), the formula (a3-4-1) and the formula (a3-4-2), and still more preferably monomers represented by the formula (a3-1-1), the formula (a3-2-3) or the formula (a3-4-2) below.

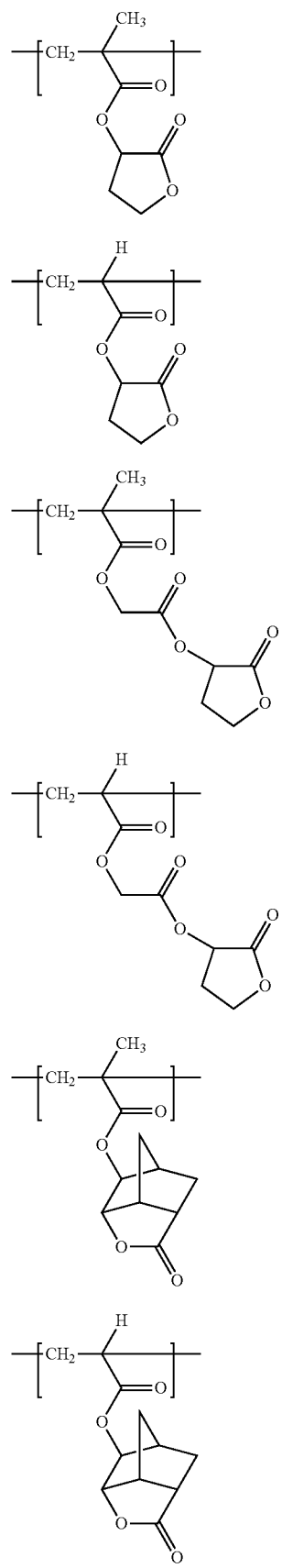

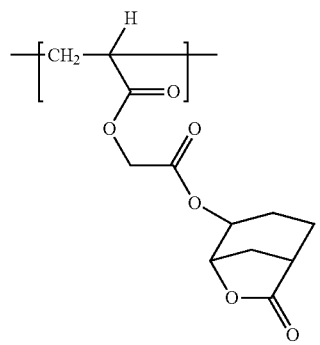 (a3-4-4)
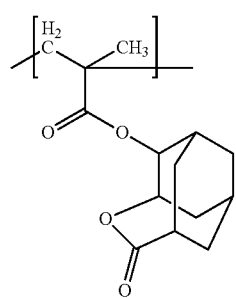 (a3-4-1)
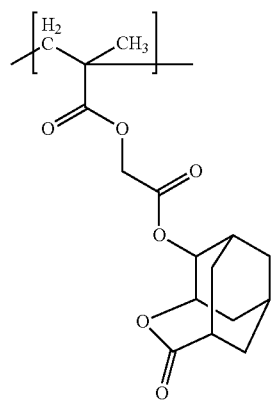 (a3-4-2)
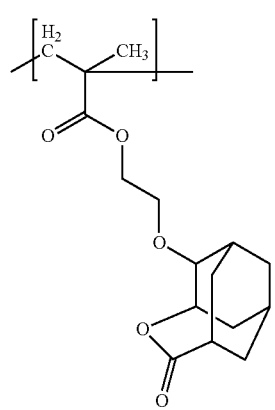 (a3-4-3)
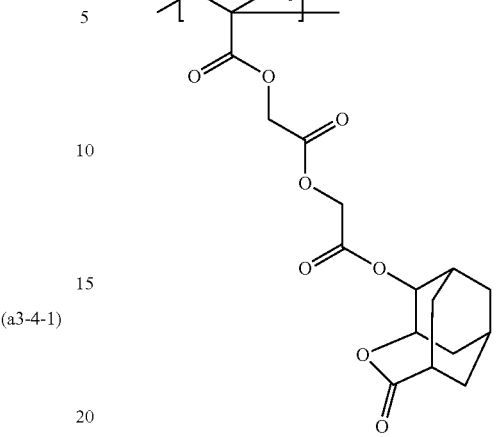 (a3-4-4)
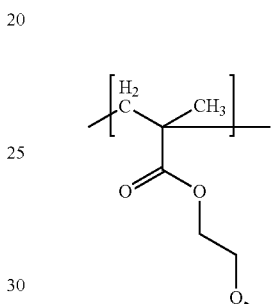 (a3-4-5)
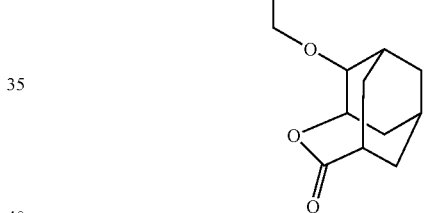 (a3-4-5)
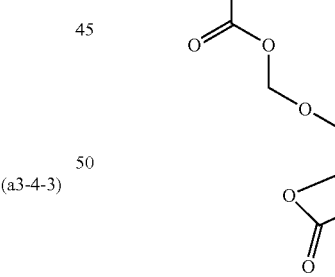 (a3-4-6)
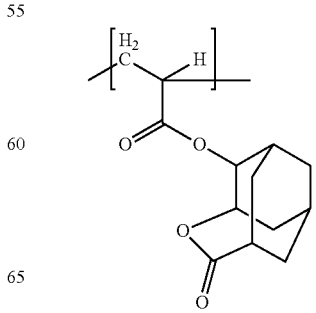 (a3-4-7)

(a3-4-8)
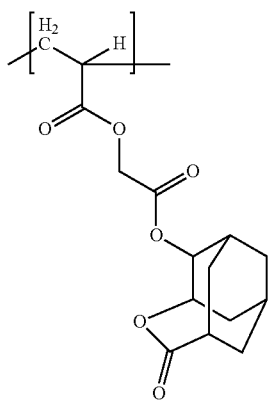

(a3-4-9)
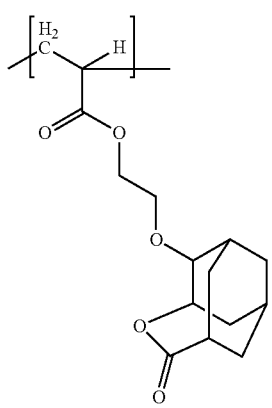

(a3-4-10)
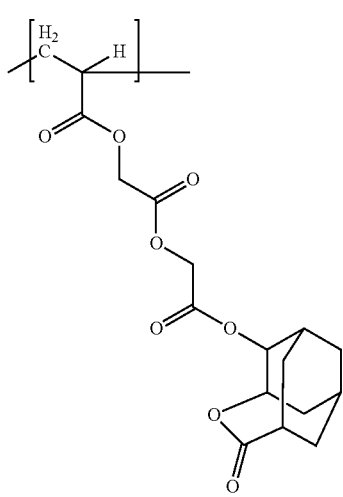

(a3-4-11)
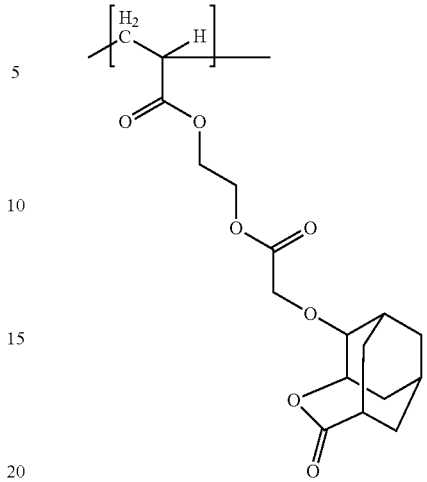

(a3-4-12)
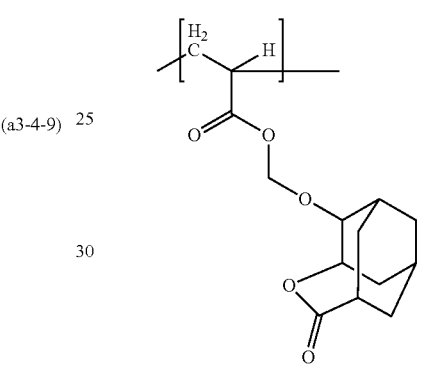

When the resin (A) contains the structural units (a3), the total proportion thereof is preferably 5% by mole to 70% by mole, more preferably 10% by mole to 65% by mole, still more preferably 10% by mole to 60% by mole, with respect to the total structural units (100% by mole) constituting the resin (A).

The proportion each of the formula (a3-1), the formula (a3-2), the formula (a3-3) and the formula (a3-4) is preferably 5% by mole to 60% by mole, more preferably 5% by mole to 50% by mole, still more preferably 10% by mole to 50% by mole, with respect to the total structural units (100% by mole) constituting the resin (A).

<Other Structural Unit (t)>

The resin (A) may include other structural unit (t) as a structural unit in addition to the structural unit (a1) and the structural unit (s). Examples of the structural unit (t) include a structural unit (a4) and a structural unit (a5) other than the structural unit (a2) and the structural unit (a3).

When the resin (A) contains the structural unit (a4), the proportion thereof is generally 1 to 20% by mole, preferably 2 to 15% by mole, more preferably 3 to 10% by mole, with respect to the total structural units (100% by mole) of the resin (A).

When the resin (A) contains the structural unit (a5), the proportion thereof is generally 1 to 30% by mole, preferably 2 to 20% by mole, more preferably 3 to 15% by mole, with respect to the total structural units (100% by mole) of the resin (A).

The resin (A) may include a structural unit other than structural units described above. Examples of the structural unit include a known structural unit.

The resin (A) preferably is a resin having the structural unit (a1) and the structural unit (s), that is, a copolymer of the monomer (a1) and the monomer (s). In this copolymer, the structural unit (a1) is preferably at least one of the structural unit (a1-0), the structural unit (a1-1) and the structural unit (a1-2) (preferably the structural unit having a cyclohexyl group or a cyclopentyl group), and more preferably is the structural unit (a1-1) or the structural unit (a1-2) (preferably the structural unit having a cyclohexyl group or a cyclopentyl group).

The structural unit (s) is preferably at least one of the structural unit (a2) or the structural unit (a3). The structural unit (a2) is preferably the structural unit represented by the formula (a2-1). The structural unit (a3) is preferably at least one of structural units represented by γ-butyrolactone ring, a bridged ring having γ-butyrolactone ring structure or adamantanelactone ring.

The proportion of the structural unit derived from the monomer having an adamantyl group (in particular, the structural unit (a1-1)) in the resin (A) is preferably 15% by mole or more with respect to the structural units (a1). As the mole ratio of the structural unit derived from the monomer having an adamantyl group increases within this range, the dry etching resistance of the resulting resist improves.

The structural unit constituting the resin (A) may be used as a single structural unit or as a combination of two or more structural units. The resin (A) can be produced by a known polymerization method, for example, radical polymerization method, using a monomer introducing the structural unit. The proportion of the structural unit in the resin (A) can be adjusted by amount of a monomer used in polymerization.

The weight average molecular weight of the resin (A) is preferably 2,000 or more (more preferably 2,500 or more, and still more preferably 3,000 or more), and 50,000 or less (more preferably 30,000 or less, and still more preferably 15,000 or less).

The weight average molecular weight is a value determined by gel permeation chromatography.

When a resist composition contain the resin (X), the proportion thereof is preferably 1 to 60 parts by mass, more preferably 3 to 50 parts by mass, and still more preferably 5 to 40 parts by mass, in particular preferably 7 to 30 parts by mass, with respect to the resin (A) (100 parts by mass).

The total proportion of the resin (A) and the resin (X) is preferably 80% by mass to 99% by mass, and more preferably 90% by mass to 99% by mass, with respect to the total solid proportion of the resist composition.

The solid proportion of the resist composition can be measured with a known analytical method such as, for example, liquid chromatography and gas chromatography.

<Resin Other than Resin (A) and Resin (X)>

A resist composition of the present invention may further include another resin in addition to the resin (A) and the resin (X). Examples of the resin include a resin having neither the structural unit (I) nor the structural unit (a), for example, a resin consisting of the structural units (s).

A resin other than the resin (A) and the resin (X) is preferably a resin having neither the structural unit (I) nor the structural unit (a1) but including the structural unit (a4) (which is sometimes referred to as "resin (Y)"). In the resin (Y), the proportion of the structural unit (a4) is preferably 40% by mole or more, and more preferably 45% by mole or more, and still more preferably 50% by mole or more with respect to the total structural units (100% by mole) constituting the resin (Y).

Examples of the structural unit in which the resin (Y) may further contain include the structural unit (a2), the structural unit (a3) and other structural unit derived from a known monomer.

The weight average molecular weight of the resin (Y) is preferably 8,000 or more (more preferably 10,000 or more), and 80,000 or less (more preferably 60,000 or less).

When a resist composition contain the resin (Y), the proportion thereof is preferably 1 to 60 parts by mass, more preferably 1 to 50 parts by mass, and still more preferably 1 to 40 parts by mass, in particular preferably 2 to 30 parts by mass, with respect to the resin (Y) (100 parts by mass).

The total proportion of the resins (A), (X) and (Y) is preferably 80% by mass to 99% by mass, and more preferably 90% by mass to 99% by mass, with respect to the total solid proportion of the resist composition.

<Acid Generator (B)>

The acid generator (B) may be an ionic acid generator or a non-ionic acid generator. The acid generator (B) may be used any an ionic acid generator and a non-ionic acid generator. Examples of the nonionic compounds for the acid generator include organic halogenated compounds; sulfonate esters, e.g. 2-nitrobenzylester, aromatic sulfonates, oximesulfonate, N-sulfonyloxyimide, sulfonyloxyketone, and diazonaphtoquione 4-sulfonate; sulfones, e.g., disulfone, ketosulfone, and sulfonium diazomethane. The ionic compounds for the acid generator include onium salts having an onium cation, e.g., diazonium salts, phosphonium salts, sulfonium salts and iodonium salts. Examples of the anions of onium salt include a sulfonic acid anion, a sulfonylimide anion, sulfonylmethide anion.

As the acid generator, the compounds giving an acid by radiation can be used, which are mentioned in JP63-26653A1, JP55-164824A1, JP62-69263A1, JP63-146038A1, JP63-163452A1, JP62-153853A1, JP63-146029A1, U.S. Pat. No. 3,779,778B1, U.S. Pat. No. 3,849,137B1, DE3914407 and EP126,712A1. The acid generator for the photoresist composition can be produced by the method described in the above-mentioned documents.

The acid generator is preferably a fluorine-containing compound, more preferably salt represented by the formula (B1) (which is sometimes referred to as "acid generator (B1)"):

(B1)

wherein $Q^1$ and $Q^2$ respectively represent a fluorine atom or a $C_1$ to $C_6$ perfluoroalkyl group, $L^{b1}$ represents a divalent $C_1$ to $C_{24}$ saturated hydrocarbon group where a methylene group may be replaced by an oxygen atom or a carbonyl group and where a hydrogen atom may be replaced by a hydroxyl group or fluorine atom, and Y represents an optionally substituted $C_3$ to $C_{18}$ alicyclic hydrocarbon group where a methylene group may be replaced by an oxygen atom, a carbonyl group or a sulfonyl group, and $Z^+$ represents an organic cation.

Examples of the perfluoroalkyl group of $Q^1$ and $Q^2$ include trifluoromethyl, perfluoroethyl, perfluoropropyl, perfluoro-isopropyl, perfluorobutyl, perfluoro-sec-butyl, perfluoro-tert-butyl, perfluoropentyl and perfluorohexyl groups.

$Q^1$ and $Q^2$ independently are preferably trifluoromethyl or fluorine atom, and both of $Q^1$ and $Q^2$ are preferably a fluorine atom.

Examples of the divalent saturated hydrocarbon group of $L^{b1}$ include any of a chain or a branched alkanediyl group, a divalent mono- or a poly-alicyclic saturated hydrocarbon group, and a combination thereof.

Specific examples of the chain alkanediyl group include methylene, ethylene, propane-1,3-diyl, propane-1,2-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, heptadecane-1,17-diyl groups.

Specific examples of the branched chain alkanediyl group include ethane-1,1-diyl, propane-1,1-diyl, propane-1,2-diyl, propane-2,2-diyl, pentane-1,4-diyl, pentane-2,4-diyl, 2-methylpropane-1,3-diyl, 2-methylpropane-1,2-diyl and 2-methylbutane-1,4-diyl groups.

Specific examples of the mono-alicyclic saturated hydrocarbon group include a cycloalkanediyl group such as cyclobutan-1,3-diyl, cyclopentan-1,3-diyl, cyclohexane-1,4-diyl and cyclooctan-1,5-diyl groups.

Specific examples of the poly-alicyclic saturated hydrocarbon group include norbornane-1,4-diyl, norbornane-2,5-diyl, adamantane-1,5-diyl and adamantane-2,6-diyl groups.

Examples of the saturated hydrocarbon group of $L^{b1}$ in which a methylene group has been replaced by oxygen atom or a carbonyl group include groups represented by the formula (b1-1) to the formula (b1-3) below:

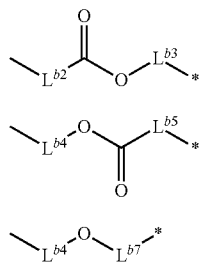

wherein $L^{b2}$ represents a single bond or a $C_1$ to $C_{22}$ divalent saturated hydrocarbon group where a hydrogen atom may be replaced by a fluorine atom;

$L^{b3}$ represents a single bond or a $C_1$ to $C_{22}$ divalent saturated hydrocarbon group where a hydrogen atom may be replaced by a fluorine atom or a hydroxy group, and a methylene group may be replaced by an oxygen atom or a carbonyl group;

provided that the total carbon number contained in the group of $L^{b2}$ and $L^{b3}$ is 22 or less;

$L^{b4}$ represents a single bond or a $C_1$ to $C_{22}$ divalent saturated hydrocarbon group where a hydrogen atom may be replaced by a fluorine atom;

$L^{b5}$ represents a single bond or a $C_1$ to $C_{22}$ divalent saturated hydrocarbon group where a hydrogen atom may be replaced by a fluorine atom or a hydroxy group, and a methylene group may be replaced by an oxygen atom or a carbonyl group;

provided that the total carbon number contained in the group of $L^{b4}$ and $L^{b5}$ is 22 or less;

$L^{b6}$ represents a single bond or a $C_1$ to $C_{23}$ divalent saturated hydrocarbon group where a hydrogen atom may be replaced by a fluorine atom or a hydroxy group;

$L^{b7}$ represents a single bond or a $C_1$ to $C_{23}$ divalent saturated hydrocarbon group where a hydrogen atom may be replaced by a fluorine atom or a hydroxy group, and a methylene group may be replaced by an oxygen atom or a carbonyl group;

provided that the total carbon number contained in the group of $L^{b6}$ and $L^{b7}$ is 23 or less, and

* represents a binding site to —Y.

In formula (b1-1) to formula (b1-3), when a methylene group has been replaced by an oxygen atom or a carbonyl group, the carbon number of the saturated hydrocarbon group corresponds to the number of the carbon atom before replacement.

Examples of the divalent saturated hydrocarbon group are the same examples as the divalent saturated hydrocarbon group of $L^{b1}$.

$L^{b2}$ is preferably a single bond.

$L^{b3}$ is preferably a $C_1$ to $C_4$ divalent saturated hydrocarbon group.

$L^{b4}$ is preferably a $C_1$ to $C_8$ divalent saturated hydrocarbon group where a hydrogen atom may be replaced by a fluorine atom.

$L^{b5}$ is preferably a single bond or a $C_1$ to $C_8$ divalent saturated hydrocarbon group.

$L^{b6}$ is preferably a single bond or a $C_1$ to $C_4$ divalent saturated hydrocarbon group where a hydrogen atom may be replaced by a fluorine atom.

$L^{b7}$ is preferably a single bond or a $C_1$ to $C_{18}$ divalent saturated hydrocarbon group where a hydrogen atom may be replaced by a fluorine atom or a hydroxy group, and where a methylene group may be replaced by an oxygen atom or a carbonyl group.

Among these, the group represented by the formula (b1-1) or the formula (b1-3) is preferred.

Examples of the divalent group represented by the formula (b1-1) include groups represented by the formula (b1-4) to the formula (b1-8) described below:

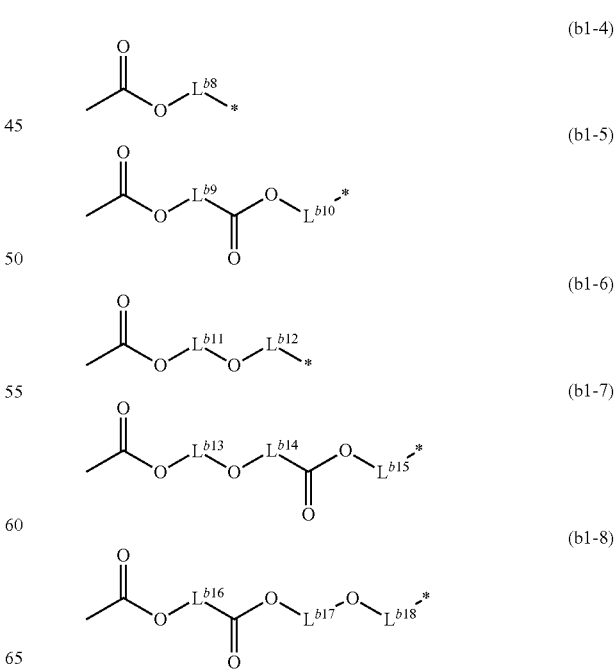

wherein $L^{b8}$ represents a single bond or a $C_1$ to $C_{22}$ divalent saturated hydrocarbon group where a hydrogen atom may be replaced by a fluorine atom or a hydroxy group;

$L^{b9}$ represents a $C_1$ to $C_{20}$ divalent saturated hydrocarbon group;

$L^{b10}$ represents a single bond or a $C_1$ to $C_{19}$ divalent saturated hydrocarbon group where a hydrogen atom may be replaced by a fluorine atom or a hydroxy group;

provided that the total carbon number contained in the group of $L^{b9}$ and $L^{b10}$ is 20 or less;

$L^{b11}$ represents a $C_1$ to $C_{21}$ divalent saturated hydrocarbon group;

$L^{b12}$ represents a single bond or a $C_1$ to $C_{20}$ divalent saturated hydrocarbon group where a hydrogen atom may be replaced by a fluorine atom or a hydroxy group;

provided that the total carbon number contained in the group of $L^{b11}$ and $L^{b12}$ is 21 or less;

$L^{b13}$ represents a $C_1$ to $C_{19}$ divalent saturated hydrocarbon group;

$L^{b14}$ represents a single bond or a $C_1$ to $C_{18}$ divalent saturated hydrocarbon group;

$L^{b15}$ represents a single bond or a $C_1$ to $C_{18}$ divalent saturated hydrocarbon group where a hydrogen atom may be replaced by a fluorine atom or a hydroxy group;

provided that the total carbon number contained in the group of $L^{b13}$, $L^{b14}$ and $L^{B15}$ is 19 or less;

$L^{b16}$ represents a $C_1$ to $C_{18}$ divalent saturated hydrocarbon group;

$L^{b17}$ represents a $C_1$ to $C_{18}$ divalent saturated hydrocarbon group;

$L^{b18}$ represents a single bond or a $C_1$ to $C_{17}$ divalent saturated hydrocarbon group where a hydrogen atom may be replaced by a fluorine atom or a hydroxy group;

provided that the total carbon number contained in the group of $L^{b16}$, $L^{b17}$ and $L^{b18}$ is 19 or less.

$L^{b8}$ is preferably a $C_1$ to $C_4$ divalent saturated hydrocarbon group.

$L^{b9}$ is preferably a $C_1$ to $C_8$ divalent saturated hydrocarbon group.

$L^{b10}$ is preferably a single bond or a $C_1$ to $C_{19}$ divalent saturated hydrocarbon group, and more preferably a single bond or a $C_1$ to $C_8$ divalent saturated hydrocarbon group.

$L^{b11}$ is preferably a $C_1$ to $C_8$ divalent saturated hydrocarbon group.

$L^{12}$ is preferably a single bond or a $C_1$ to $C_8$ divalent saturated hydrocarbon group.

$L^{b13}$ is preferably a $C_1$ to $C_{12}$ divalent saturated hydrocarbon group.

$L^{b14}$ is preferably a single bond or a $C_1$ to $C_6$ divalent saturated hydrocarbon group.

$L^{b15}$ is preferably a single bond or a $C_1$ to $C_{18}$ divalent saturated hydrocarbon group, and more preferably a single bond or a $C_1$ to $C_8$ divalent saturated hydrocarbon group.

$L^{b16}$ is preferably a $C_1$ to $C_{12}$ divalent saturated hydrocarbon group.

$L^{b17}$ is preferably a $C_1$ to $C_6$ divalent saturated hydrocarbon group.

$L^{b18}$ is preferably a single bond or a $C_1$ to $C_{17}$ divalent saturated hydrocarbon group, and more preferably a single bond or a $C_1$ to $C_4$ divalent saturated hydrocarbon group.

Examples of the divalent group represented by the formula (b1-3) include groups represented by the formula (b1-9) to the formula (b1-11) described below:

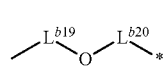
(b1-9)

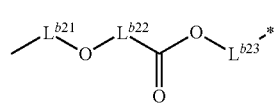
(b1-10)

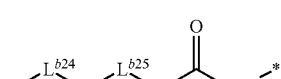
(b1-11)

wherein $L^{b19}$ represents a single bond or a $C_1$ to $C_{23}$ divalent saturated hydrocarbon group where a hydrogen atom may be replaced by a fluorine atom;

$L^{b20}$ represent a single bond or a $C_1$ to $C_{23}$ divalent saturated hydrocarbon group where a hydrogen atom may be replaced by a fluorine atom, a hydroxy group or an acyloxy group, and a methylene group contained in an acyloxy group may be replaced by an oxygen atom or a carbonyl group, and a hydrogen atom contained in an acyloxy group may be replaced by a hydroxy group, provided that the total carbon number contained in the group of $L^{b19}$ and $L^{b20}$ is 23 or less;

$L^{b21}$ represents a single bond or a $C_1$ to $C_{21}$ divalent saturated hydrocarbon group where a hydrogen atom may be replaced by a fluorine atom;

$L^{b22}$ represents a single bond or a $C_1$ to $C_{21}$ divalent saturated hydrocarbon group;

$L^{b23}$ represents a single bond or a $C_1$ to $C_{21}$ divalent saturated hydrocarbon group where a hydrogen atom may be replaced by a fluorine atom, a hydroxy group or an acyloxy group, and a methylene group contained in an acyloxy group may be replaced by an oxygen atom or a carbonyl group, and a hydrogen atom contained in an acyloxy group may be replaced by a hydroxy group, provided that the total carbon number contained in the group of $L^{b21}$, $L^{b22}$ and $L^{b23}$ is 21 or less;

$L^{b24}$ represents a single bond or a $C_1$ to $C_{20}$ divalent saturated hydrocarbon group where a hydrogen atom may be replaced by a fluorine atom;

$L^{b25}$ represents a single bond or a $C_1$ to $C_{21}$ divalent saturated hydrocarbon group;

$L^{b26}$ represents a single bond or a $C_1$ to $C_{20}$ divalent saturated hydrocarbon group where a hydrogen atom may be replaced by a fluorine atom, a hydroxy group or an acyloxy group, and a methylene group contained in an acyloxy group may be replaced by an oxygen atom or a carbonyl group, and a hydrogen atom contained in an acyloxy group may be replaced by a hydroxy group, provided that the total carbon number contained in the group of $L^{b24}$, $L^{b025}$ and $L^{b26}$ is 21 or less.

In formula (b1-9) to formula (b1-11), when a hydrogen atom has been replaced by an acyloxy group, the carbon number of the saturated hydrocarbon group corresponds to the number of the carbon atom, CO and O in addition to the carbon number of the saturated hydrocarbon group.

For formula (b1-9) to formula (b1-11), examples of the divalent saturated hydrocarbon group include an alkanediyl and a monocyclic or polycyclic divalent saturated hydrocarbon group, and a combination of two or more such groups.

Examples of the acyloxy group include acetyloxy, propionyloxy, butyryloxy, cyclohexyl carbonyloxy and adamantyl carbonyloxy groups.

Examples of the acyloxy group having a substituent include oxoadamantyl carbonyloxy, hydroxyadamanty carbonyloxy, oxocyclohexy carbonyloxy and hydroxycyclohexy carbonyloxy groups.

Examples of the group represented by the formula (b1-4) include the following ones.

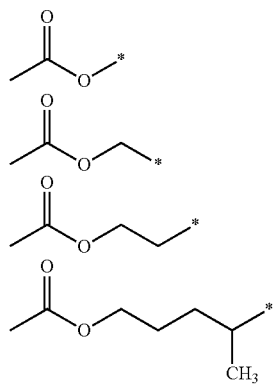

Examples of the group represented by the formula (b1-5) include the following ones.

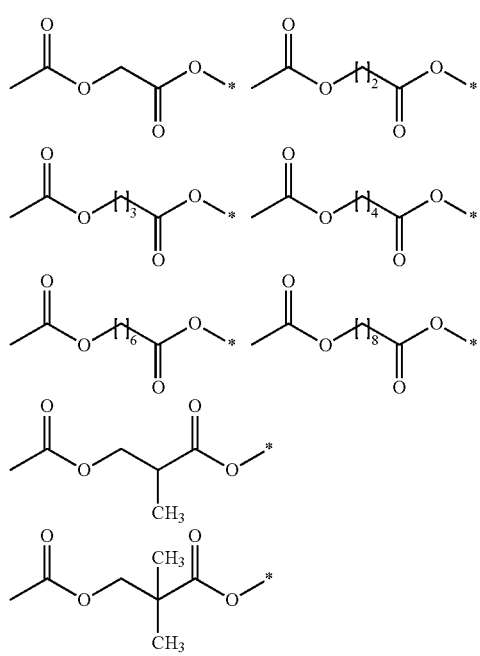

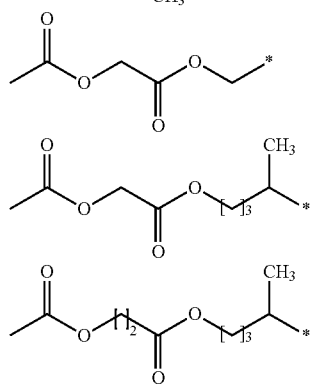

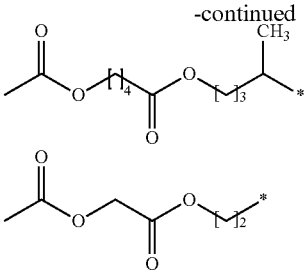

Examples of the group represented by the formula (b1-6) include the following ones.

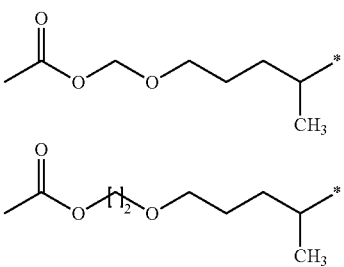

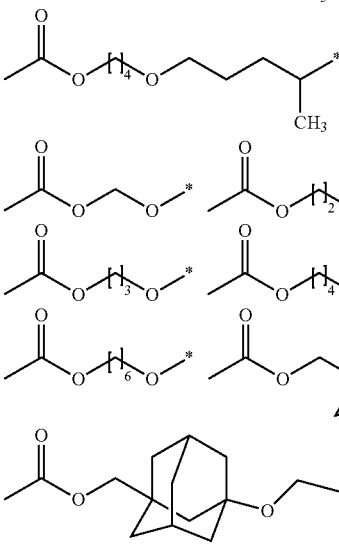

Examples of the group represented by the formula (b1-7) include the following ones.

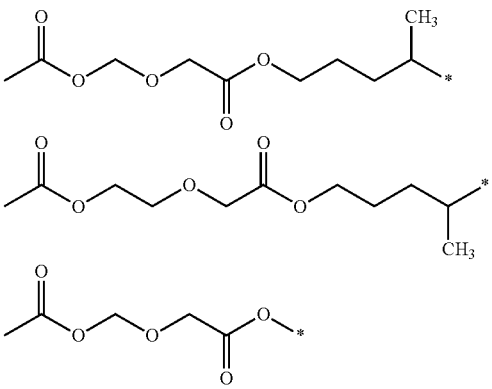

-continued
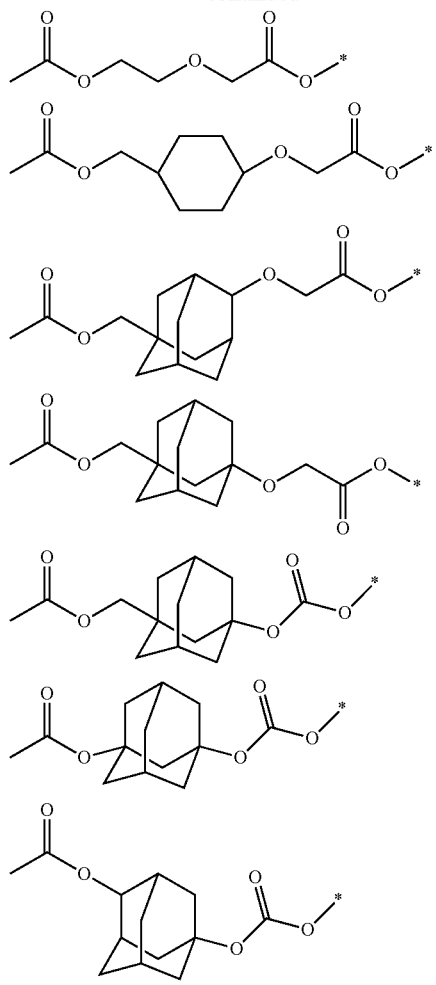
Examples of the group represented by the formula (b1-8) include the following ones.
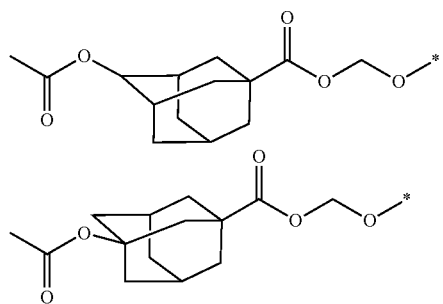
Examples of the group represented by the formula (b1-2) include the following ones.
-continued
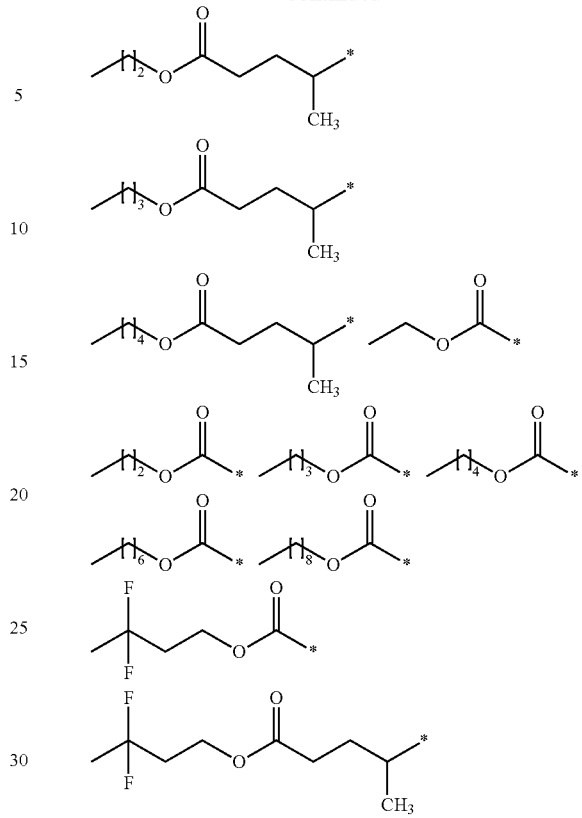
Examples of the group represented by the formula (b1-9) include the following ones.
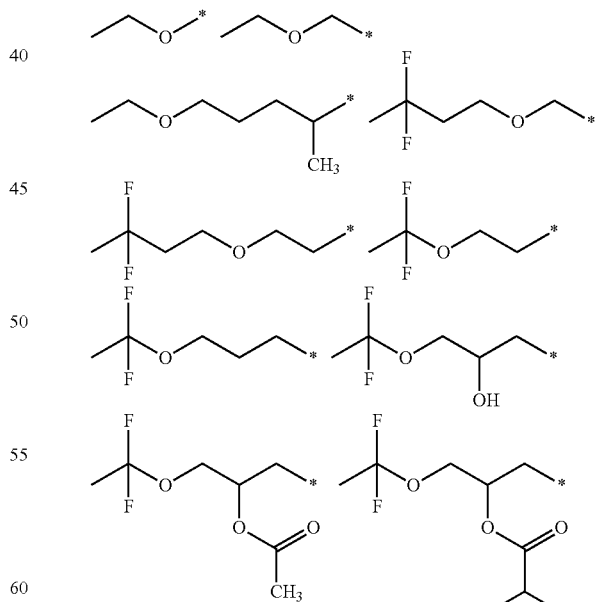
Examples of the group represented by the formula (b1-10) include the following ones.

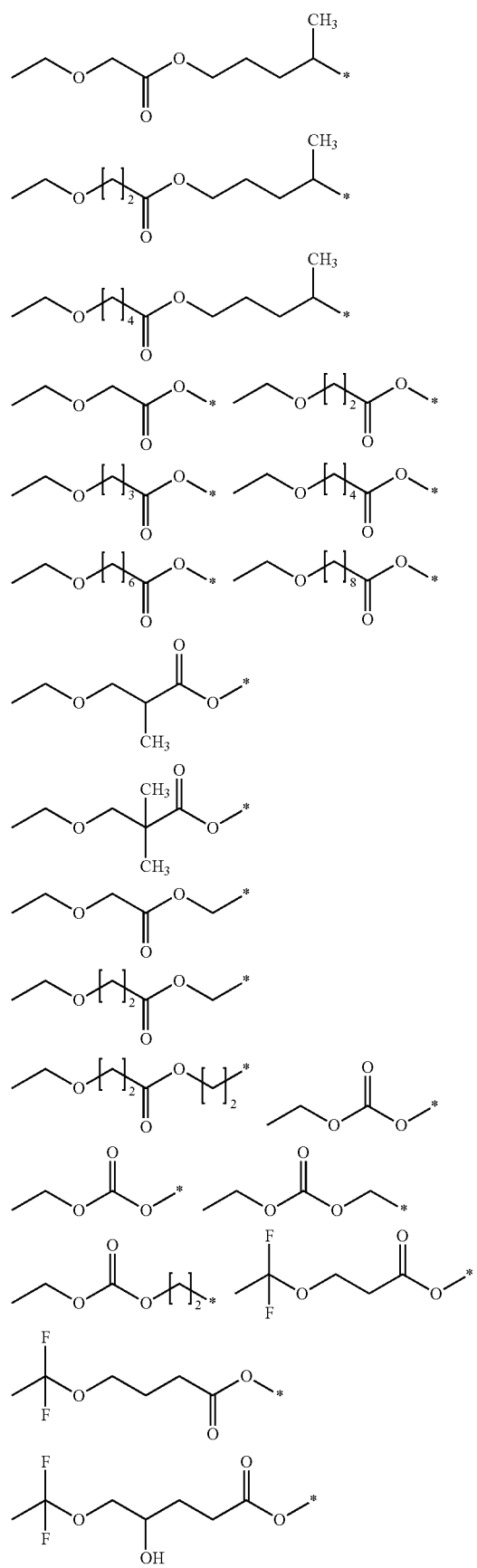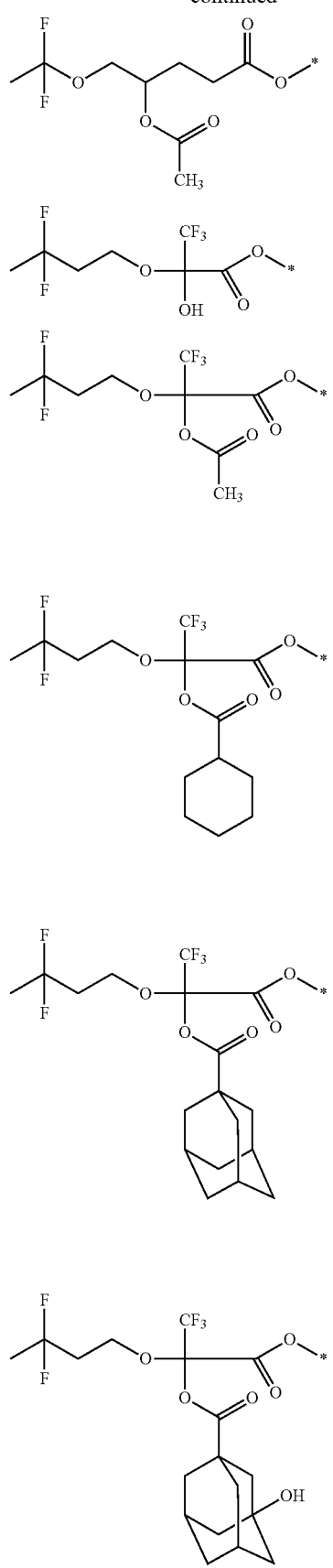

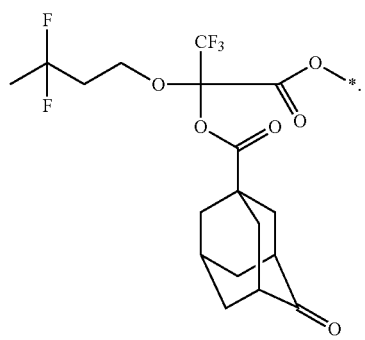
Examples of the group represented by the formula (b1-11) include the following ones.
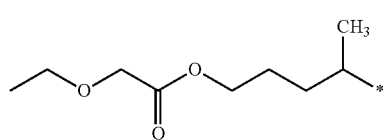
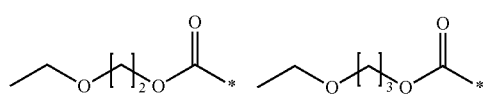
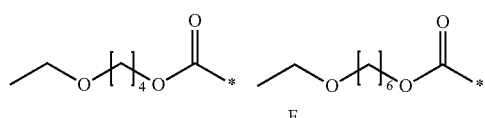
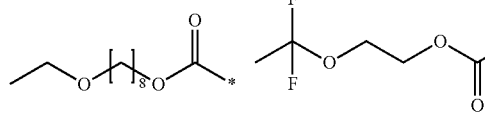
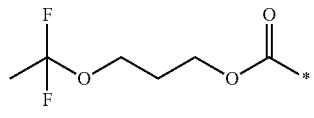
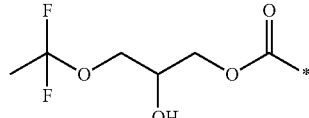
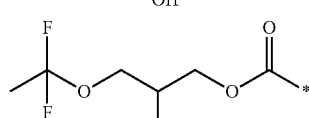
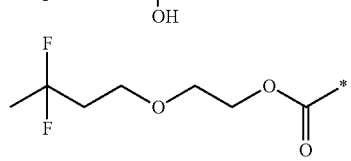
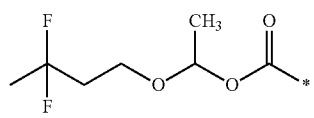
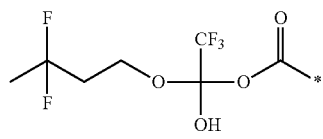
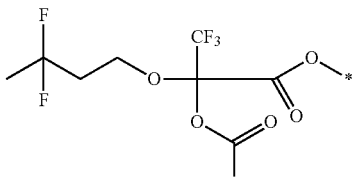
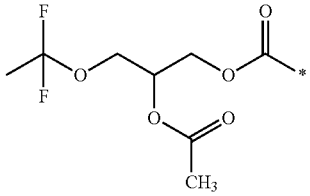
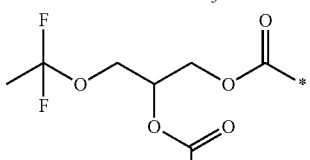
Examples of the monovalent alicyclic hydrocarbon group of Y include groups represented by the formula (Y1) to the formula (Y11).

Examples of the monovalent alicyclic hydrocarbon group of Y in which a methylene group has been replaced by an oxygen atom, a carbonyl group or a sulfonyl group include groups represented by the formula (Y12) to the formula (Y27).
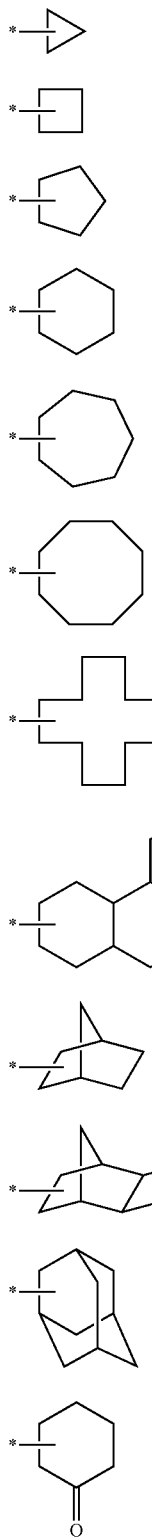
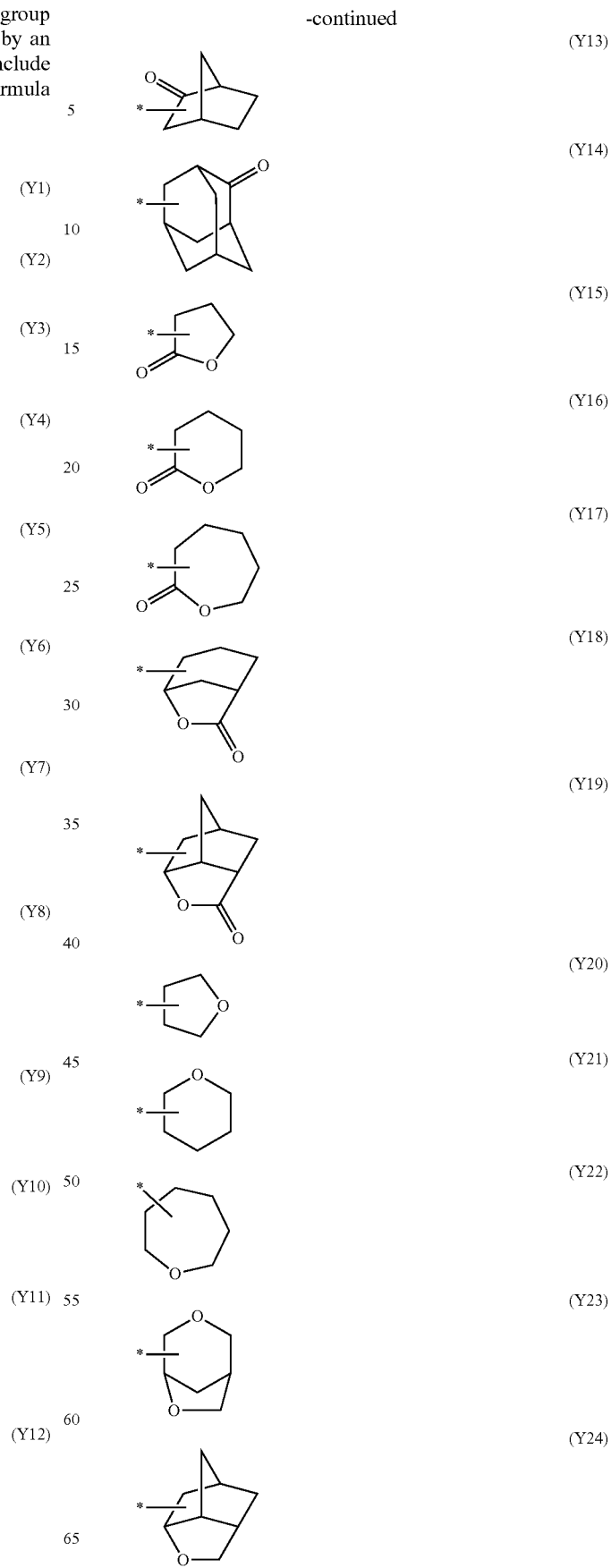

-continued (Y25)

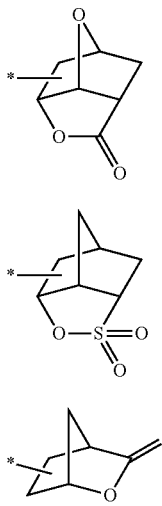

(Y26)

(Y27)

Among these, the alicyclic hydrocarbon group is preferably any one of groups represented by the formula (Y1) to the formula (Y19), more preferably any one of groups represented by the formula (Y11), (Y14), (Y15) or (Y19), and still more preferably group represented by the formula (Y11) or (Y14).

Examples of the substituent for the alicyclic group represented by Y include a halogen atom, a hydroxyl group, a $C_1$ to $C_{12}$ alkyl group, a hydroxy group-containing $C_1$ to $C_{12}$ alkyl group, a $C_3$ to $C_{16}$ monovalent alicyclic hydrocarbon group, a $C_i$ to $C_{12}$ alkoxy group, a $C_6$ to $C_{18}$ monovalent aromatic hydrocarbon group, a $C_7$ to $C_{21}$ aralkyl group, a $C_2$ to $C_4$ acyl group, a glycidyloxy group and —$(CH_2)_{j2}$—O—CO—$R^{b1}$— in which $R^{b1}$ represents an $C_1$ to $C_{16}$ alkyl group, a $C_3$ to $C_{16}$ monovalent alicyclic hydrocarbon group, or a $C_6$ to $C_{18}$ monovalent aromatic hydrocarbon group, and j2 represents an integer of 0 to 4.

Examples of the hydroxy group-containing alkyl group include hydroxymethyl and hydroxyethyl groups Examples of the alkoxyl group include methoxy, ethoxy, propoxy, butoxy, pentyloxy, hexyloxy, heptyloxy, octyloxy, decyloxy and dodecyloxy groups.

Examples of the monovalent aromatic hydrocarbon group include an aryl group such as phenyl, naphthyl, anthryl, p-methylphenyl, p-tert-butylphenyl, p-adamantylphenyl, tolyl, xylyl, cumenyl, mesityl, biphenyl, phenanthryl, 2,6-diethylphenyl and 2-methyl-6-ethylphenyl groups.

Examples of the aralkyl group include benzyl, phenethyl, phenylpropyl, naphthylmethyl and naphthylethyl groups.

Examples of the acyl group include acetyl, propionyl and butyryl groups.

Examples of the halogen atom include fluorine, chlorine, bromine and iodine atoms.

Examples of Y include the groups below. * represents a binding site to $L^{b1}$.

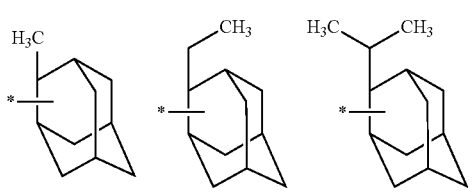

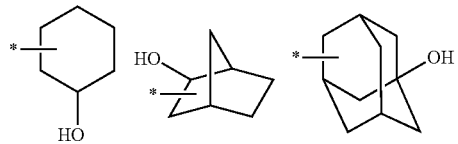

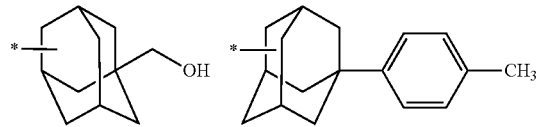

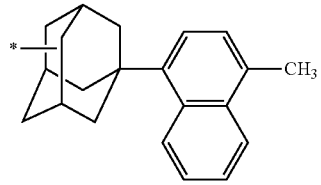

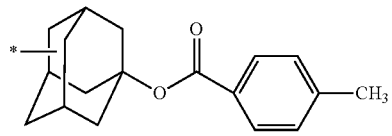

Y is preferably a $C_3$ to $C_{18}$ monovalent alicyclic hydrocarbon group which may have a substituent, more preferably an adamantyl group which may have a substituent and one or more methylene group contained in the adamantyl group may be replaced with an oxygen atom, a carbonyl group or a sufonyl group, and still more preferably an adamantyl group, a hydroxyadamantyl group or an oxoadamantyl group.

The sulfonic acid anion in the salt represented by the formula (B1) is preferably an anions represented by the formula (B1-A-1) to the formula (B1-A-33), and more preferably an anions represented by the formula (B1-A-1) to the formula (B1-A-4), the formula (B1-A-9), the formula (B1-A-10), the formula (B1-A-24) to the formula (B1-A-33), below.

In the formula (B1-A-1) to the formula (B1-A-33), $R^{i2}$ to $R^{i7}$ independently represent, for example, a $C_1$ to $C_4$ alkyl group, and preferably methyl or ethyl group, $R^{i8}$ represent, for example, a $C_1$ to $C_{12}$ aliphatic hydrocarbon group, preferably a $C_1$ to $C_4$ alkyl group, a $C_5$ to $C_{12}$ monovalent alicyclic hydrocarbon group or a group formed by a combination thereof, more preferably a methyl, ethyl group, cyclohexyl group or adamantyl group. $L^4$ represents a single bond or a $C_1$ to $C_4$ alkanediyl group. $Q^1$ and $Q^2$ represent the same meaning as defined above.

Specific examples of the sulfonic acid anion in the salt represented by the formula (B1) include anions mentioned in JP2010-204646A1.

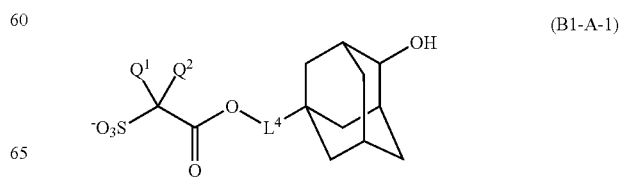

(B1-A-1)

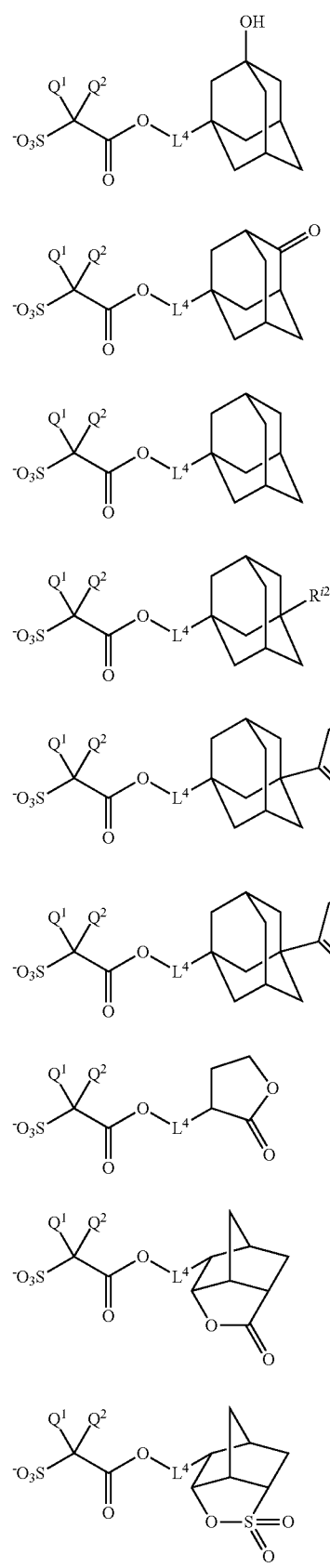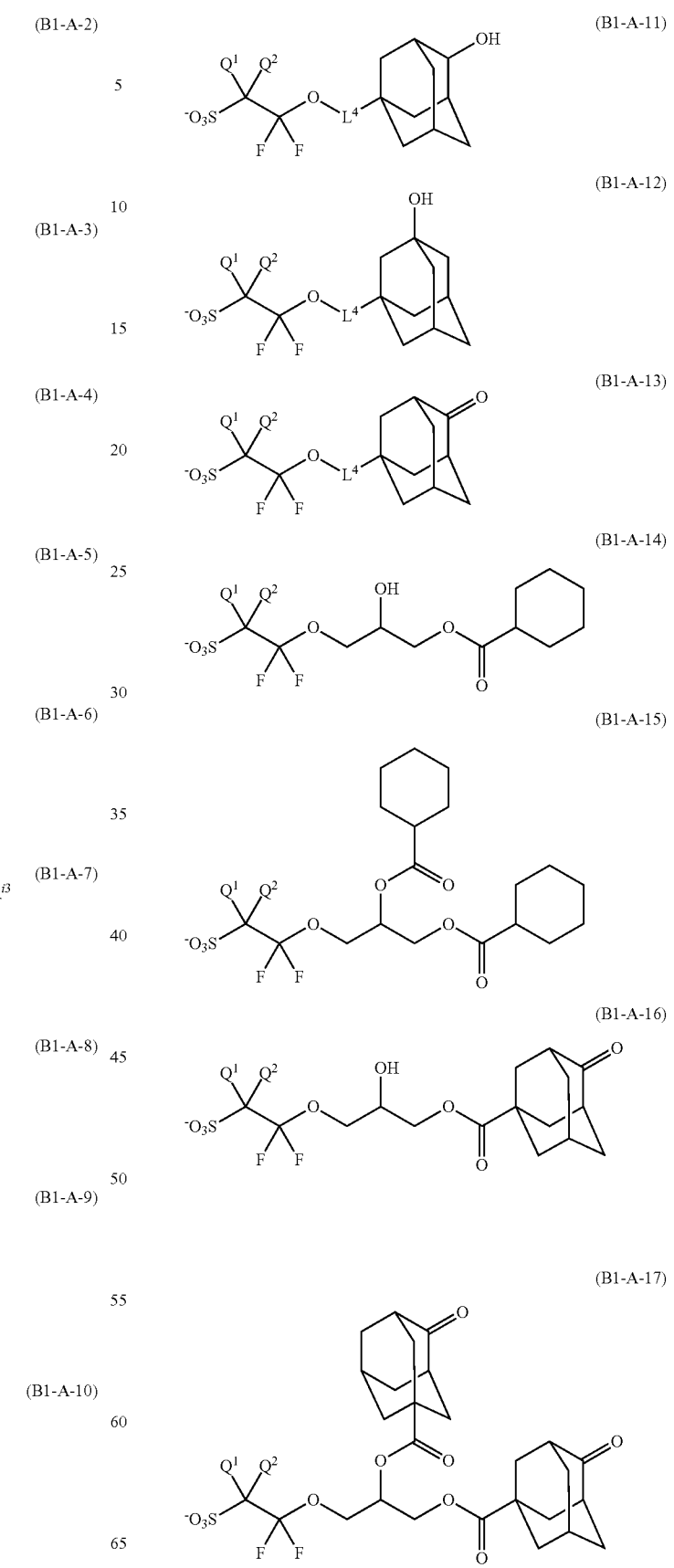

(B1-A-18)
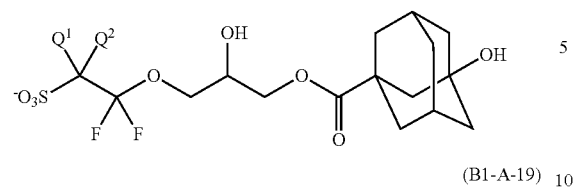
(B1-A-19)
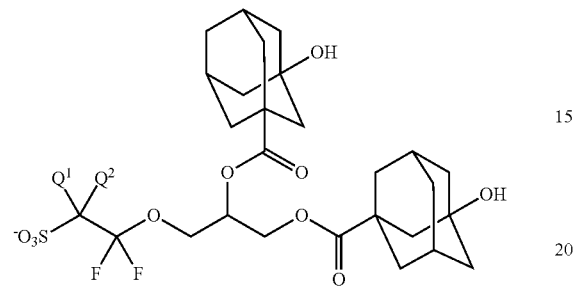
(B1-A-20)
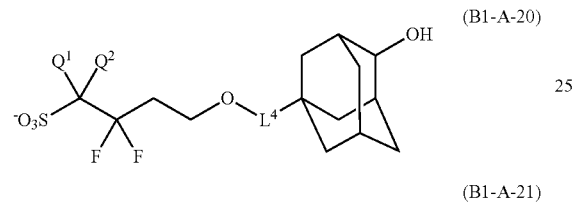
(B1-A-21)
(B1-A-22)
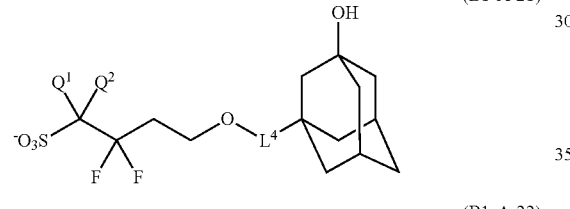
(B1-A-23)
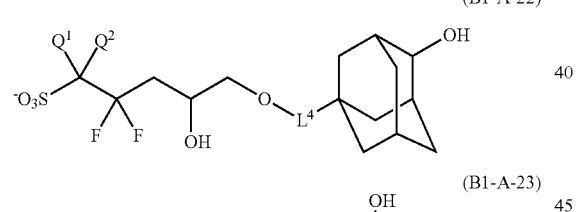
(B1-A-24)
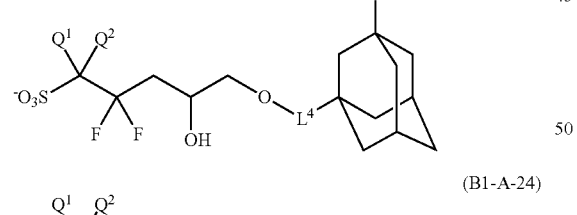
(B1-A-25)
(B1-A-26)
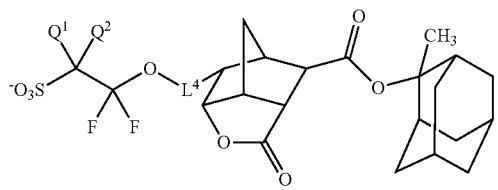
(B1-A-27)
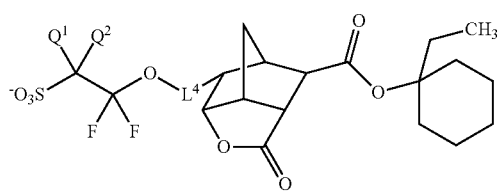
(B1-A-28)
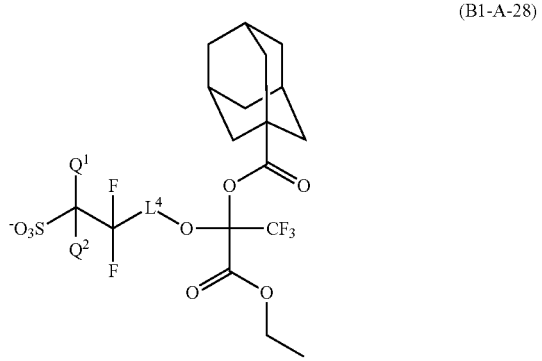
(B1-A-29)
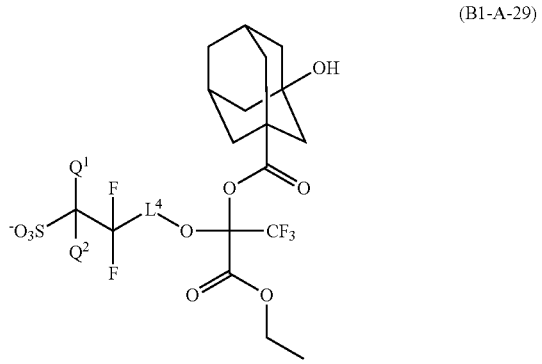
(B1-A-30)
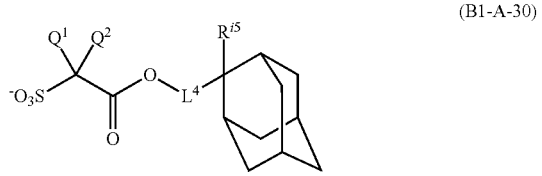
(B1-A-31)
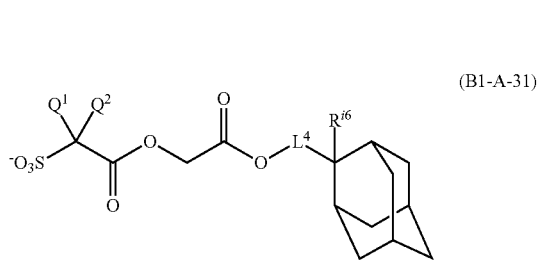

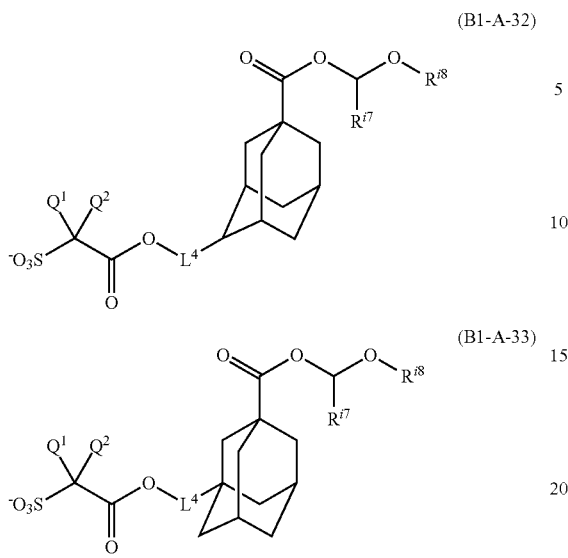
Among these, preferred examples of the sulfonic acid anion for the salt represented by the formula (B1) include anions represented by the formulae (B1a-1) to (B1a-15).
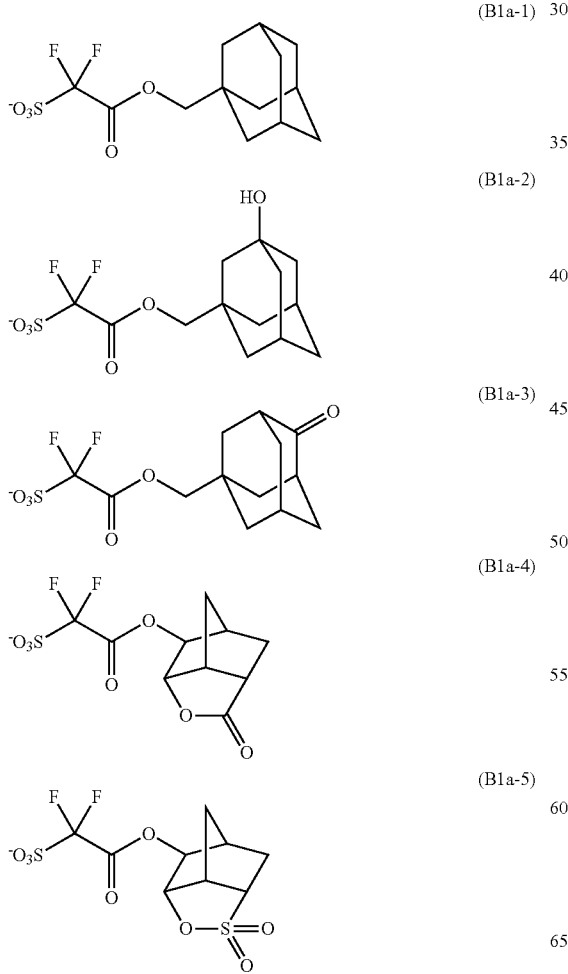
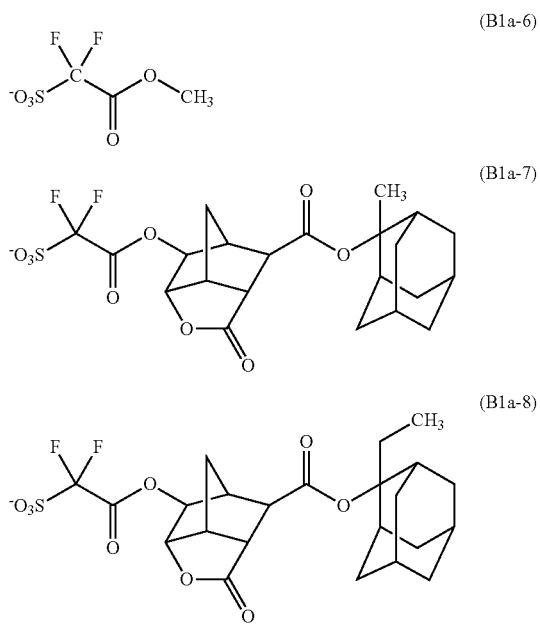

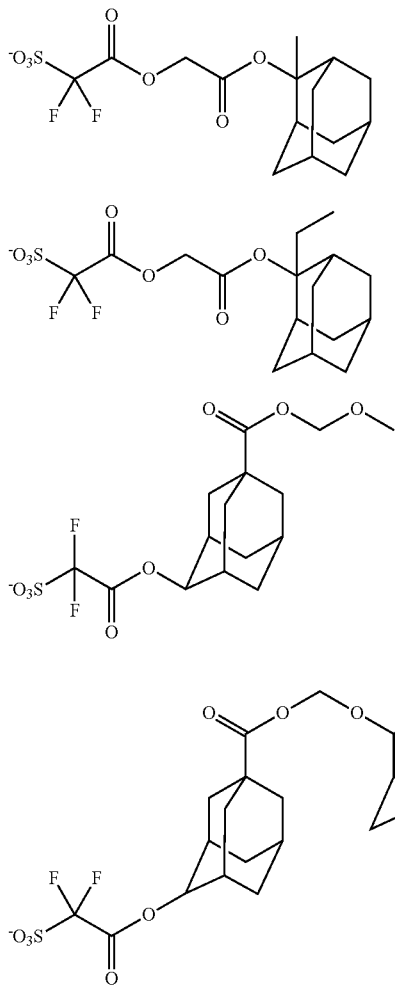

Among them, preferred examples of the sulfonic acid anion include anions represented by the formulae (B1a-1) to (B1a-3) and (B1a-7) to (B1a-15).

Examples of the organic cation represented by Z⁺ include an organic onium cation such as an organic sulfonium cation, an organic iodonium cation, an organic ammonium cation, a benzothiazolium cation and an organic phosphonium cation, and an organic sulfonium cation and an organic iodonium cation are preferred, and an arylsulfonium cation is more preferred.

Z⁺ of the formula (B1) is preferably represented by any of the formula (b2-1) to the formula (b2-4):

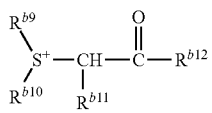

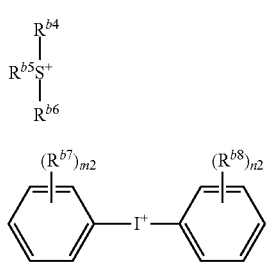

wherein $R^{b4}$, $R^{b5}$ and $R^{b6}$ independently represent a $C_1$ to $C_{30}$ aliphatic hydrocarbon group, a $C_3$ to $C_{36}$ alicyclic hydrocarbon group or a $C_6$ to $C_{36}$ aromatic hydrocarbon group, a hydrogen atom contained in an aliphatic hydrocarbon group may be replaced by a hydroxy group, a $C_1$ to $C_{12}$ alkoxy group, a $C_3$ to $C_{12}$ alicyclic hydrocarbon group or a $C_6$ to $C_{18}$ aromatic hydrocarbon group, a hydrogen atom contained in an alicyclic hydrocarbon group may be replaced by a halogen atom, a $C_1$ to $C_{18}$ aliphatic hydrocarbon group, a $C_2$ to $C_4$ acyl group or a glycidyloxy group, a hydrogen atom contained in an aromatic hydrocarbon group may be replaced by a halogen atom, a hydroxy group or a $C_1$ to $C_{12}$ alkoxy group, or $R^{b4}$ and $R^{b5}$ may be bonded together with a sulfur atom bonded thereto to form a sulfur-containing ring, a methylene group contained in the ring may be replaced by an oxygen atom, a sulfur atom or a carbonyl group;

$R^{b7}$ and $R^{b8}$ in each occurrence independently represent a hydroxy group, a $C_1$ to $C_{12}$ aliphatic hydrocarbon group or a $C_1$ to $C_{12}$ alkoxy group, m2 and n2 independently represent an integer of 0 to 5;

$R^{b9}$ and $R^{b10}$ independently represent a $C_1$ to $C_{36}$ aliphatic hydrocarbon group or a $C_3$ to $C_{36}$ alicyclic hydrocarbon group, or $R^{b9}$ and $R^{b10}$ may be bonded together with a sulfur atom bonded thereto to form a sulfur-containing ring, and a methylene group contained in the ring may be replaced by an oxygen atom, sulfur atom or a carbonyl group;

$R^{b11}$ represents a hydrogen atom, a $C_1$ to $C_{36}$ aliphatic hydrocarbon group, a $C_3$ to $C_{36}$ alicyclic hydrocarbon group or a $C_6$ to $C_{18}$ aromatic hydrocarbon group;

$R^{b12}$ represents a $C_1$ to $C_{12}$ aliphatic hydrocarbon group, a $C_3$ to $C_{18}$ alicyclic hydrocarbon group and a $C_6$ to $C_{18}$ aromatic hydrocarbon group, a hydrogen atom contained in an aliphatic hydrocarbon group may be replaced by a $C_6$ to $C_{18}$ aromatic hydrocarbon group, and a hydrogen atom contained in an aromatic hydrocarbon group may be replaced by a $C_1$ to $C_{12}$ alkoxy group or a $C_1$ to $C_{12}$ alkyl carbonyloxy group;

$R^{b11}$ and $R^{b12}$ may be bonded together with —CH—CO— bonded thereto to form a ring, and a methylene group contained in the ring may be replaced by an oxygen atom, sulfur atom or a carbonyl group;

$R^{b13}$, $R^{b14}$, $R^{b15}$, $R^{b16}$, $R^{b17}$ and $R^{b18}$ in each occurrence independently represent a hydroxy group, a $C_1$ to $C_{12}$ aliphatic hydrocarbon group or a $C_1$ to $C_{12}$ alkoxy group;

$L^{b13}$ represents —S— or —O—;

o2, p2, s2 and t2 independently represent an integer of 0 to 5;

q2 or r2 independently represent an integer of 0 to 4; and u2 represents an integer of 0 or 1.

Examples of the aliphatic group preferably include methyl, ethyl, n-propyl, isopropyl, n-butyl, sec-butyl, tert-butyl, n-pentyl, n-hexyl, n-octyl and 2-ethylhexyl groups. Among these, the aliphatic hydrocarbon group of $R^{b9}$ to $R^{b12}$ is preferably a $C_1$ to $C_{12}$ aliphatic hydrocarbon group.

Examples of the alicyclic hydrocarbon group preferably include monocyclic groups such as a cycloalkyl group, i.e., cyclopropyl, cyclobutyl, cyclopentyl, cyclohexyl, cycloheptyl, cyclooctyl, cyclodecyl groups; and polycyclic hydrocarbon groups such as decahydronaphtyl, adamantyl and norbornyl groups as well as groups below.

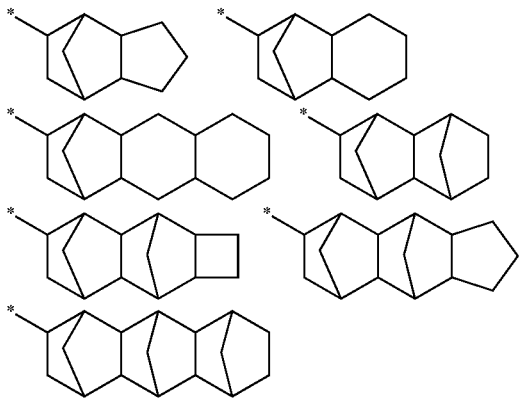

Among these, the alicyclic hydrocarbon group of $R^{b9}$ to $R^{b12}$ is preferably a $C_3$ to $C_{18}$ alicyclic group, and more preferably a $C_4$ to $C_{12}$ alicyclic hydrocarbon group.

Examples of the alicyclic hydrocarbon group where a hydrogen atom may be replaced by an aliphatic hydrocarbon group include methylcyclohexyl, dimethylcyclohexyl, 2-alkyladamantane-2-yl, methylnorbornyl and isobornyl groups. In the alicyclic hydrocarbon group where a hydrogen atom may be replaced by an aliphatic hydrocarbon group, the total carbon number of the alicyclic hydrocarbon group and the aliphatic hydrocarbon group is preferably 20 or less.

Examples of the aromatic hydrocarbon group preferably include an aryl group such as phenyl, tolyl, xylyl, cumenyl, mesityl, p-ethylphenyl, p-tert-butylphenyl, p-cyclohexylphenyl, p-adamantylphenyl, biphenyl, naphthyl, phenanthryl, 2,6-diethylphenyl and 2-methyl-6-ethylphenyl groups.

When the aromatic hydrocarbon includes an aliphatic hydrocarbon group or an alicyclic hydrocarbon group, a $C_1$ to $C_{18}$ aliphatic hydrocarbon group or a $C_3$ to $C_{18}$ alicyclic hydrocarbon group is preferred.

Examples of the aromatic hydrocarbon group where a hydrogen atom may be replaced by an alkoxy group include a p-methoxyphenyl group.

Examples of the aliphatic hydrocarbon group where a hydrogen atom may be replaced by an aromatic hydrocarbon group include an aralkyl group such as benzyl, phenethyl phenylpropyl, trityl, naphthylmethyl and naphthylethyl groups.

Examples of the alkoxy group include methoxy, ethoxy, propoxy, butoxy, pentyloxy, hexyloxy, heptyloxy, octyloxy, and dodecyloxy groups.

Examples of the acyl group include acetyl, propionyl and butyryl groups.

Examples of the halogen atom include fluorine, chlorine, bromine and iodine atoms.

Examples of the alkylcarbonyloxy group include methylcarbonyloxy, ethylcarbonyloxy, n-propylcarbonyloxy, isopropylcarbonyloxy, n-butylcarbonyloxy, sec-butylcarbonyloxy, tert-butyl carbonyloxy, pentylcarbonyloxy, hexylcarbonyloxy, octylcarbonyloxy and 2-ethylhexylcarbonyloxy groups.

The sulfur atom-containing ring which is formed by $R^{b4}$ and $R^{b5}$ may be a monocyclic or polycyclic one, which may be an aromatic or non-aromatic one, and which may be a saturated or unsaturated one. The ring is preferably a ring having 3 to 18 carbon atoms, and more preferably a ring having 4 to 13 carbon atoms. Examples of the sulfur atom-containing ring include a 3- to 12-membered ring, preferably a 3- to 7-membered ring, examples thereof include rings below.

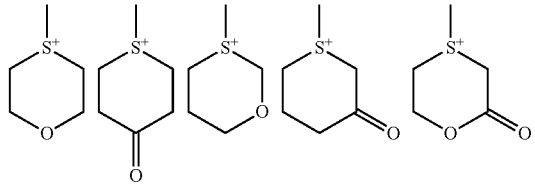

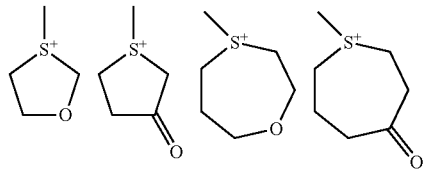

Examples of the ring formed by $R^{b9}$ and $R^{b10}$ may be any of monocyclic, polycyclic, aromatic, non-aromatic, saturated and unsaturated rings. The ring may be a 3- to 12-membered ring, preferably a 3- to 7-membered ring. Examples of the ring include thiolane-1-ium ring (tetrahydrothiophenium ring), thian-1-ium ring and 1,4-oxathian-4-ium ring.

Examples of the ring formed by $R^{b11}$ and $R^{b12}$ may be any of monocyclic, polycyclic, aromatic, non-aromatic, saturated and unsaturated rings. The ring may be a 3- to 12-membered ring, preferably a 3- to 7-membered ring. Examples of the ring include oxocycloheptane ring, oxocyclohexane ring, oxonorbornane ring and oxoadamantane ring.

Among the cations represented by the formula (b2-1) to the formula (b2-4), the cation represented by the formula (b2-1) is preferred, the cation represented by the formula (b2-1-1) is more preferred, and triphenyl sulfonium cation (v2=w2=x2=0 in the formula (b2-1-1)), diphenyl sulfonium cation (v2=w2=0, x2=1, and $R^{b21}$ is a methyl group in the formula (b2-1-1)), and tritolyl sulfonium cation (v2=w2=x2=1, $R^{b19}$, $R^{b20}$ and $R^{b21}$ are a methyl group in the formula (b2-1-1)) are still more preferred:

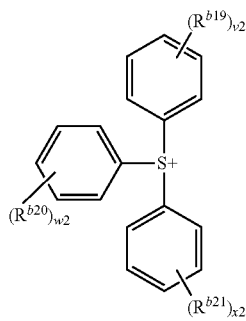

(b2-1-1)

wherein $R^{b19}$, $R^{b20}$ and $R^{b21}$ in each occurrence independently represent a halogen atom, a hydroxy group, a $C_1$ to $C_{18}$ aliphatic hydrocarbon group, a $C_3$ to $C_{18}$ alicyclic hydrocarbon group or a $C_1$ to $C_{12}$ alkoxy group, or two of $R^{b19}$, $R^{b20}$ and $R^{b21}$ may be bonded together to form a sulfur-containing ring.

In the formula (b2-1-1), the sulfur-containing ring formed by two of $R^{b19}$, $R^{b20}$ and $R^{b21}$ may be monocyclic or polycyclic ring. The ring may be aromatic or non-aromatic ring. The ring may be saturated or unsaturated ring. The ring may have afurther more sulfur atom and/or an oxygen atom.

The alkyl group of $R^{b19}$, $R^{b20}$ and $R^{b21}$ is preferably a $C_1$ to $C_{12}$ aliphatic hydrocarbon group. The alicyclic hydrocarbon group of $R^{b19}$, $R^{b20}$ and $R^{b21}$ is preferably a $C_4$ to $C_{18}$ alicyclic hydrocarbon group, $R^{b19}$, $R^{b20}$ and $R^{b21}$ each independently preferably represent a halogen atom (and more preferably fluorine atom), a hydroxy group, a $C_1$ to $C_{12}$ aliphatic hydrocarbon group or a $C_1$ to $C_{12}$ alkoxy group; or two of $R^{b19}$, $R^{b20}$ and $R^{b21}$ preferably are bonded together to form a sulfur-containing ring, and v2, w2 and x2 independently represent preferably 0 or 1.

Specific examples of the organic cations represented by the formula (b2-1) to the formula (b2-4) and the formula (b2-1-1) include, for example, compounds described in JP2010-204646A.

The acid generator (B1) is generally a compound which consists of the above sulfonate anion with an organic cation. The above sulfonic acid anion and the organic cation may optionally be combined. Preferred combination is a combination of any of the anion represented by the formula (B1a-1) to the formula (B1a-3), the formula (B1a-7) to the formula (B1a-15) and the cation represented by the formula (b2-1-1) or the formula (b2-3).

Preferred acid generators (B1) are represented by the formula (B1-1) to the formula (B1-30). Among these, the formulae (B1-1), (B1-2), (B1-3), (B1-5), (B1-6), (B1-7), (B1-11), (B1-12), (B1-13), (B1-14), (B1-17), (B1-20), (B1-21), (B1-23), (B1-24), (B1-25), (B1-26) and (B1-29) which contain arylsulfonium cation are preferred.

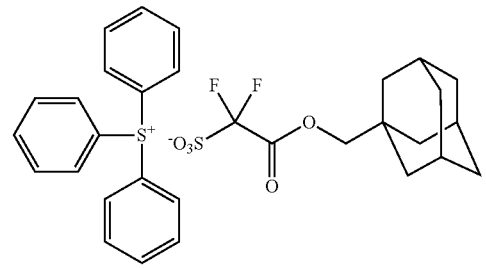

(B1-1)

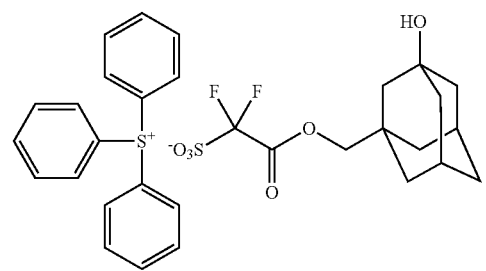

(B1-2)

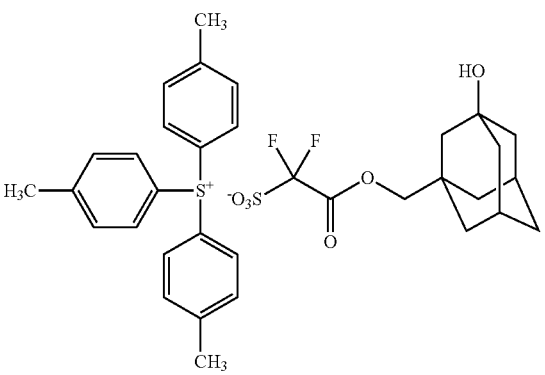

(B1-3)

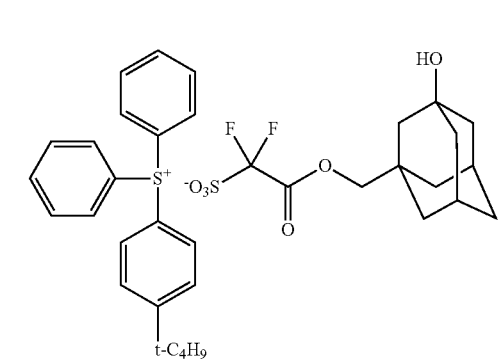

(B1-4)

(B1-5)
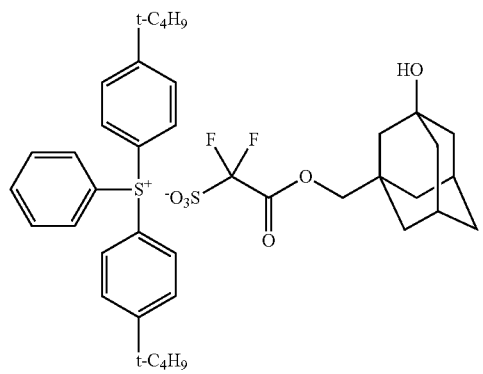
(B1-6)
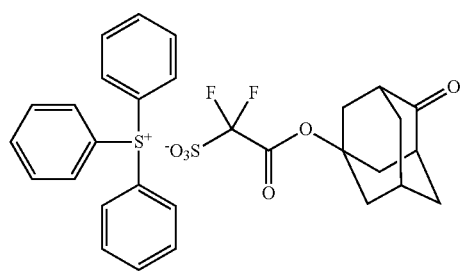
(B1-7)
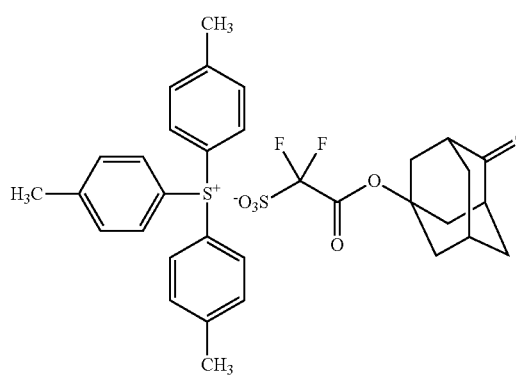
(B1-8)
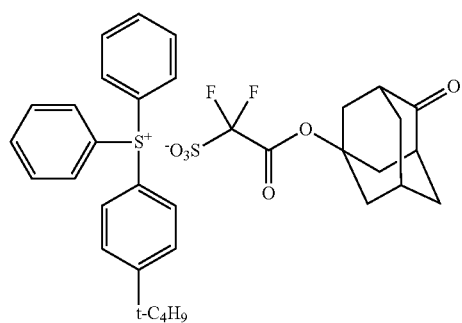
(B1-9)
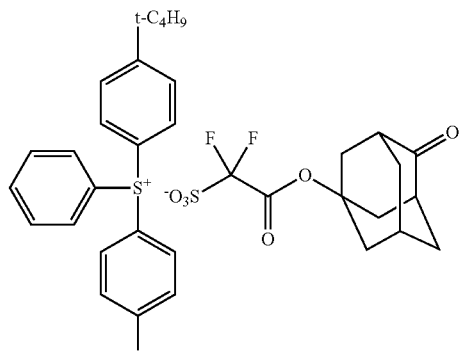
(B1-10)
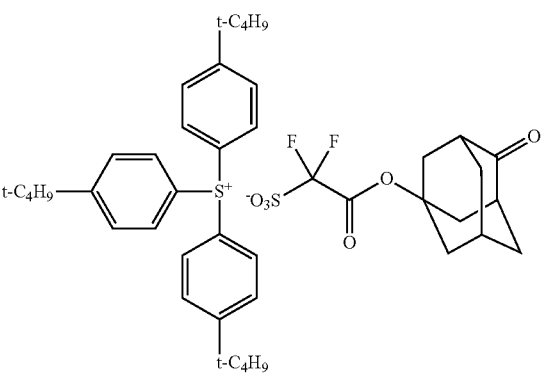
(B1-11)
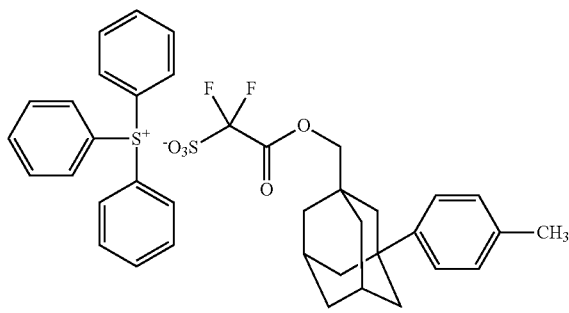
(B1-12)
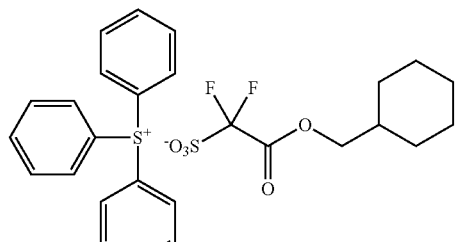
(B1-13)
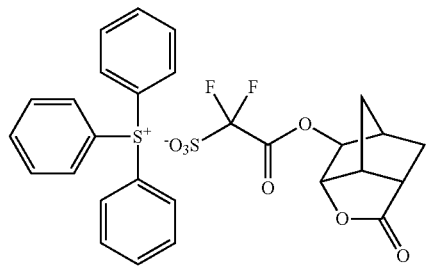

(B1-14)
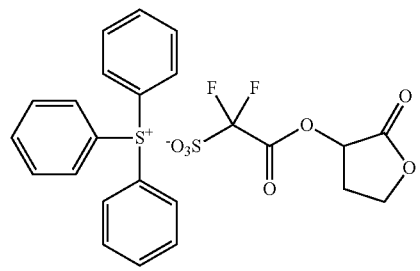
(B1-15)
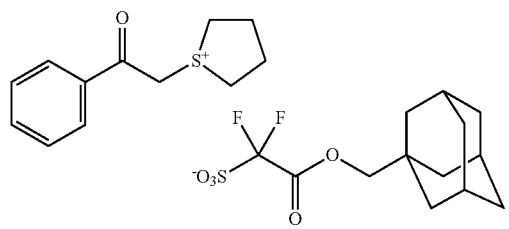
(B1-16)
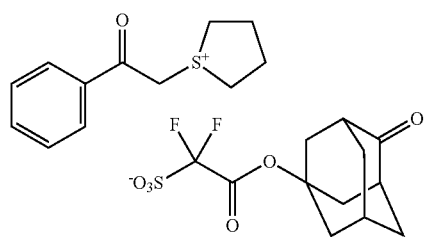
(B1-17)
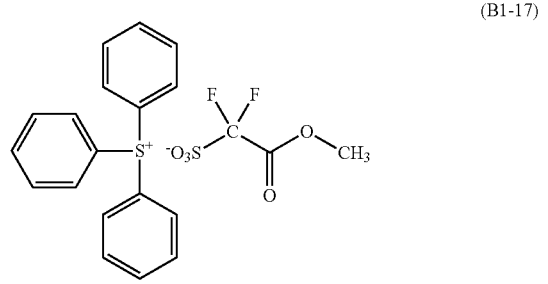
(B1-18)
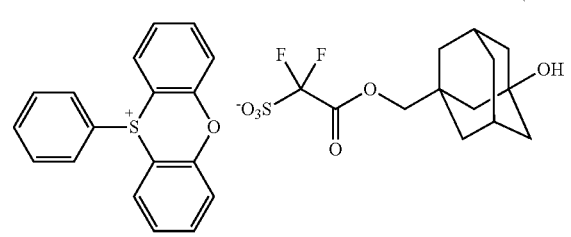
(B1-19)
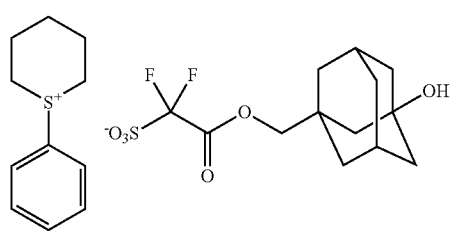
(B1-20)
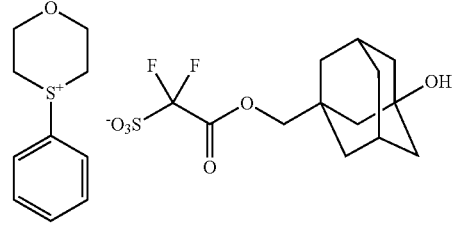
(B1-21)
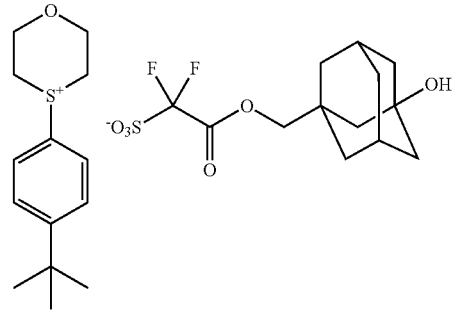
(B1-22)
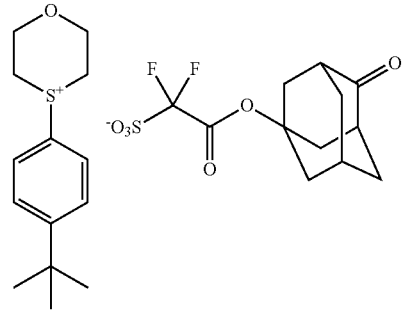
(B1-23)
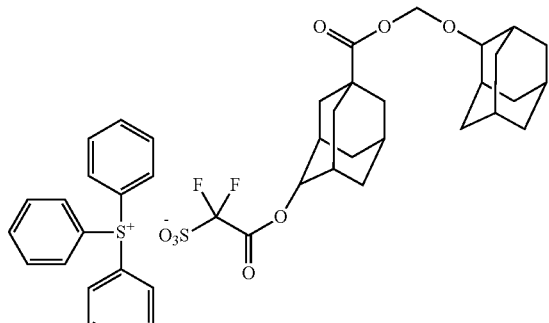
(B1-24)
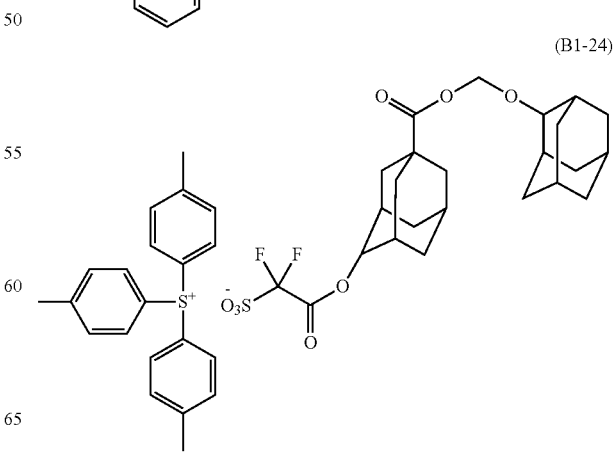

(B1-25)
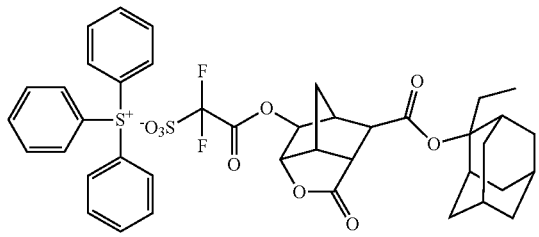

(B1-26)
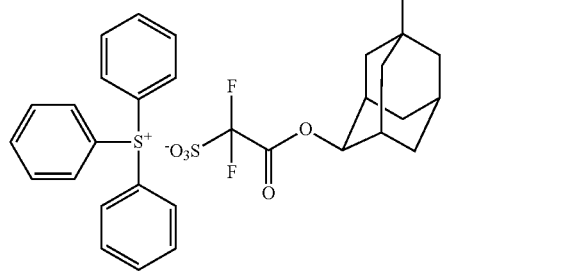

(B1-27)
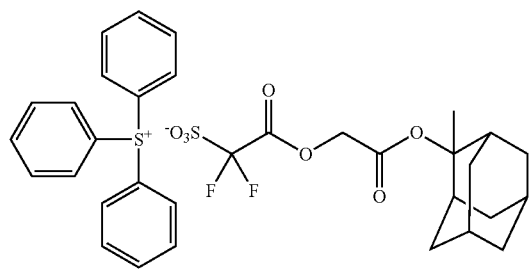

(B1-28)
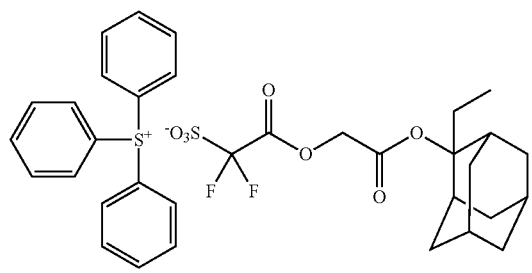

(B1-29)
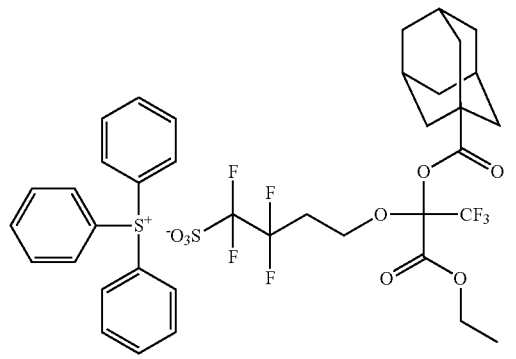

(B1-30)
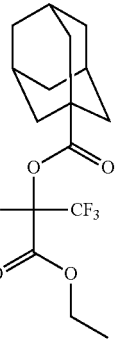

The proportion of the acid generator (B1) is preferably 30% by mass or more, and 100% by mass or less, more preferably 50% by mass or more, and 100% by mass or less, and still more preferably substantially 100% by weight with respect to 100% by mass of total acid generator (B).

In the resist composition of the present invention, the proportion of the acid generator (B) is preferably 1 parts by mass or more and more preferably 3 parts by mass or more, and preferably 30 parts by mass or less and more preferably 25 parts by mass or less with respect to 100 parts by mass of the resin (A).

In the resist composition of the present invention, the acid generator (B) may be used as a single salt or as a combination of two or more of salts.

<Solvent (E)>

The proportion of a solvent (E) is generally 90% by mass or more, preferably 92% by mass or more, and more preferably 94% by mass or more, and also preferably 99% by mass or less, and more preferably 99.9% by mass or less. The proportion of the solvent (E) can be measured with a known analytical method such as liquid chromatography and gas chromatography.

Examples of the solvent (E) include glycol ether esters such as ethylcellosolve acetate, methylcellosolve acetate and propylene glycol monomethyl ether acetate; glycol ethers such as propylene glycol monomethyl ether; esters such as ethyl lactate, butyl acetate, amyl acetate and ethyl pyruvate; ketones such as acetone, methyl isobutyl ketone, 2-heptanone and cyclohexanone; and cyclic esters such as γ-butyrolactone. These solvents may be used as a single solvent or as a mixture of two or more solvents.

<Quencher (C)>

The resist composition of the present invention may contain a quencher such as a basic nitrogen-containing organic compound and a salt which generates an acid weaker in acidity than an acid generated from the acid generator.

The proportion of the quencher is preferably 0.01% by mass to 5% by mass with respect to the total solid components of the resist composition.

Examples of the basic nitrogen-containing organic compound include an amine and ammonium salts. The amine may be an aliphatic amine or an aromatic amine. The aliphatic amine includes any of a primary amine, secondary amine and tertiary amine.

Specific examples of the amine include 1-naphtylamine, 2-naphtylamine, aniline, diisopropylaniline, 2-, 3- or 4-methylaniline, 4-nitroaniline, N-methylaniline, N,N-dimethylaniline, diphenylamine, hexylamine, heptylamine, octylamine, nonylamine, decylamine, dibutylamine, dipentylamine, dihexylamine, diheptylamine, dioctylamine, dinonylamine, didecylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethyldiheptylamine, ethyldioctylamine, ethyldinonylamine, ethyldidecylamine, dicyclohexylmethylamine, tris[2-(2-methoxyethoxy)ethyl]amine, triisopropanolamine, ethylene diamine, tetramethylene diamine, hexamethylene diamine, 4,4'-diamino-1,2-diphenylethane, 4,4'-diamino-3,3'-dimethyldiphenylmethane, 4,4'-diamino-3,3'-diethyldiphenylmethane, 2,2'-methylenebisaniline, imidazole, 4-methylimidazole, pyridine, 4-methylpyridine, 1,2-di(2-pyridyl)ethane, 1,2-di(4-pyridyl)ethane, 1,2-di(2-pyridyl)ethene, 1,2-di(4-pyridyl)ethene, 1,3-di(4-pyridyl)propane, 1,2-di(4-pyridyloxy)ethane, di(2-pyridyl)ketone, 4,4'-dipyridyl sulfide, 4,4'-dipyridyl disulfide, 2,2'-dipyridylamine, 2,2'-dipicolylamine and bipyridine. Among these, diisopropylaniline is preferred, particularly 2,6-diisopropylaniline is more preferred.

Specific examples of the ammonium salt include tetramethylammonium hydroxide, tetraisopropylammonium hydroxide, tetrabutylammonium hydroxide, tetrahexylammonium hydroxide, tetraoctylammonium hydroxide, phenyltrimethyl ammonium hydroxide, 3-(trifluoromethyl)phenyltrimethylammonium hydroxide, tetra-n-butyl ammonium salicylate and choline.

<Weak Acid Salt>

The salt generating an acid which is lower in acidity than an acid generated from the acid generator (B) is sometimes referred to as "weak acid salt". The "acidity" can be represented by acid dissociation constant, pKa, of an acid generated from a weak acid salt. Examples of the weak acid salt include a salt generating an acid of pKa represents generally more than −3, preferably −1 to 7, and more preferably 0 to 5.

Specific examples of the weak acid salt include the following salts, the salt of formula (D), and salts as disclosed in JP2012-229206A1, JP2012-6908A1, JP2012-72109A1, JP2011-39502A1 and JP2011-191745A1, preferably the salt of formula (D).

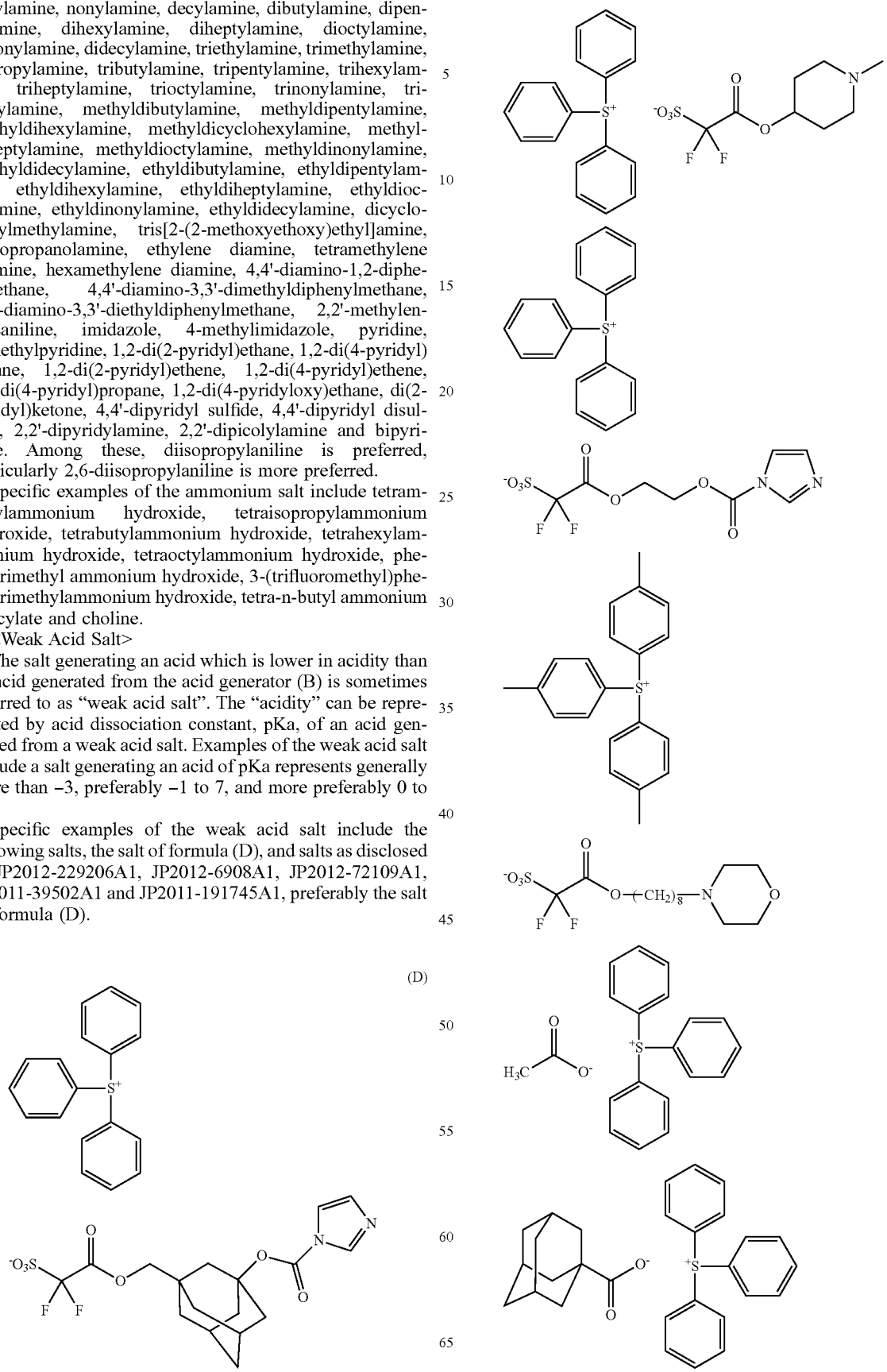

-continued

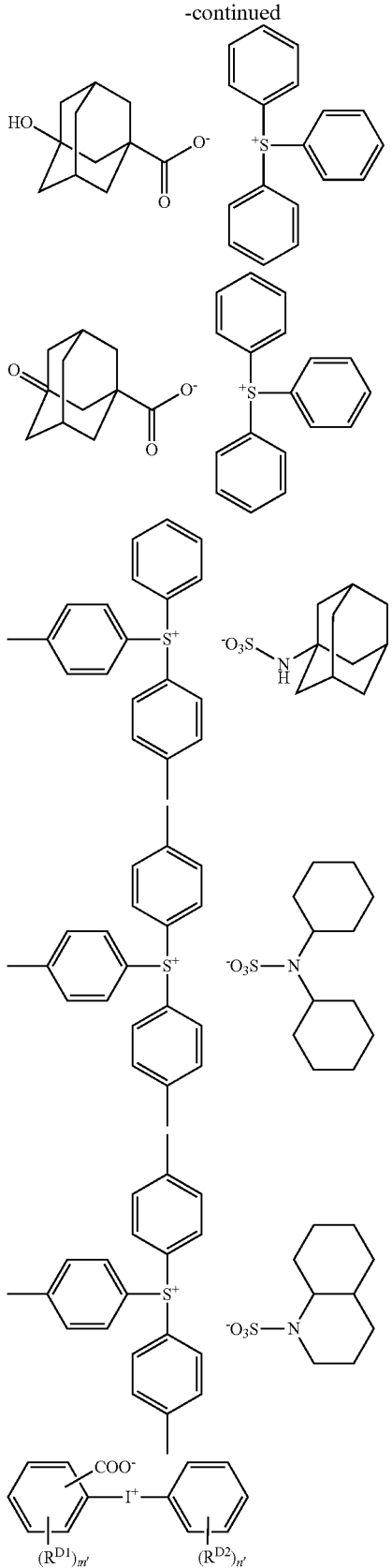

In the formula (D), $R^{D1}$ and $R^{D2}$ in each occurrence independently represent a $C_1$ to $C_{12}$ hydrocarbon group, a $C_1$ to $C_6$ alkoxyl group, a $C_2$ to $C_7$ acyl group, a $C_2$ to $C_7$ acyloxy group, a $C_2$ to $C_7$ alkoxycarbonyl group, a nitro group or a halogen atom;

m' and n' each independently represent an integer of 0 to 4.

Examples of the hydrocarbon group of $R^{D1}$ and $R^{D2}$ include any of an aliphatic hydrocarbon group, an alicyclic hydrocarbon group, an aromatic hydrocarbon group and a combination thereof.

Examples of the aliphatic hydrocarbon group include an alkyl group such as methyl, ethyl, propyl, isopropyl, butyl, sec-butyl, tert-butyl, pentyl, hexyl and nonyl groups.

The alicyclic hydrocarbon group is any one of monocyclic or polycyclic hydrocarbon group, and saturated or unsaturated hydrocarbon group. Examples thereof include a cycloalkyl group such as cyclopropyl, cyclobutyl, cyclopentyl, cyclohexyl, cyclononyl and cyclododecyl groups; adamantyl and norbornyl groups. The alicyclic hydrocarbon group is preferably saturated hydrocarbon group.

Examples of the aromatic hydrocarbon group include an aryl group such as phenyl, 1-naphthyl, 2-naphthyl, 2-methylphenyl, 3-methylphenyl, 4-methylphenyl, 4-ethylphenyl, 4-propylphenyl, 4-isopropylphenyl, 4-butylphenyl, 4-tert-butylphenyl, 4-hexylphenyl, 4-cyclohexylphenyl, anthryl, p-adamantylphenyl, tolyl, xylyl, cumenyl, mesityl, biphenyl, phenanthryl, 2,6-diethylphenyl and 2-methyl-6-ethylphenyl groups.

Examples of the combination thereof include an alkyl-cycloalkyl, a cycloalkyl-alkyl, aralkyl (e.g., phenylmethyl, 1-phenylethyl, 2-phenylethyl, 1-phenyl-1-propyl, 1-phenyl-2-propyl, 2-phenyl-2-propyl, 3-phenyl-1-propyl, 4-phenyl-1-butyl, 5-phenyl-1-pentyl and 6-phenyl-1-hexyl groups) groups.

Examples of the alkoxyl group include methoxy and ethoxy groups.

Examples of the acyl group include acetyl, propanonyl, benzoyl and cyclohexanecarbonyl groups.

Examples of the acyloxy group include a group in which oxy group (—O—) bonds to an acyl group.

Examples of the alkoxycarbonyl group include a group in which the carbonyl group (—CO—) bonds to the alkoxy group.

Example of the halogen atom is a chlorine atom, a fluorine atom and bromine atom.

In the formula (D), $R^{D1}$ and $R^{D2}$ in each occurrence independently preferably represent a $C_1$ to $C_8$ alkyl group, a $C_3$ to $C_{10}$ cycloalkyl group, a $C_1$ to $C_6$ alkoxyl group, a $C_2$ to $C_4$ acyl group, a $C_2$ to $C_4$ acyloxy group, a $C_2$ to $C_4$ alkoxycarbonyl group, a nitro group or a halogen atom.

m' and n' independently preferably represent an integer of 0 to 3, more preferably an integer of 0 to 2, and more preferably 0.

Specific examples of the salt of the formula (D) include compounds below.

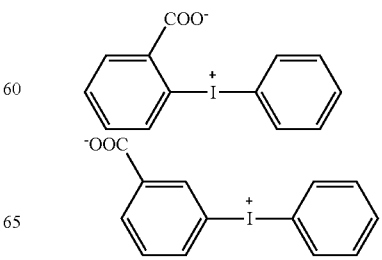

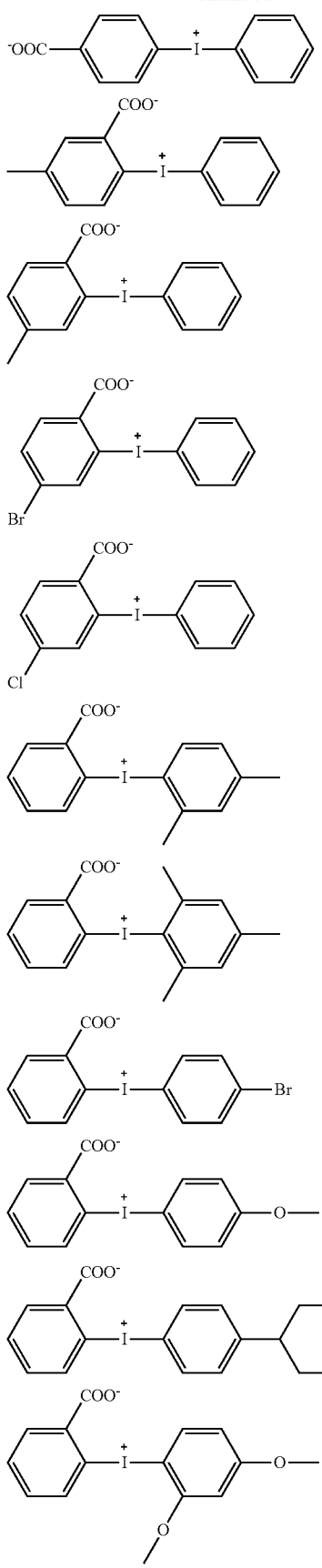
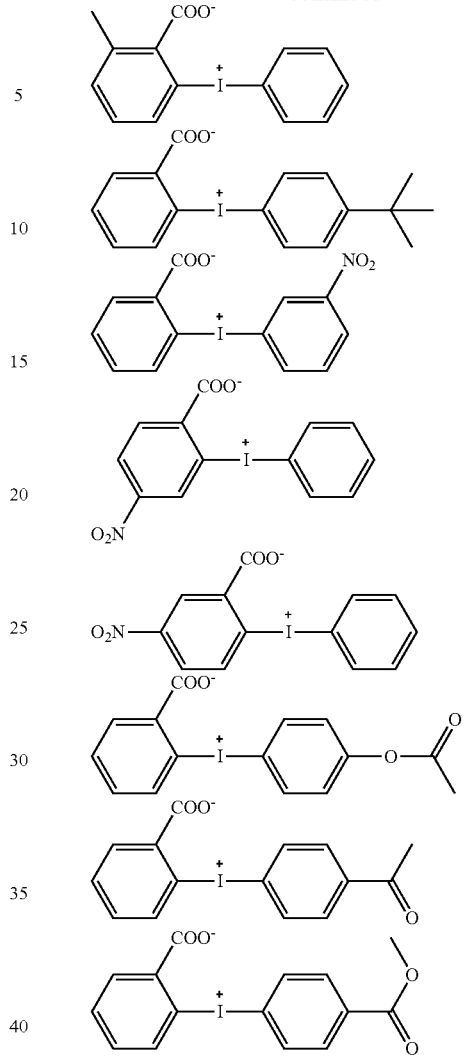

The salt of the formula (D) can be produced by a method described in "Tetrahedron Vol. 45, No. 19, p6281-6296". Also, commercially available compounds can be used as the salt of the formula (D).

In the resist composition of the present invention, the proportion of the salt which generates an acid weaker in acidity than an acid generated from the acid generator, for example, the salt of the formula (D) is preferably 0.01% by mass to 5% by mass, more preferably 0.01% by mass to 4% by mass, and still more preferably 0.01% by mass to 3% by mass with respect to total solid components of the resist composition.

<Other ingredient>

The resist composition can also include other ingredient (which is sometimes referred to as "other ingredient (F)"). Examples of the other ingredient (F) include various additives such as sensitizers, dissolution inhibitors, surfactants, stabilizers, and dyes, as needed.

<Preparing the Resist Composition>

The present resist composition can be prepared by mixing the resin (A), the compound (a), the acid generator (B), the resin other than the resin (A), the quencher, the solvent (E) and the other ingredient (F), as needed. There is no particular limitation on the order of mixing. The mixing may be performed in an arbitrary order. The temperature of mixing may be adjusted to an appropriate temperature within the range of 10 to 40° C., depending on the kinds of the resin and solubility in the solvent (E) of the resin. The time of mixing may be adjusted to an appropriate time within the range of 0.5 to 24 hours, depending on the mixing temperature. There is no particular limitation to the tool for mixing. An agitation mixing may be adopted.

After mixing the above ingredients, the present resist compositions can be prepared by filtering the mixture through a filter having about 0.003 to 0.2 µm pore diameter.

<Method for Producing Resist Pattern>

The method for producing a resist pattern of the present invention includes the steps of:
 (1) applying the resist composition of the present invention onto a substrate;
 (2) drying the applied composition to form a composition layer;
 (3) exposing the composition layer;
 (4) heating the exposed composition layer, and
 (5) developing the heated composition layer.

Applying the resist composition onto the substrate can generally be carried out through the use of a resist application device, such as a spin coater known in the field of semiconductor microfabrication technique. Examples of the substrate include inorganic substrates such as silicon wafer. The substrate may be washed, and an organic antireflection film may be formed on the substrate by use of a commercially available antireflection composition, before the application of the resist composition.

The solvent evaporates from the resist composition and a composition layer with the solvent removed is formed. Drying the applied composition layer, for example, can be carried out using a heating device such as a hotplate (so-called "prebake"), a decompression device, or a combination thereof. The temperature is preferably within the range of 50 to 200° C. The time for heating is preferably 10 to 180 seconds. The pressure is preferably within the range of 1 to $1.0 \times 10^5$ Pa.

The composition layer thus obtained is generally exposed using an exposure apparatus or a liquid immersion exposure apparatus. The exposure is generally carried out using with various types of exposure light source, such as irradiation with ultraviolet lasers, i.e., KrF excimer laser (wavelength: 248 nm), ArF excimer laser (wavelength: 193 nm), $F_2$ excimer laser (wavelength: 157 nm), irradiation with harmonic laser light of far-ultraviolet or vacuum ultra violet wavelength-converted laser light from a solid-state laser source (YAG or semiconductor laser or the like), or irradiation with electron beam or EUV or the like. In the specification, such exposure to radiation is sometimes referred to be collectively called as exposure. The exposure is generally carried out through a mask that corresponds to the desired pattern. When electron beam is used as the exposure light source, direct writing without using a mask can be carried out.

After exposure, the composition layer is subjected to a heat treatment (so-called "post-exposure bake") to promote the deprotection reaction. The heat treatment can be carried out using a heating device such as a hotplate. The heating temperature is generally in the range of 50 to 200 degree C., preferably in the range of 70 to 150 degree C.

The developing of the baked composition film is usually carried out with a developer using a development apparatus. Developing can be conducted in the manner of dipping method, paddle method, spray method and dynamic dispensing method. Temperature for developing is generally 5 to 60 degree C. The time for developing is preferably 5 to 300 seconds.

The photoresist pattern obtained from the photoresist composition may be a positive one or a negative one by selecting suitable developer.

The development for obtaining a positive photoresist pattern is usually carried out with an alkaline developer. The alkaline developer to be used may be any one of various alkaline aqueous solution used in the art. Generally, an aqueous solution of tetramethylammonium hydroxide or (2-hydroxyethyl)trimethylammonium hydroxide (commonly known as "choline") is often used. The surfactant may be contained in the alkaline developer.

After development, the resist pattern formed is preferably washed with ultrapure water, and the residual water remained on the resist film or on the substrate is preferably removed therefrom.

The development for obtaining a negative photoresist pattern is usually carried out with a developer containing an organic solvent. The organic solvent to be used may be any one of various organic solvents used in the art, examples of which include ketone solvents such as 2-hexanone, 2-heptanone; glycol ether ester solvents such as propylene glycol monomethyl ether acetate; ester solvents such as the butyl acetate; glycol ether solvents such as the propylene glycol monomethyl ether; amide solvents such as N,N-dimethylacetamide; aromatic hydrocarbon solvents such as anisole.

In the developer containing an organic solvent, the amount of organic solvents is preferably 90% by mass to 100% by mass, more preferably 95% by mass to 100% by mass of the developer. The developer still more preferably consists essentially of organic solvents.

Among these, the developer containing an organic solvent preferably contains butyl acetate and/or 2-heptanone. In the developer containing an organic solvent, the total amount of butyl acetate and 2-heptanone is preferably 50% by mass to 100% by mass of the developer, more preferably 90% by mass to 100% by mass of the developer. The developer still more preferably consists essentially of butyl acetate and/or 2-heptanone.

Developers containing an organic solvent may contain a surfactant. Also, the developer containing an organic solvent may include a little water.

The developing with a developer containing an organic solvent can be finished by replacing the developer by another solvent.

After development, the photoresist pattern formed is preferably washed with a rinse agent. Such rinse agent is not unlimited provided that it does not detract a photoresist pattern. Examples of the agent include solvents which contain organic solvents other than the above-mentioned developers, such as alcohol agents or ester agents.

After washing, the residual rinse agent remained on the substrate or photoresist film is preferably removed therefrom.

<Application>

The resist composition of the present invention is useful for excimer laser lithography such as with ArF, KrF, electron beam (EB) exposure lithography or extreme-ultraviolet (EUV) exposure lithography, and is more useful for electron beam (EB) exposure lithography, ArF excimer laser exposure lithography and extreme-ultraviolet (EUV) exposure lithography.

The resist composition of the present invention can be used in semiconductor microfabrication.

EXAMPLES

The present invention will be described more specifically by way of examples, which are not construed to limit the scope of the present invention.

All percentages and parts expressing the content or amounts used in the Examples and Comparative Examples are based on mass, unless otherwise specified.

The weight average molecular weight is a value determined by gel permeation chromatography.
  Device: HLC-8120GPC model (Tosoh Co. Ltd.)
  Column: TSK gel Multipore HXL-M x 3+guardcolumn (Tosoh Co. Ltd.)
  Eluant: tetrahydrofuran
  Flow rate: 1.0 mL/min.
  Detecting device: RI detector
  Column temperature: 40° C.
  Injection amount: 100 µL
  Standard material for calculating molecular weight: standard polystyrene (Tosoh Co. ltd.)

Structures of compounds were determined by mass spectrometry (Liquid Chromatography: 1100 Type, manufactured by AGILENT TECHNOLOGIES LTD., Mass Spectrometry: LC/MSD Type, manufactured by AGILENT TECHNOLOGIES LTD.). The value of the peak in the mass spectrometry is referred to as "MASS".

Example 1

Synthesis of the Compound Represented by the Formula (I-1)

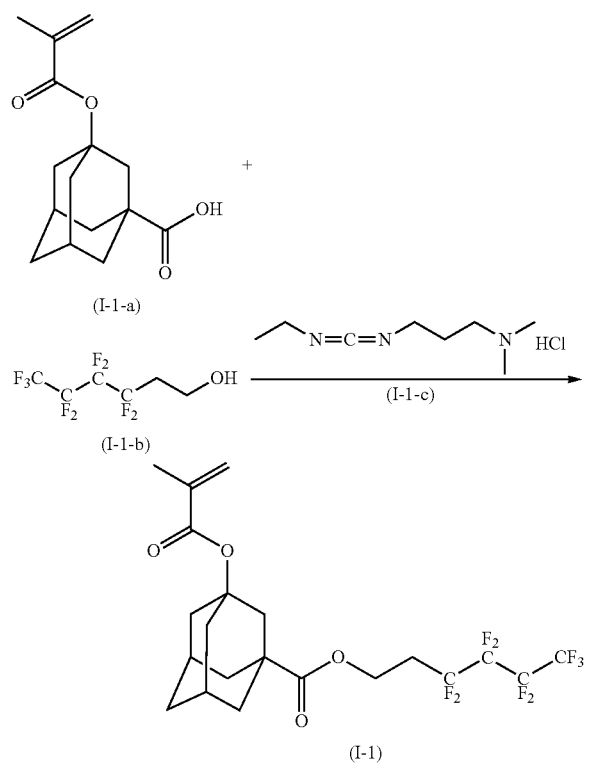

Into a reactor, 21.2 parts of the compound represented by the formula (I-1-a), 106 parts of chloroform, 6.98 parts of pyridine, 1.96 parts of dimethylaminopyridine, 20.12 parts of the compound represented by the formula (I-1-b) and 16.91 parts of the compound represented by the formula (I-1-c) were charged and stirred at 23 degree C. for 5 hours. Then, 350 parts of chloroform was added to the resulting solution, and then 65 parts of 5% hydrochloric acid was added, and the mixture was stirred at 23 degree C. for 30 minutes. Then, the mixture was left still to separate an organic layer. To the obtained organic layer, 170 parts of ion exchanged water was added, and the obtained mixture was stirred at 23 degree C. for 30 minutes, followed by separating an organic layer to wash with water. The washing step with water was conducted six times. The washed organic layer was concentrated and purified with column chromatography [silica gel 60N spherical shape, neutral, 100-210 µm, solvent: mixture of n-heptane and ethyl acetate (weight ratio 10/1), manufactured by Kanto Chem. Ltd.] to obtain 28.64 parts of the compound represented by formula (I-1).

MS (mass spectrography): 510.2 (molecular ion peak)

Example 2

Synthesis of the Compound Represented by the Formula (I-12)

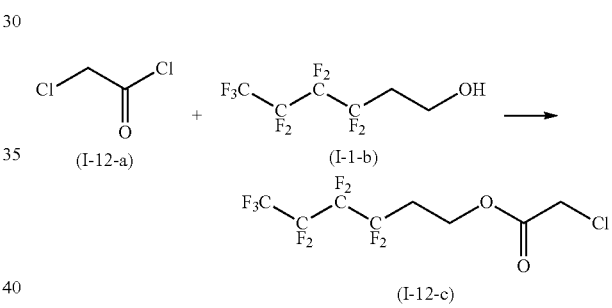

Into a reactor, 24 parts of the compound represented by the formula (I-1-b), 120 parts of tetrahydrofuran, 7.90 parts of pyridine and 11.28 parts of the compound represented by the formula (I-12-a) were charged and stirred at 23 degree C. for 3 hours. Then, 240 parts of n-heptane was added to the resulting solution, and then 73 parts of 5% hydrochloric acid was added, and the mixture was stirred at 23 degree C. for 30 minutes. Then, the mixture was left still to separate an organic layer. To the obtained organic layer, 120 parts of ion exchanged water was added, and the obtained mixture was stirred at 23 degree C. for 30 minutes, followed by separating an organic layer to wash with water. The washing step was conducted six times. The washed organic layer was concentrated to obtain 29.47 parts of the compound represented by formula (I-12-c).

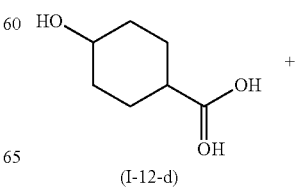

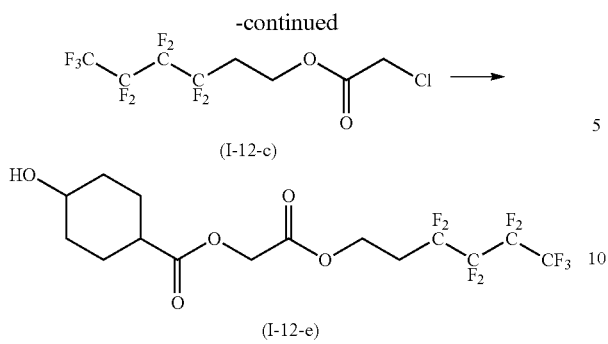

Into a reactor, 10 parts of the compound represented by the formula (I-12-d), 50 parts of dimethylformamide, 4.79 parts of potassium carbonate and 1.15 parts of potassium iodide were charged and stirred, and then 28.35 parts of the compound represented by the formula (I-12-c) was added thereto and the obtained mixture was stirred at 23 degree C. for 5 hours. Then, 200 parts of chloroform was added to the resulting solution, and then 25 parts of 5% hydrochloric acid was added, and the mixture was stirred 23 degree C. for 30 minutes. Then, the mixture was left still to separate an organic layer. 100 parts of ion exchanged water was added to the obtained organic layer and the obtained mixture was stirred at 23 degree C. for 30 minutes, followed by separating an organic layer to wash with water. The washing step was conducted six times. The washed organic layer was concentrated to obtain 28.24 parts of the compound represented by formula (I-12-e).

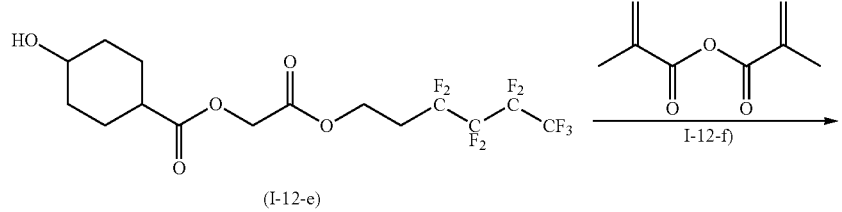

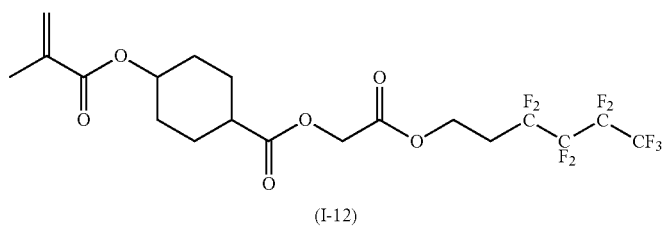

Into a reactor, 28.23 parts of the compound represented by the formula (I-12-e), 145 parts of tetrahydrofuran, 7.54 parts of pyridine and 0.97 parts of dimethylaminopyridine were charged, and then 13.47 parts of the compound represented by the formula (I-12-f) was added thereto and stirred at 23 degree C. for 18 hours. Then, 290 parts of n-heptane was added to the resulting solution, and then 70 parts of 5% hydrochloric acid was added, and the mixture was stirred 23 degree C. for 30 minutes. Then, the mixture was left still to separate an organic layer. 145 parts of ion exchanged water was added to the obtained organic layer and the obtained mixture was stirred at 23 degree C. for 30 minutes, followed by separating an organic layer to wash with water. The washing step was conducted six times. The washed organic layer was concentrated and purified with column chromatography [silica gel 60N spherical shape, neutral, 100-210 μm, solvent: mixture of n-heptane and ethyl acetate (weight ratio 10/1), manufactured by Kanto Chem. Ltd.] to obtain 28.73 parts of the compound represented by formula (I-12).

MS (mass spectrography): 516.1 (molecular ion peak)

Example 3

Synthesis of a Compound Represented by the Formula (I-15)

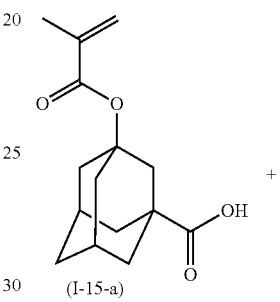

-continued

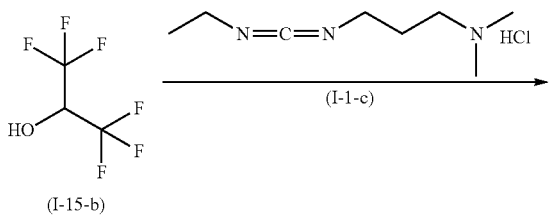

133

-continued

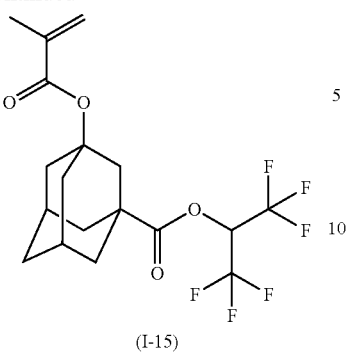

(I-15)

Into a reactor, 21.2 parts of the compound represented by the formula (I-15-a), 106 parts of chloroform, 6.98 parts of pyridine, 1.96 parts of dimethylaminopyridine, 12.80 parts of the compound represented by the formula (I-15-b) and 16.91 parts of the compound represented by the formula (I-1-c) were charged and stirred at 23 degree C. for 5 hours. Then, 350 parts of chloroform was added to the resulting solution, and then 65 parts of 5% hydrochloric acid was added, and the mixture was stirred 23 degree C. for 30 minutes. Then, the mixture was left still to separate an organic layer. 170 parts of ion exchanged water was added to the obtained organic layer and the obtained mixture was stirred at 23 degree C. for 30 minutes, followed by separating an organic layer to wash with water. The washing step was conducted six times. The washed organic layer was concentrated and purified with column chromatography [silica gel 60N spherical shape, neutral, 100-210 μm, solvent: mixture of n-heptane and ethyl acetate (weight ratio 10/1), manufactured by Kanto Chem. Ltd.] to obtain 22.12 parts of the compound represented by formula (I-15).

MS (mass spectrography): 414.1 (molecular ion peak)

Example 4

Synthesis of a Compound Represented by the formula (I-3)

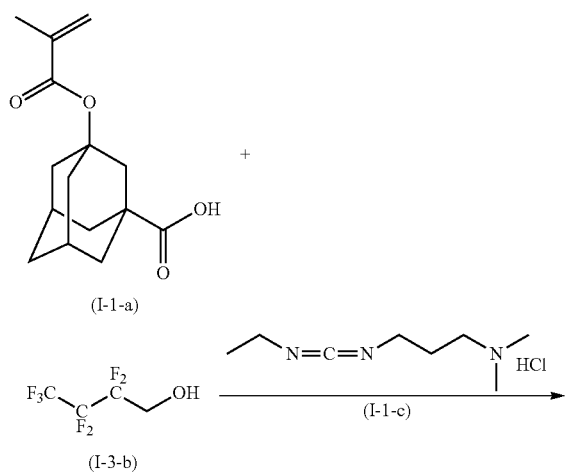

134

-continued

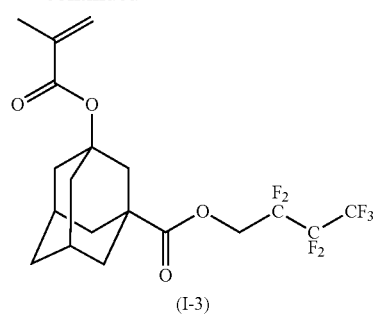

(I-3)

Into a reactor, 21.2 parts of the compound represented by the formula (I-1-a), 100 parts of chloroform, 6.98 parts of pyridine, 1.96 parts of dimethylaminopyridine, 15.24 parts of the compound represented by the formula (I-3-b) and 16.91 parts of the compound represented by the formula (I-1-c) were charged and stirred at 23 degree C. for 5 hours. Then, 350 parts of chloroform was added to the resulting solution, and then 65 parts of 5% hydrochloric acid was added, and the mixture was stirred 23 degree C. for 30 minutes. Then, the mixture was left still to separate an organic layer. 170 parts of ion exchanged water was added to the obtained organic layer and the obtained mixture was stirred at 23 degree C. for 30 minutes, followed by separating an organic layer to wash with water. The washing step was conducted five times. The washed organic layer was concentrated and purified with column chromatography [silica gel 60N spherical shape, neutral, 100-210 μm, solvent: mixture of n-heptane and ethyl acetate (weight ratio 10/1), manufactured by Kanto Chem. Ltd.] to obtain 24.22 parts of the compound represented by formula (I-3).

MS (mass spectrography): 446.1 (molecular ion peak)

Example 5

Synthesis of a Compound Represented by the Formula (I-10)

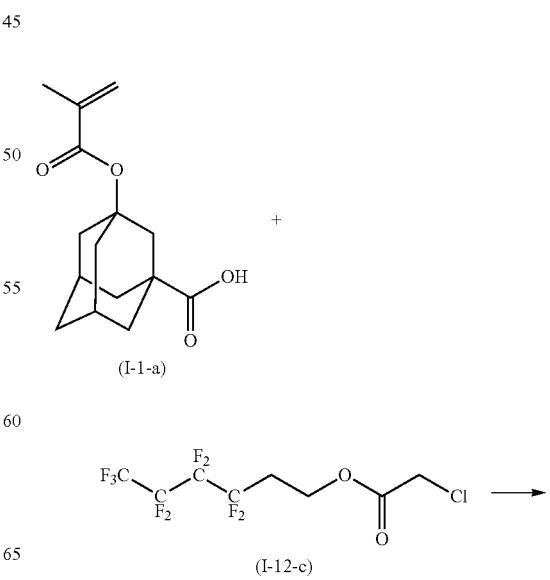

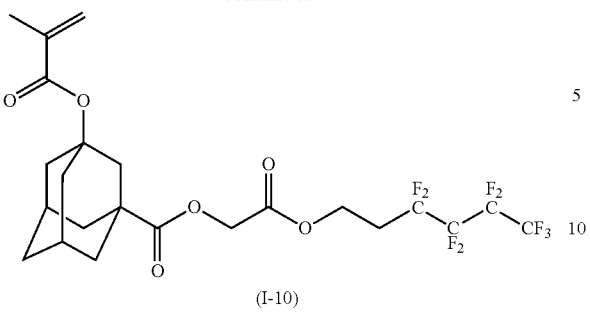

(I-10)

Into a reactor, 18.33 parts of the compound represented by the formula (I-1-a)), 50 parts of dimethylformamide, 4.79 parts of potassium carbonate and 1.15 parts of potassium iodide were charged and stirred, and then 28.35 parts of the compound represented by the formula (I-12-c) was added and stirred at 23 degree C. for 5 hours. Then, 200 parts of chloroform was added to the resulting solution, and then 25 parts of 5% hydrochloric acid was added, and the mixture was stirred 23 degree C. for 30 minutes. Then, the mixture was left still to separate an organic layer. 100 parts of ion exchanged water was added to the obtained organic layer and the obtained mixture was stirred at 23 degree C. for 30 minutes, followed by separating an organic layer to wash with water. The washing step was conducted five times. The washed organic layer was concentrated to obtain 23.24 parts of the compound represented by formula (I-10).

MS (mass spectrography): 568.2 (molecular ion peak)

Synthesis Example 1

Synthesis of a Salt Represented by the Formula (B1-5)

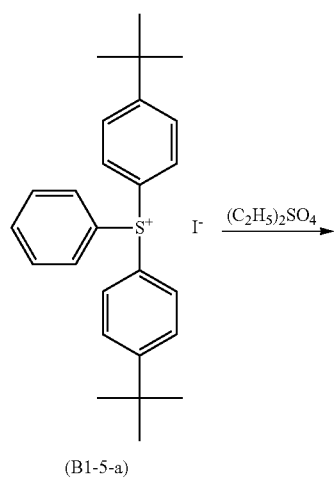

(B1-5-a)

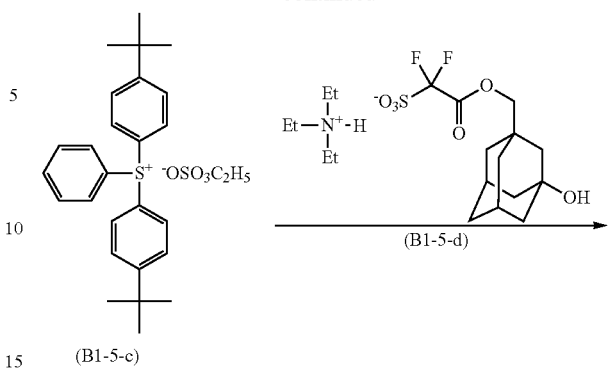

(B1-5-c)

(B1-5)

In to a reactor, 50.49 parts of compound represented by formula (B1-5-a) and 252.44 parts of chloroform were mixed and stirred at 23 degree C. for 30 minutes. Then 16.27 parts of compound represented by formula (B1-5-b) were dropped thereinto and the obtained mixture was stirred at 23 degree C. for one hour to obtain a solution containing the compound represented by formula (B1-5-c).

To the obtained solution, 48.80 parts of compound represented by formula (B1-5-d) and 84.15 parts of ion-exchanged water were added and the obtained mixture was stirred at 23 degree C. for 12 hours. From the obtained solution which had two layers, the chloroform layer was collected and then 84.15 parts of ion-exchanged water were added for washing. The washing step was conducted five times. To the washed chloroform layer, 3.88 parts of active carbon were added and the obtained mixture was stirred, followed by filtrating. The collected filtrate was concentrated and then 125.87 parts of acetonitrile were added thereto and the obtained mixture was stirred, followed by being concentrated. 20.62 parts of acetonitrile and 309.30 parts of tert-butylmethylether were added to the obtained residues, followed by being stirred at 23 degree C. for about 30 minutes. Then the supernatant was removed therefrom, and the residues were concentrated. To the concentrated residues, 200 parts of n-heptane were added and the obtained mixture was stirred at 23 degree C. for about 30 minutes, followed by being filtrated to obtain 61.54 parts of salt represented by formula (B1-5).

MASS(ESI(+)Spectrum):$M^+$375.2

MASS(ESI(−)Spectrum):$M^-$339.1

Synthesis Example 2

Synthesis of a Salt Represented by the Formula (B1-21)

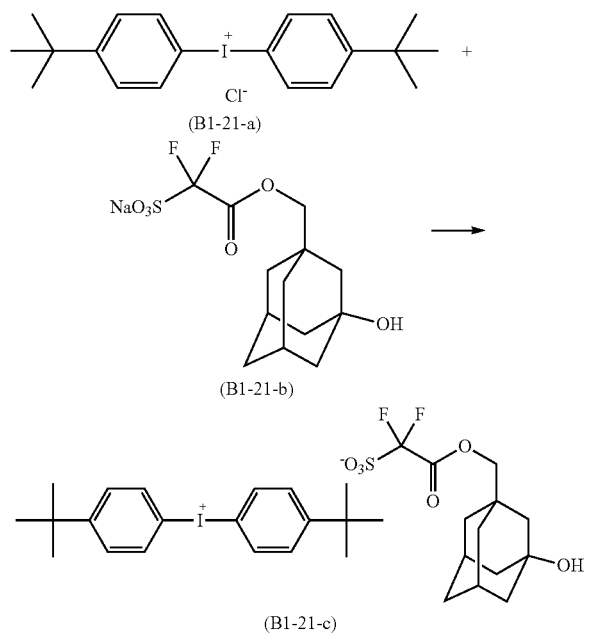

The compound represented by formula (B1-21-b) was produced according to a method recited in JP2008-209917A1.

30.00 parts of compound represented by formula (B1-21-b) and 35.50 parts of salt represented by formula (B1-21-a), 100 parts of chloroform and 50 parts of ion exchanged water were mixed and stirred at 23 degree C. for about 15 hours. The obtained reaction mixture, which had two layers, was separated into a chloroform layer therefrom. To the chloroform layer, 30 parts of ion exchanged water was added and washed with it. These steps were conducted five times. Then the washed layer was concentrated, and then, 100 parts of tert-butylmethylether was added to the obtained residues and the obtained mixture was stirred at 23 degree C. for about 30 minutes. The resulting mixture was filtrated to obtain 48.57 parts of salt represented by formula (B1-21-c).

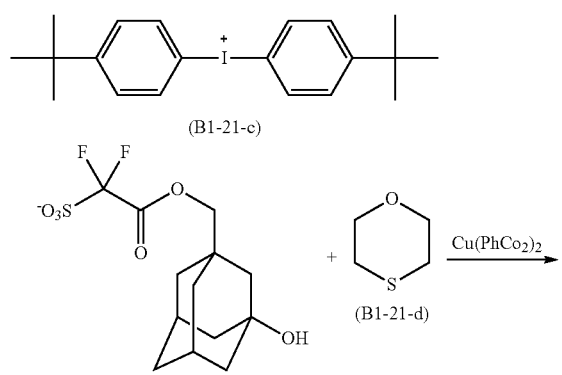

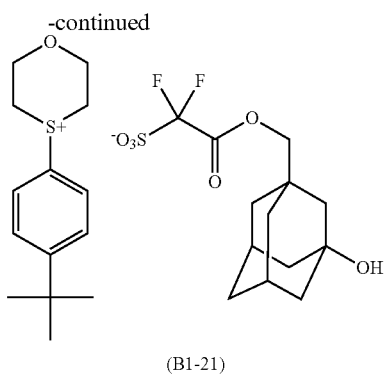

20.00 parts of salt represented by formula (B1-21-c), 2.84 parts of compound represented by formula (B1-21-d) and 250 parts of monochlorobenzene were mixed and stirred at 23 degree C. for 30 minutes. To the resulting mixture, 0.21 parts of copper (II) dibenzoate was added and the obtained mixture was stirred at 100 degree C. for 1 hour. The reaction mixture was concentrated, and then, 200 parts of chloroform and 50 parts of ion exchanged water were added to the obtained residues and the obtained mixture was stirred at 23 degree C. for 30 minutes, followed by being separated into an organic layer therefrom. The following washing step was conducted five times. 50 parts of ion exchanged water were added to the obtained organic layer, and the obtained mixture was stirred at 23 degree C. for 30 minutes, followed by being separated into an organic layer. The obtained organic layer was concentrated, and then the obtained residues were dissolved in 53.51 parts of acetonitrile. Then the mixture was concentrated, and then 113.05 parts of tert-butylmethylether was added thereto and the obtained mixture was stirred, followed by filtrating it to obtain 10.47 parts of salt represented by formula (B1-21).

MASS(ESI(+)Spectrum):$M^+$237.1
MASS(ESI(−)Spectrum):$M^-$339.1

Synthesis Example 3

Synthesis of a Salt Represented by the Formula (B1-22)

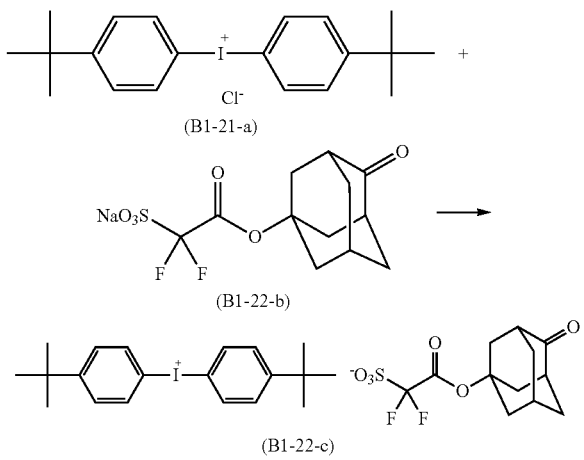

11.26 parts of salt represented by formula (B1-21-a), 10 parts of compound represented by formula (B1-22-b), 50 parts of chloroform and 25 parts of ion exchanged water were mixed and stirred at 23 degree C. for about 15 hours. The obtained reaction mixture, which had two layers, was separated into a chloroform layer therefrom. To the chloroform layer, 15 parts of ion exchanged water were added and washed with it: These steps were conducted five times. Then the washed layer was concentrated, and then, 50 parts of tert-butylmethylether was added to the obtained residues and the obtained mixture was stirred at 23 degree C. for about 30 minutes. The resulting mixture was filtrated to obtain 11.75 parts of salt represented by formula (B1-22-c).

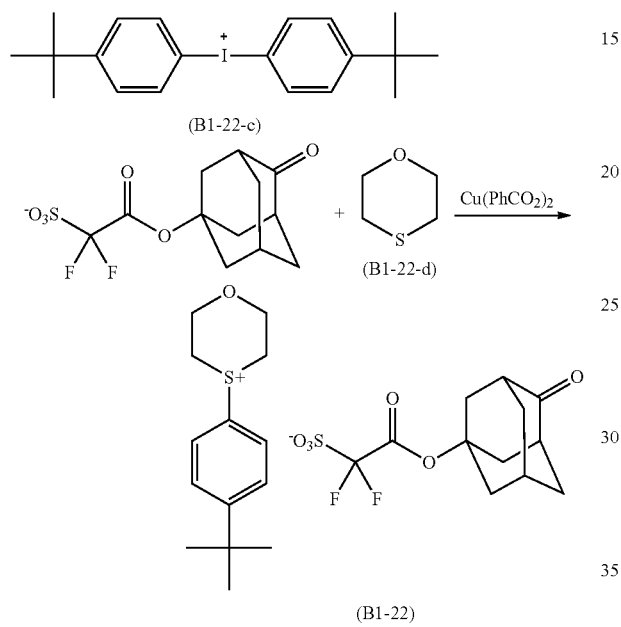

11.71 parts of salt represented by formula (B1-22-c), 1.7 parts of compound represented by formula (B1-22-d) and 46.84 parts of monochlorobenzene were mixed and stirred at 23 degree C. for 30 minutes. To the resulting mixture, 0.12 parts of copper (II) dibenzoate was added and the obtained mixture was stirred at 100 degree C. for 30 minutes. The reaction mixture was concentrated, and then, to the obtained residues, 50 parts of chloroform and 12.5 parts of ion exchanged water were added and the obtained mixture was stirred at 23 degree C. for 30 minutes, followed by being separated into an organic layer therefrom. 12.5 parts of ion exchanged water was added to the obtained organic layer and the obtained mixture was stirred at 23 degree C. for 30 minutes, followed by being separated into an organic layer therefrom. The washing step was conducted eight times. Then the mixture was concentrated, and then 50 parts of tert-butylmethylether were added thereto and the obtained mixture was stirred, followed by filtrating it to obtain 6.84 parts of salt represented by formula (B1-22).

MASS(ESI(+)Spectrum):M$^+$237.1
MASS(ESI(−)Spectrum):M$^-$323.0

Synthetic Example of the Resin

The monomers used for Synthesis of resins are shown below. These monomers are referred to as "monomer (X)" where "(X)" is the symbol of the formula representing the structure of each monomer.

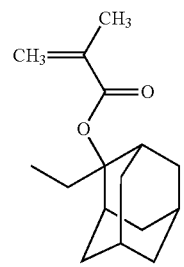
(a1-1-2)

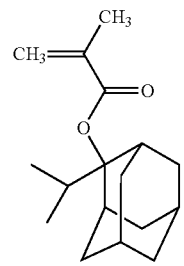
(a1-1-3)

(a1-2-3)

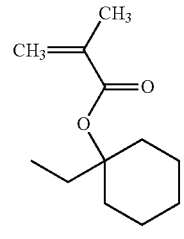
(a1-2-9)

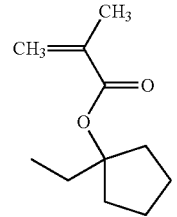
(a2-1-1)

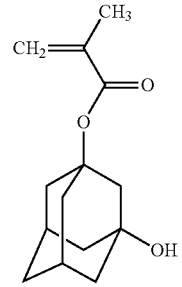
(a2-1-3)

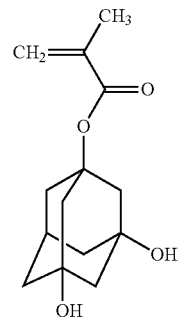

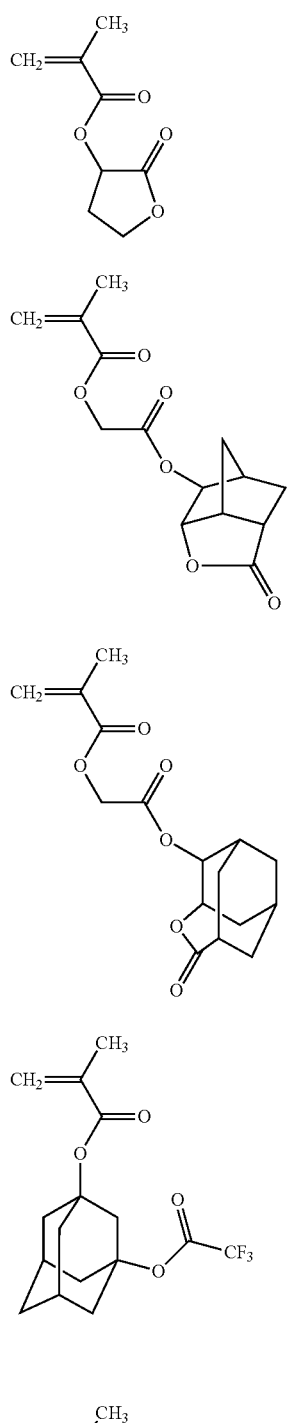
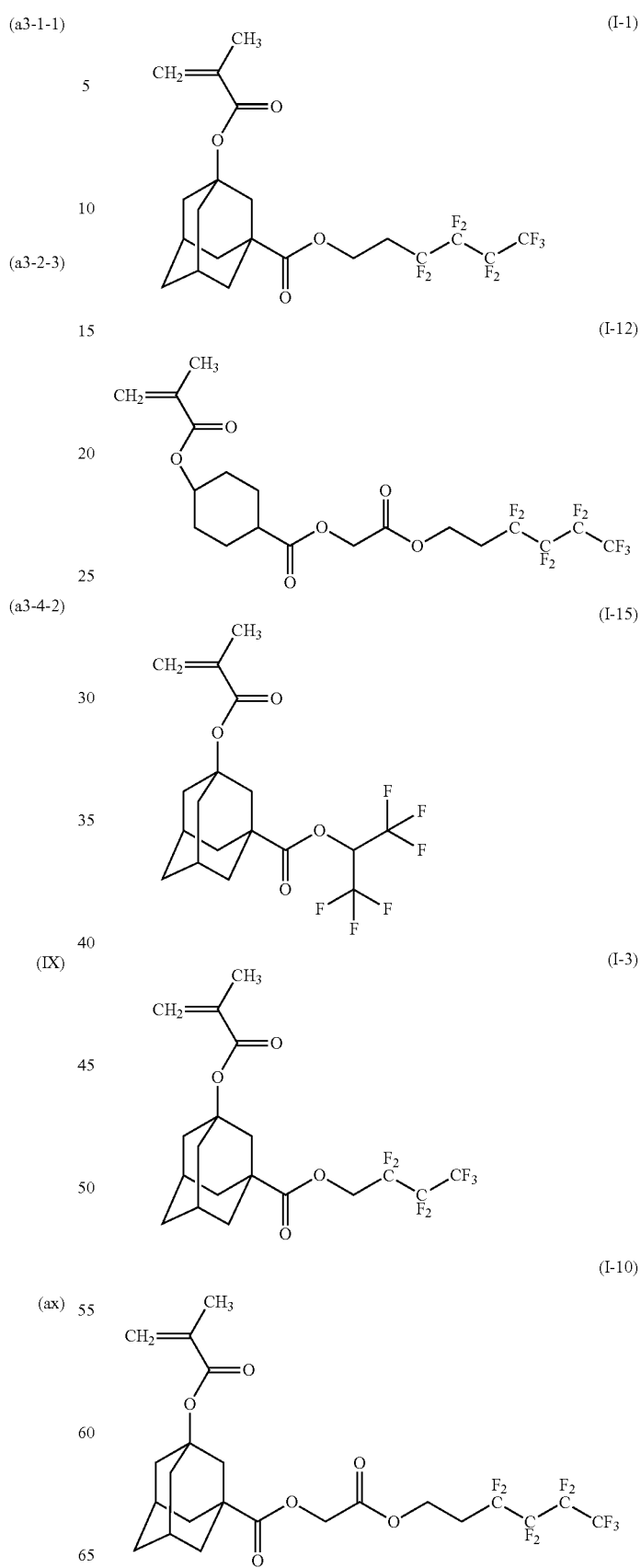

-continued (a5-1-1)
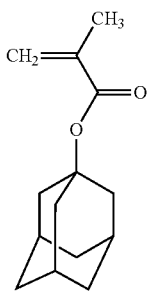

(a5-1-20)
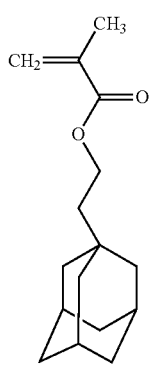

(a4-0-12)
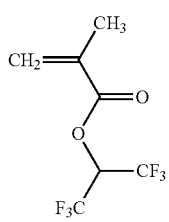

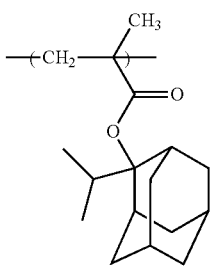
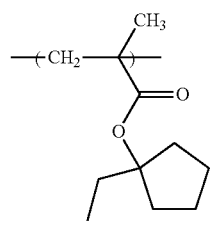

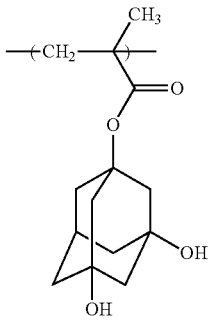
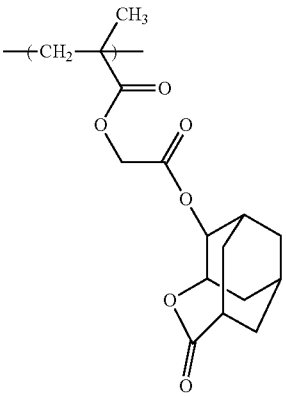

Synthesis Example 4

Synthesis of Resin A1

Monomer (a1-1-3), monomer (a1-2-9), monomer (a2-1-3) and monomer (a3-4-2) were mixed together with the mole ratio of monomer (a1-1-3), monomer (a1-2-9), monomer (a2-1-3) and monomer (a3-4-2)=45:14:2.5:38.5, and propyleneglycolmonomethylether acetate was added thereto in the amount equal to 1.5 times by mass of the total amount of monomers to obtain a solution. Azobisisobutyronitrile and azobis(2,4-dimethylvaleronitrile) were added as initiators to the solution in the amounts of 1% by mole and 3% by mole respectively with respect to the total amount of monomers, and the resultant mixture was heated for about 5 hours at 73° C. Then, the obtained reacted mixture was poured into a large amount of a mixture of methanol and water to precipitate a resin. The obtained resin was filtrated. Thus obtained resin was dissolved in another propylene glycol monomethylether acetate to obtain a solution, and the solution was poured into a large amount of a mixture of methanol and water to precipitate the resin. The obtained resin was filtrated. These operations were repeated two times to obtain the copolymer having a weight average molecular weight of about 7600 in 68% yield. This resin, which had the structural units of the following formulae, was referred to as Resin A1.

Synthesis Example 5

Synthesis of Resin A2

Monomer (a1-1-2), monomer (a1-2-3), monomer (a2-1-1), monomer (a3-2-3) and monomer (a3-1-1) were mixed together with the mole ratio of monomer (a1-1-2), monomer (a1-2-3), monomer (a2-1-1), monomer (a3-2-3) and monomer (a3-1-1)=32:7:8:10:43, and propylene glycol monomethylether acetate was added thereto in the amount equal to 1.5 times by mass of the total amount of monomers to obtain a solution. Azobisisobutyronitrile and azobis(2,4-dimethylvaleronitrile) were added as initiators to the solution in the amounts of 0.95% by mole and 2.85% by mole respectively with respect to the total amount of monomers, and the resultant mixture was heated for about 5 hours at 75° C. Then, the obtained reacted mixture was poured into a large amount of a mixture of methanol and ion exchanged water (4/1) to precipitate a resin. The obtained resin was filtrated to obtain the copolymer having a weight average molecular weight of about 8900 in 70% yield. This resin, which had the structural units of the following formula, was referred to Resin A2.

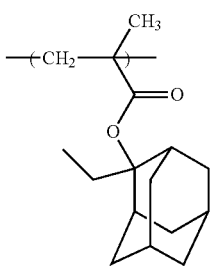
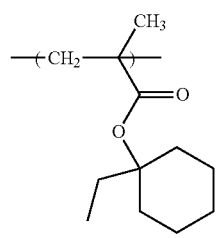

-continued

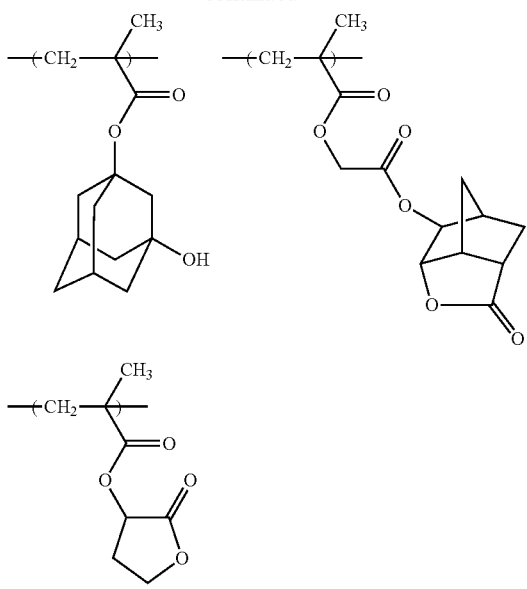

Example 6

Synthesis of Resin X1

Monomer (I-1) was used, and propyleneglycolmonomethylether acetate was added thereto in the amount equal to 1.5 times by mass of the total amount of monomers to obtain a solution. Azobisisobutyronitrile and azobis(2,4-dimethylvaleronitrile) were added as initiators to the solution in the amounts of 0.7% by mole and 2.1% by mole respectively with respect to the total amount of monomers, and the resultant mixture was heated for about 5 hours at 75° C. Then, the obtained reacted mixture was poured into a large amount of a mixture of methanol and water to precipitate a resin. The obtained resin was filtrated. Thus obtained resin was dissolved in another propylene glycol monomethyl ether acetate to obtain a solution, and the solution was poured into a mixture of methanol and water to precipitate the resin. The obtained resin was filtrated. These operations were repeated twice to obtain the copolymer having a weight average molecular weight of about 14000 in 75% yield. This resin, which had the structural units of the following formula, was referred to as Resin X1.

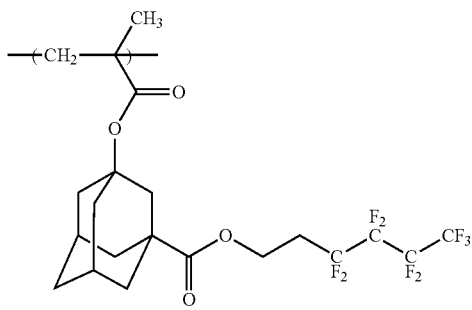

Example 7

Synthesis of Resin X2

Monomer (I-12) was used, and propylene glycol monomethyl ether acetate was added thereto in the amount equal to 1.5 times by mass of the total amount of monomers to obtain a solution. Azobisisobutyronitrile and azobis(2,4-dimethylvaleronitrile) were added as initiators to the solution in the amounts of 0.7% by mole and 2.1% by mole respectively with respect to the total amount of monomers, and the resultant mixture was heated for about 5 hours at 75° C. Then, the obtained reacted mixture was poured into a large amount of a mixture of methanol and water to precipitate a resin. The obtained resin was filtrated. Thus obtained resin was dissolved in another propylene glycol monomethyl ether acetate to obtain a solution, and the solution was poured into a mixture of methanol and water to precipitate the resin. The obtained resin was filtrated. These operations were repeated twice to obtain the copolymer having a weight average molecular weight of about 14000 in 70% yield. This resin, which had the structural units of the following formula, was referred to Resin X2.

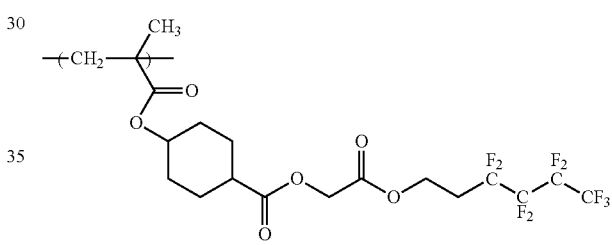

Example 8

Synthesis of Resin X3

Monomer (I-1) and monomer (ax) were mixed together with the mole ratio of monomer (I-1) and monomer (ax)= 45:55, and propylene glycol monomethylether acetate was added thereto in the amount equal to 1.5 times by mass of the total amount of monomers to obtain a solution. Azobisisobutyronitrile and azobis(2,4-dimethylvaleronitrile) were added as initiators to the solution in the amounts of 0.7% by mole and 2.1% by mole respectively with respect to the total amount of monomers, and the resultant mixture was heated for about 5 hours at 75° C. Then, the obtained reacted mixture was poured into a large amount of a mixture of methanol and ion exchanged water (4/1) to precipitate a resin. The obtained resin was filtrated to obtain the copolymer having a weight average molecular weight of about 14000 in 74% yield. This resin, which had the structural units of the following formulae, was referred to Resin X3.

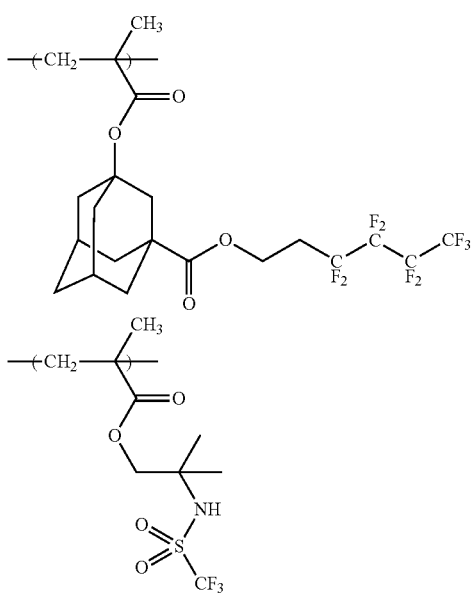

Example 9

Synthesis of Resin X4

Monomer (I-15) was used, and propylene glycol monomethyl ether acetate was added thereto in the amount equal to 1.5 times by mass of the total amount of monomers to obtain a solution. Azobisisobutyronitrile and azobis(2,4-dimethylvaleronitrile) were added as initiators to the solution in the amounts of 0.7% by mole and 2.1% by mole respectively with respect to the total amount of monomers, and the resultant mixture was heated for about 5 hours at 75° C. Then, the obtained reacted mixture was poured into a large amount of a mixture of methanol and water to precipitate a resin. The obtained resin was filtrated. Thus obtained resin was dissolved in another propylene glycol monomethyl ether acetate to obtain a solution, and the solution was poured into a mixture of methanol and water to precipitate the resin. The obtained resin was filtrated. These operations were repeated twice to obtain the copolymer having a weight average molecular weight of about 13000 in 75% yield. This resin, which had the structural units of the following formula, was referred to Resin X4.

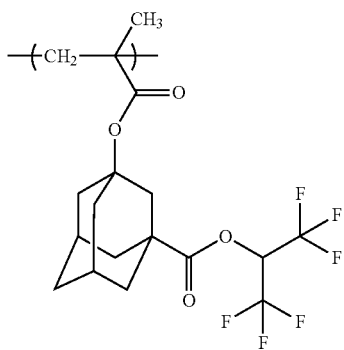

Example 10

Synthesis of Resin X5

Monomer (I-15) and monomer (a5-1-1) were mixed together with the mole ratio of monomer (I-15) and monomer (a5-1-1)=50:50, and propylene glycol monomethylether acetate was added thereto in the amount equal to 1.5 times by mass of the total amount of monomers to obtain a solution. Azobisisobutyronitrile and azobis(2,4-dimethylvaleronitrile) were added as initiators to the solution in the amounts of 0.7% by mole and 2.1% by mole respectively with respect to the total amount of monomers, and the resultant mixture was heated for about 5 hours at 75° C. Then, the obtained reacted mixture was poured into a large amount of a mixture of methanol and ion exchanged water (4/1) to precipitate a resin. The obtained resin was filtrated to obtain the copolymer having a weight average molecular weight of about 13000 in 78% yield. This resin, which had the structural units of the following formulae, was referred to Resin X5.

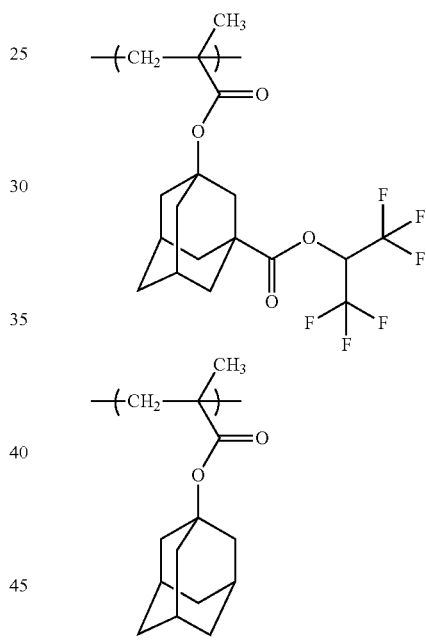

Example 11

Synthesis of Resin X6

Monomer (I-15) and monomer (a5-1-20) were mixed together with the mole ratio of monomer (I-15) and monomer (a5-1-20)=50:50, and propylene glycol monomethylether acetate was added thereto in the amount equal to 1.5 times by mass of the total amount of monomers to obtain a solution. Azobisisobutyronitrile and azobis(2,4-dimethylvaleronitrile) were added as initiators to the solution in the amounts of 0.7% by mole and 2.1% by mole respectively with respect to the total amount of monomers, and the resultant mixture was heated for about 5 hours at 75° C. Then, the obtained reacted mixture was poured into a large amount of a mixture of methanol and ion exchanged water (4/1) to precipitate a resin. The obtained resin was filtrated to obtain the copolymer having a weight average molecular weight of about 14000 in 73% yield. This resin, which had the structural units of the following formulae, was referred to Resin X6.

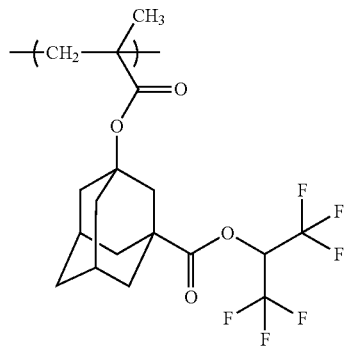

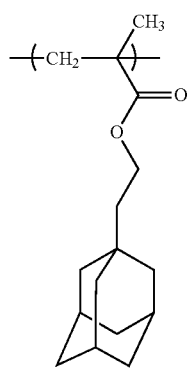

Example 12

Synthesis of Resin X7

Monomer (I-3) was used, and propylene glycol monomethyl ether acetate was added thereto in the amount equal to 1.5 times by mass of the total amount of monomers to obtain a solution. Azobisisobutyronitrile and azobis(2,4-dimethylvaleronitrile) were added as initiators to the solution in the amounts of 0.7% by mole and 2.1% by mole respectively with respect to the total amount of monomers, and the resultant mixture was heated for about 5 hours at 75° C. Then, the obtained reacted mixture was poured into a large amount of a mixture of methanol and water to precipitate a resin. The obtained resin was filtrated. Thus obtained resin was dissolved in another propylene glycol monomethyl ether acetate to obtain a solution, and the solution was poured into a mixture of methanol and water to precipitate the resin. The obtained resin was filtrated. These operations were repeated twice to obtain the polymer having a weight average molecular weight of about 15000 in 82% yield. This resin, which had the structural units of the following formula, was referred to Resin X7.

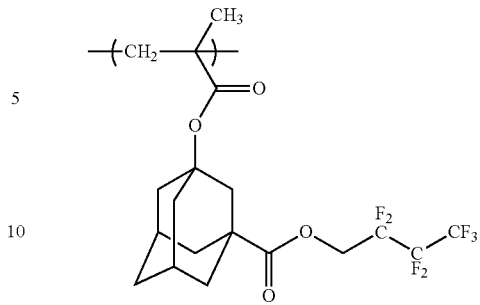

Example 13

Synthesis of Resin X8

Monomer (I-10) was used, and propylene glycol monomethyl ether acetate was added thereto in the amount equal to 1.5 times by mass of the total amount of monomers to obtain a solution. Azobisisobutyronitrile and azobis(2,4-dimethylvaleronitrile) were added as initiators to the solution in the amounts of 0.7% by mole and 2.1% by mole respectively with respect to the total amount of monomers, and the resultant mixture was heated for about 5 hours at 75° C. Then, the obtained reacted mixture was poured into a large amount of a mixture of methanol and water to precipitate a resin. The obtained resin was filtrated. Thus obtained resin was dissolved in another propylene glycol monomethyl ether acetate to obtain a solution, and the solution was poured into a mixture of methanol and water to precipitate the resin. The obtained resin was filtrated. These operations were repeated twice to obtain the polymer having a weight average molecular weight of about 14000 in 69% yield. This resin, which had the structural units of the following formula, was referred to Resin X8.

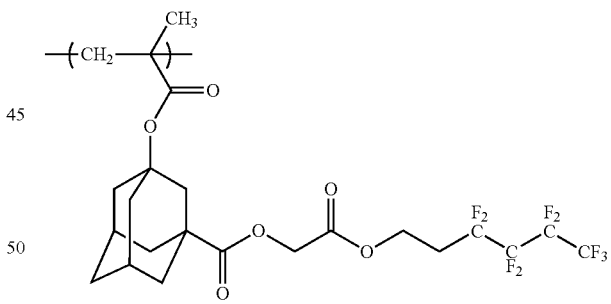

Example 14

Synthesis of Resin X9

Monomer (I-15) was used, and propylene glycol monomethyl ether acetate was added thereto in the amount equal to 1.5 times by mass of the total amount of monomers to obtain a solution. Azobisisobutyronitrile and azobis(2,4-dimethylvaleronitrile) were added to the solution as initiators in the amounts of 0.8% by mole and 2.4% by mole respectively with respect to the total amount of monomers, and the resultant mixture was heated for about 5 hours at 75° C. Then, the obtained reacted mixture was poured into a large amount of a mixture of methanol and water to precipitate a resin. The obtained resin was filtrated. Thus obtained resin was dissolved in another propylene glycol monomethyl ether acetate to obtain a solution, and the solution was poured into a mixture of methanol and water to precipitate a resin. The obtained resin was filtrated. These operations were repeated twice to obtain the polymer having a weight average molecular weight of about 11000 in 77% yield. This resin, which had the structural units of the following formula, was referred to Resin X9.

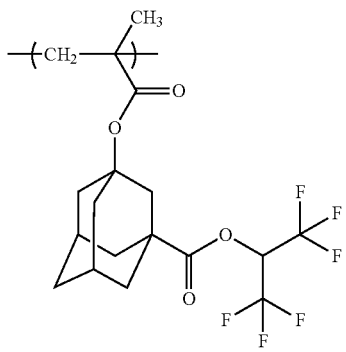

Example 15

Synthesis of Resin X10

Monomer (I-15) was used, and propylene glycol monomethyl ether acetate was added thereto in the amount equal to 1.5 times by mass of the total amount of monomers to obtain a solution. Azobisisobutyronitrile and azobis(2,4-dimethylvaleronitrile) were added as initiators to the solution in the amounts of 0.9% by mole and 2.7% by mole respectively with respect to the total amount of monomers, and the resultant mixture was heated for about 5 hours at 75° C. Then, the obtained reacted mixture was poured into a large amount of a mixture of methanol and water to precipitate a resin. The obtained resin was filtrated. Thus obtained resin was dissolved in another propylene glycol monomethyl ether acetate to obtain a solution, and the solution was poured into a mixture of methanol and water to precipitate the resin. The obtained resin was filtrated. These operations were repeated twice, resulting in 77% yield of Resin X10 having a weight average molecular weight of about 9100. This resin, which had the structural units of the following formula, was referred to Resin X10.

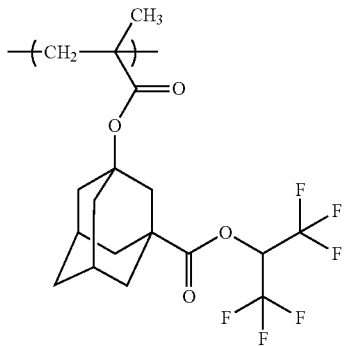

Example 16

Synthesis of Resin X11

Monomer (I-15) was used, and propylene glycol monomethyl ether acetate was added thereto in the amount equal to 1.5 times by mass of the total amount of monomers to obtain a solution. Azobisisobutyronitrile and azobis(2,4-dimethylvaleronitrile) were added as initiators to the solution in the amounts of 1% by mole and 3% by mole respectively with respect to the total amount of monomers, and the resultant mixture was heated for about 5 hours at 75° C. Then, the obtained reacted mixture was poured into a large amount of a mixture of methanol and water to precipitate a resin. The obtained resin was filtrated. Thus obtained resin was dissolved in another propylene glycol monomethyl ether acetate to obtain a solution, and the solution was poured into a mixture of methanol and water to precipitate a resin. The obtained resin was filtrated. These operations were repeated twice to obtain the polymer having a weight average molecular weight of about 7400 in 75% yield. This resin, which had the structural units of the following formula, was referred to Resin X11.

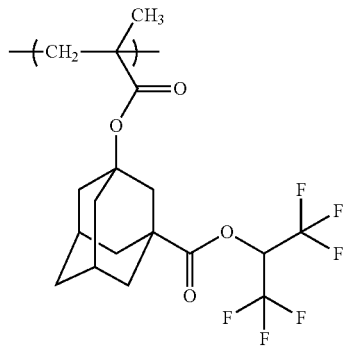

Example 17

Synthesis of Resin X12

Monomer (I-15) and monomer (a4-0-12) were mixed together with the mole ratio of monomer (I-15) and monomer (a4-0-12)=50:50, and propylene glycol monomethylether acetate was added thereto in the amount equal to 1.5 times by mass of the total amount of monomers to obtain a solution. Azobisisobutyronitrile and azobis(2,4-dimethylvaleronitrile) were added as initiators to the solution in the amounts of 0.9% by mole and 2.7% by mole respectively with respect to the total amount of monomers, and the resultant mixture was heated for about 5 hours at 75° C. Then, the obtained reacted mixture was poured into a large amount of a mixture of methanol and ion exchanged water (4/1) to precipitate a resin. The obtained resin was filtrated to obtain the copolymer having a weight average molecular weight of about 9200 in 82% yield. This resin, which had the structural units of the following formulae, was referred to Resin X12.

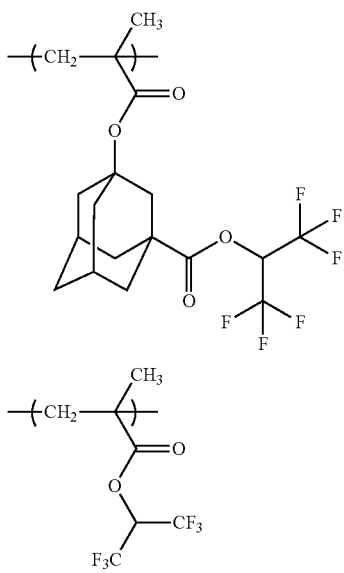

Example 18

Synthesis of Resin X13

Monomer (I-15), monomer (a4-0-12) and monomer (a5-1-1) were mixed together with the mole ratio of monomer (I-15), monomer (a4-0-12) and monomer (a5-1-1)=25:25:50, and propylene glycol monomethylether acetate was added thereto in the amount equal to 1.5 times by mass of the total amount of monomers to obtain a solution. Azobisisobutyronitrile and azobis(2,4-dimethylvaleronitrile) were added as initiators to the solution in the amounts of 0.9% by mole and 2.7% by mole respectively with respect to the total amount of monomers, and the resultant mixture was heated for about 5 hours at 75° C. Then, the obtained reacted mixture was poured into a large amount of a mixture of methanol and ion exchanged water (4/1) to precipitate a resin. The obtained resin was filtrated to obtain the copolymer having a weight average molecular weight of about 9000 in 78% yield. This resin, which had the structural units of the following formulae, was referred to Resin X13.

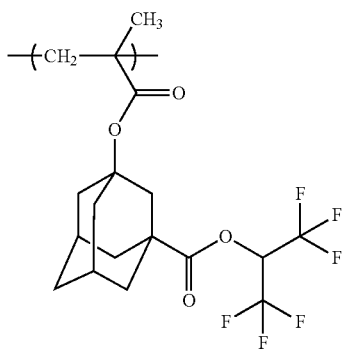

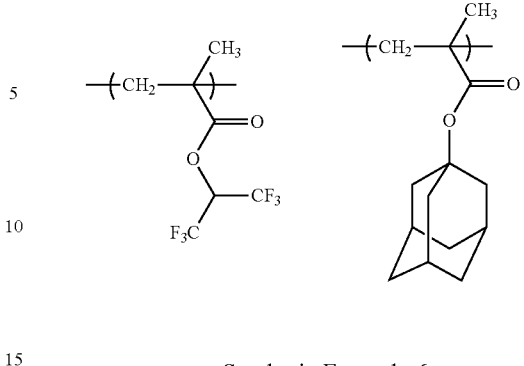

Synthesis Example 6

Synthesis of Resin Xx1

Monomer (IX) and monomer (ax) were mixed together with the mole ratio of monomer (IX) and monomer (ax) =45:55, and propylene glycol monomethylether acetate was added thereto in the amount equal to 1.5 times by mass of the total amount of monomers to obtain a solution. Azobisisobutyronitrile and azobis(2,4-dimethylvaleronitrile) were added as initiators to the solution in the amounts of 0.7% by mole and 2.1% by mole respectively with respect to the total amount of monomers, and the resultant mixture was heated for about 5 hours at 75° C. Then, the obtained reacted mixture was poured into a large amount of a mixture of methanol and ion exchanged water (4/1) to precipitate a resin. The obtained resin was filtrated to obtain the copolymer having a weight average molecular weight of about 15000 in 80% yield. This resin, which had the structural units of the following formulae, was referred to Resin Xx1.

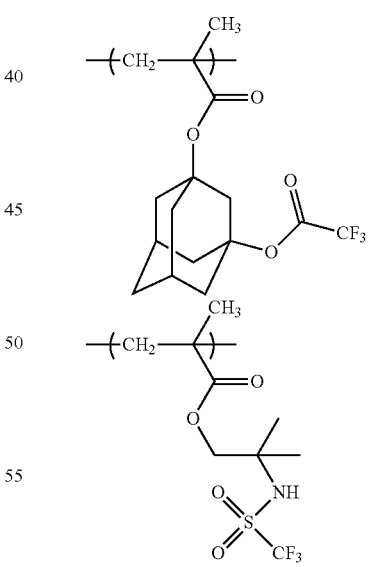

(Preparing Resist Composition)

Resist compositions were prepared by mixing and dissolving each of the components shown in Table 1, and then filtrating through a fluororesin filter having 0.2 μm pore diameter. After preserving the prepared resist compositions at 30° C. for three weeks, the evaluations described later were carried out.

TABLE 1

| Resist Comp. | Resin (parts) | Acid Generator (B) (parts) | Weak Acid Inner Salt (D) (parts) | PB/PEB (° C./° C.) |
|---|---|---|---|---|
| Composition 1 | X1/A1 = 0.7/10 | B1-21/B1-22 = 0.9/0.4 | D1 = 0.28 | 90/85 |
| Composition 2 | X2/A1 = 0.7/10 | B1-21/B1-22 = 0.9/0.4 | D1 = 0.28 | 90/85 |
| Composition 3 | X1/A1 = 0.7/10 | B1-5/B1-22 = 0.4/0.4 | D1 = 0.28 | 90/85 |
| Composition 4 | X3/A1 = 0.7/10 | B1-21/B1-22 = 0.9/0.4 | D1 = 0.28 | 90/85 |
| Composition 5 | X3/A2 = 0.7/10 | B1-21/B1-22 = 0.9/0.4 | D1 = 0.28 | 110/105 |
| Composition 6 | X3/A2 = 0.7/10 | B1-3 = 1.0 | D1 = 0.28 | 110/105 |
| Composition 7 | X4/A1 = 0.7/10 | B1-21/B1-22 = 0.9/0.4 | D1 = 0.28 | 90/85 |
| Composition 8 | X5/A1 = 0.7/10 | B1-21/B1-22 = 0.9/0.4 | D1 = 0.28 | 90/85 |
| Composition 9 | X6/A1 = 0.7/10 | B1-21/B1-22 = 0.9/0.4 | D1 = 0.28 | 90/85 |
| Composition 10 | X4/A1 = 0.4/10 | B1-21/B1-22 = 0.9/0.4 | D1 = 0.28 | 90/85 |
| Composition 11 | X7/A1 = 0.4/10 | B1-21/B1-22 = 0.9/0.4 | D1 = 0.28 | 90/85 |
| Composition 12 | X8/A1 = 0.4/10 | B1-21/B1-22 = 0.9/0.4 | D1 = 0.28 | 90/85 |
| Composition 13 | X9/A1 = 0.4/10 | B1-21/B1-22 = 0.9/0.4 | D1 = 0.28 | 90/85 |
| Composition 14 | X10/A1 = 0.4/10 | B1-21/B1-22 = 0.9/0.4 | D1 = 0.28 | 90/85 |
| Composition 15 | X11/A1 = 0.4/10 | B1-21/B1-22 = 0.9/0.4 | D1 = 0.28 | 90/85 |
| Composition 16 | X12/A1 = 0.4/10 | B1-21/B1-22 = 0.9/0.4 | D1 = 0.28 | 90/85 |
| Composition 17 | X13/A1 = 0.4/10 | B1-21/B1-22 = 0.9/0.4 | D1 = 0.28 | 90/85 |
| Comparative Composition 1 | Xx1/A2 = 0.7/10 | B1-3 = 1.0 | D1 = 0.28 | 110/105 |

<Resin>

A1, A2, X1, X2, X3, X4, X5, X6, X7, X8, X9, X10, X11, X12, X13, Xx1:Resin A1, Resin A2, Resin X1, Resin X2, Resin X3, Resin X4, Resin X5, Resin X6, Resin X7, Resin X8, Resin X9, Resin X10, Resin X11, Resin X12, Resin X13, Resin Xx1, prepared by the above Synthesis of Resin.

<Acid Generator>

B1-3: The following salt, prepared by a method according to the method described in the Examples of JP2010-152341A

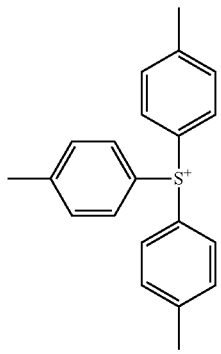

B1-5: Salt represented by the formula (B1-5)

B1-21: Salt represented by the formula (B1-21)

B1-22: Salt represented by the formula (B1-22) <Weakly Acidic Inner Salt (D)>

D1: The following compound, Products of Tokyo Chemical Industry Co., LTD

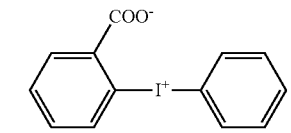

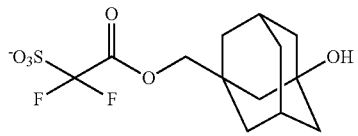

<Solvent of Resist composition>

| | |
|---|---|
| Propyleneglycolmonomethylether acetate | 265 parts |
| Propyleneglycolmonomethylether | 20 parts |
| 2-Heptanone | 20 parts |
| γ-butyrolactone | 3.5 parts |

<Producing Negative Resist Patterns>

A composition for an organic antireflective film ("ARC-29", by Nissan Chemical Co. Ltd.) was applied onto 12-inch silicon wafers and baked for 60 seconds at 205° C. to form a 78 nm thick organic antireflective film.

On one of the treated wafers, one of the resist compositions was then applied thereon by spin coating in such a manner that the thickness of the film after drying (pre-baking) became 100 nm.

The obtained wafer was then pre-baked for 60 sec on a direct hot plate at the temperature given in the "PB" column in Table 1.

On the wafer on which the resist film had thus been formed, the film was exposed through a mask for forming 1:1 Line and space patterns (pitch 70 to 100 nm/line width 35 to 50 nm) with changing exposure quantity stepwise using an ArF excimer laser stepper for immersion lithography ("XT:1900Gi" by ASML Ltd.: Na=1.35, Annular $\sigma_{out}$=0.85 $\sigma_{in}$=0.65 XY-pol.). Ultrapure water was used for medium of immersion.

After the exposure, post-exposure baking was carried out for 60 seconds at the temperature given in the "PEB" column in Table 1.

Then, development was carried out with butyl acetate (obtained from Tokyo Chemical Industry Co., LTD) at 23 degree C. for 20 seconds in the manner of dynamic dispensing method to obtain negative resist patterns.

Effective sensitivity was represented as the exposure quantity at which line and space patterns with 50 nm of line width was resolved by exposure.

<Evaluation of Defects>

Each of the above-mentioned resist compositions was applied on a 12-inch-silicon wafer by spin coating in such a manner that the thickness of the resulting film after drying became 150 nm.

The obtained wafer was then pre-baked for 60 seconds on a direct hot plate at the temperature given in the "PB" column in Table 1 to obtain a composition layer.

The thus obtained wafer with the produced composition layer was rinsed with water for 60 seconds using a developing apparatus (ACT-12, Tokyo electron Co. Ltd.).

Thereafter, the number of defects was counted using a defect inspection apparatus (KLA-2360, KLA-Tencor Co. Ltd.)

Table 2 illustrates the results thereof.

<Evaluation of Resolution>

A resist pattern produced where exposure was conducted at the exposure quantity equivalent to effective sensitivity was observed with a scanning electron microscope.

In Table 2, a "oo" was given when the resist pattern with the line width being 43 nm or less was resolved, a "o" was given when the resist pattern with the line width being from more than 43 nm to less than 48 nm was resolved, a "x" was given when only the resist pattern with the line width being more than 48 nm was resolved or when the resolved resist pattern has 48 nm or less of the line width with a rounded or skirt shape in the top of its profile or with the pattern collapse, and Table 2 illustrates the results thereof. The number in parentheses represents the minimum line width values of the resolved pattern without defects.

TABLE 2

|  | Resist Composition | Defects | Resolution |
| --- | --- | --- | --- |
| Ex. 19 | Composition 1 | 230 | oo(43 nm) |
| Ex. 20 | Composition 2 | 370 | oo(43 nm) |
| Ex. 21 | Composition 3 | 270 | o(44 nm) |
| Ex. 22 | Composition 4 | 480 | o(45 nm) |
| Ex. 23 | Composition 5 | 790 | o(46 nm) |
| Ex. 24 | Composition 6 | 880 | o(46 nm) |
| Ex. 25 | Composition 7 | 150 | oo(42 nm) |
| Ex. 26 | Composition 8 | 180 | oo(43 nm) |
| Ex. 27 | Composition 9 | 170 | oo(43 nm) |
| Ex. 28 | Composition 10 | 180 | oo(41 nm) |
| Ex. 29 | Composition 11 | 210 | oo(43 nm) |
| Ex. 30 | Composition 12 | 200 | oo(43 nm) |
| Ex. 31 | Composition 13 | 180 | oo(41 nm) |
| Ex. 32 | Composition 14 | 170 | oo(41 nm) |
| Ex. 33 | Composition 15 | 180 | oo(40 nm) |
| Ex. 34 | Composition 16 | 180 | oo(41 nm) |
| Ex. 35 | Composition 17 | 190 | oo(41 nm) |
| Comparative Ex. 1 | Comparative Composition 1 | 2200 | x(50 nm) |

The resin including a structural unit derived from the compound of the disclosure is useful for resist compositions. A resist composition which includes the resin shows satisfactory storage stability, specifically shows excellent resolution and less defects in the obtained resist pattern even after storage. Therefore, the resist composition can be used for semiconductor microfabrication.

What is claimed is:

1. A resin consisting of a structural unit derived from a compound represented by formula (I)

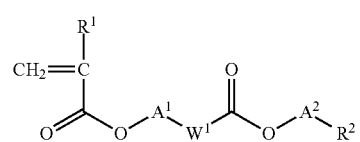

(I)

wherein $R^1$ represents a hydrogen atom, a halogen atom or a $C_1$ to $C_6$ alkyl group that may have a halogen atom;

$R^2$ represents $-(CH_2)_n-R^f$ or $-CH(R^{fa})(R^{fb})$, wherein n represents an integer of 1 to 6, and $R^f$, $R^{fa}$, and $R^{fb}$ each independently represent a $C_1$ to $C_6$ perfuloroalkyl group;

$W^1$ represents a cyclopentanediyl group, a cyclohexanediyl group, an adamantanediyl group or a norbomanediyl group;

$A^1$ and $A^2$ each independently represent a single bond or $*-A^3-X^1-(A^4-X^2)_a-$;

$A^3$ and $A^4$ each independently represent a $C_1$ to $C_6$ alkanediyl;

$X^1$ and $X^2$ each independently represents $-O-$, $-CO-O-$ or $-O-CO-$;

a represents 0 or 1; and

* represents a binding site to an oxygen atom;

or consisting of the structural unit derived from a compound represented by formula (I) and at least one selected from the group consisting of a structural unit represented by the formula (a4-0), (a4-1) or (a4-4),

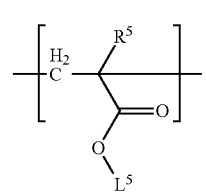

(a4-0)

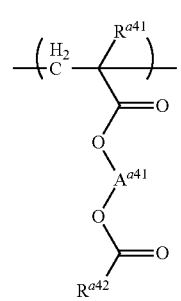

(a4-1)

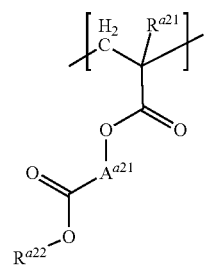

(a4-4)

wherein $R^5$ represents a hydrogen atom or a methyl group, $L^5$ represent a single bond or a $C_1$ to $C_4$ saturated aliphatic hydrocarbon group, $L^3$ represents a $C_1$ to $C_8$ perfluoroalkanediyl group or a $C_5$ to $C_{12}$ perfluorocycloalkanediyl group, $R^6$ represents a hydrogen atom or a fluorine atom, $R^{a41}$ represents a hydrogen atom or a methyl group, $R^{a42}$ represents an optionally substituted $C_1$ to $C_{20}$ hydrocarbon group where a methylene group may be replaced by an oxygen atom or a carbonyl group, and $A^{a41}$ represents an optionally substituted $C_1$ to $C_6$ alkanediyl group or a group represented by the formula (a-g1), $$**\text{—}A^{a42}\text{—}(X^{a41}\text{—}A^{a43})_s\text{—}X^{a42}\text{—}A^{a44}\text{—}* \qquad (a\text{-}g1)$$

wherein s represents 0 or 1, $A^{a42}$ and $A^{a44}$ independently represent an optionally substituted $C_1$ to $C_5$ aliphatic hydrocarbon group, $A^{a43}$ represents a single bond or an optionally substituted $C_1$ to $C_5$ aliphatic hydrocarbon group, and $X^{a41}$ and $X^{a42}$ independently represent —O—, —CO—, —CO—O— or —O—CO—, provided that the total carbon number contained in the group of $A^{a42}$, $A^{a43}$, $A^{a44}$, $X^{a41}$ and $X^{a42}$ is 6 or less, and at least one of $A^{a41}$ and $R^{a42}$ has a halogen atom as a substituent, and * and ** represent a binding site, and * represents a binding site to —O—CO—$R^{a42}$, $R'^{21}$ represents a hydrogen atom or a methyl group, $A'^{21}$ represents —$(CH_2)_{j1}$—, —$(CH_2)_{j2}$—O—$(CH_2)_{j3}$— or —$(CH_2)_{j4}$—CO—O—$(CH_2)_{j5}$—, j1 to j5 independently represents an integer of 1 to 6, and $R'^{22}$ represents a $C_1$ to $C_{10}$ hydrocarbon group having a fluorine atom, and a structural unit represented by the formula (a5-1);

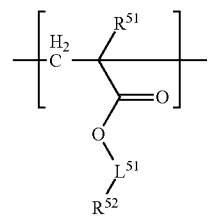

(a5-1)

wherein $R^{51}$ represents a hydrogen atom or a methyl group, $R^{52}$ represents a $C_3$ to $C_{18}$ alicyclic hydrocarbon group where a hydrogen atom may be replaced by a $C_1$ to $C_8$ aliphatic hydrocarbon group or a hydroxy group, provided that a hydrogen atom contained in the carbon atom bonded to $L^{51}$ is not replaced by the $C_1$ to $C_8$ aliphatic hydrocarbon group, and $L^{51}$ represents a single bond or a $C_1$ to $C_{18}$ divalent saturated hydrocarbon group where a methylene group may be replaced by an oxygen atom or a carbonyl group.

2. A resist composition comprising the resin according to claim 1, a resin having an acid-labile group, and an acid generator.

3. A method for producing a resist pattern comprising steps (1) to (5);
  (1) applying the resist composition according to claim 2 onto a substrate;
  (2) drying the applied composition to form a composition layer;
  (3) exposing the composition layer;
  (4) heating the exposed composition layer, and
  (5) developing the heated composition layer.

* * * * *